United States Patent
Delbeck et al.

(10) Patent No.: US 12,180,227 B2
(45) Date of Patent: Dec. 31, 2024

(54) DIAZABICYCLIC SUBSTITUTED IMIDAZOPYRIMIDINES AND THEIR USE FOR THE TREATMENT OF BREATHING DISORDERS

(71) Applicants: Bayer Aktiengesellschaft; Bayer Pharma Aktiengesellschaft, Berlin (DE)

(72) Inventors: Martina Delbeck, Heiligenhaus (DE); Michael Hahn, Langenfeld (DE); Thomas Müller, Langenfeld (DE); Klemens Lustig, Wuppertal (DE); Karl Collins, Düsseldorf (DE); Niels Lindner, Wuppertal (DE); Janine Nicolai, Essen (DE); Moritz Beck-Broichsitter, Darmstadt (DE); Udo Albus, Florstadt (DE); Doris Gehring, Kelkheim (DE); Björn Rosenstein, Bad Soden-Salmünster (DE)

(73) Assignees: Bayer Aktiengesellschaft, Leverkusen (DE); Bayer Pharma Aktiengesellschaft, Berlin (DE)

( * ) Notice: Subject to any disclaimer, the term of this patent is extended or adjusted under 35 U.S.C. 154(b) by 186 days.

(21) Appl. No.: 17/305,927

(22) Filed: Jul. 16, 2021

(65) Prior Publication Data

US 2022/0017540 A1 Jan. 20, 2022

Related U.S. Application Data

(62) Division of application No. 16/622,233, filed as application No. PCT/EP2018/064977 on Jun. 7, 2018, now Pat. No. 11,098,063.

(30) Foreign Application Priority Data

Jun. 14, 2017 (EP) ..................................... 17176046
Sep. 26, 2017 (EP) ..................................... 17193252

(51) Int. Cl.
*A61P 11/04* (2006.01)
*A61P 11/00* (2006.01)
*C07D 519/00* (2006.01)

(52) U.S. Cl.
CPC ............ *C07D 519/00* (2013.01); *A61P 11/00* (2018.01)

(58) Field of Classification Search
CPC ..................................................... A61P 11/04
See application file for complete search history.

(56) References Cited

U.S. PATENT DOCUMENTS

| | | | |
|---|---|---|---|
| 6,833,364 B1 | 12/2004 | Straub et al. | |
| 6,864,287 B1 | 3/2005 | Alonso-Alija et al. | |
| 7,541,362 B2 | 6/2009 | Atwal | |
| 7,855,194 B2 | 12/2010 | Binggeli | |
| 9,096,592 B2 | 8/2015 | Follmann | |
| 9,127,001 B2 | 9/2015 | Bialy et al. | |
| 9,216,978 B2 | 12/2015 | Follmann | |
| 9,284,333 B2 | 3/2016 | Bialy et al. | |
| 9,993,476 B2 | 6/2018 | Follmann | |
| 10,414,765 B2 | 9/2019 | Delbeck | |
| 10,759,794 B2 | 9/2020 | Delbeck | |
| 11,098,063 B2 | 8/2021 | Delbeck | |
| 2002/0022624 A1 | 2/2002 | Dinnell et al. | |
| 2002/0173514 A1 | 11/2002 | Stasch | |
| 2004/0082798 A1 | 4/2004 | Alonso-Alija et al. | |
| 2004/0176446 A1 | 9/2004 | Alonso-Alija et al. | |

(Continued)

FOREIGN PATENT DOCUMENTS

| CA | 3031136 A1 | 1/2018 |
|---|---|---|
| CN | 101405284 A | 4/2009 |

(Continued)

OTHER PUBLICATIONS

"FLIPR Membrane Potential Assay Kits," located at https://www.moleculardevices.com/products/assay-kits/ion-channel/flipr-membrane-potential, last visited on Dec. 6, 2018, three pages.

(Continued)

*Primary Examiner* — Brian E McDowell
(74) *Attorney, Agent, or Firm* — Morrison & Foerster LLP

(57) ABSTRACT

The present invention relates to novel diazabicyclically substituted imidazo[1,2-a]pyrimidine derivatives, such as compounds of the general formula (I):

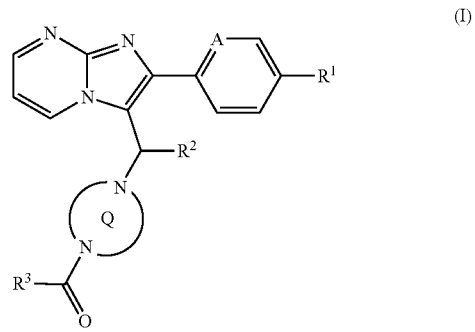

to methods for producing the same, to the use thereof either alone or in combinations for the treatment and/or prevention of diseases, as well as to their use for preparing medicaments for the treatment and/or prevention of diseases, especially for treatment and/or prevention of breathing disorders, including sleep-related breathing disorders such as obstructive and central sleep apnoea and snoring.

10 Claims, No Drawings

(56) References Cited

U.S. PATENT DOCUMENTS

| | | |
|---|---|---|
| 2004/0224945 A1 | 11/2004 | Straub |
| 2005/0239823 A1 | 10/2005 | Oberbörsch et al. |
| 2006/0052397 A1 | 3/2006 | Alonso-Alija et al. |
| 2006/0094769 A1 | 5/2006 | Alonso-Alija |
| 2008/0058314 A1 | 3/2008 | Alonso-Alija et al. |
| 2009/0149496 A1 | 6/2009 | Brendel |
| 2012/0022084 A1 | 1/2012 | Follmann |
| 2013/0267548 A1 | 10/2013 | Follmann et al. |
| 2014/0148433 A1 | 5/2014 | Follmann et al. |
| 2014/0350020 A1 | 11/2014 | Follmann et al. |
| 2015/0018342 A1 | 1/2015 | Bialy et al. |
| 2018/0370965 A1 | 12/2018 | Delbeck et al. |
| 2019/0062326 A1 | 2/2019 | Delbeck et al. |
| 2020/0085734 A1 | 3/2020 | Anlahr |
| 2020/0093737 A1 | 3/2020 | Anlahr |
| 2020/0140461 A1 | 5/2020 | Delbeck |
| 2021/0024545 A1 | 1/2021 | Delbeck et al. |
| 2021/0393624 A1 | 12/2021 | Stein |
| 2022/0259228 A1 | 8/2022 | Delbeck |

FOREIGN PATENT DOCUMENTS

| | | |
|---|---|---|
| CN | 101636154 A | 1/2010 |
| EP | 1974729 A1 | 10/2008 |
| EP | 2671582 A1 | 7/2016 |
| JP | 2004507442 A | 3/2004 |
| JP | 2009543785 A | 12/2009 |
| JP | 2018536693 A | 12/2018 |
| JP | 2018538296 A | 12/2018 |
| JP | 2019521170 A | 7/2019 |
| JP | 6896113 B2 | 6/2021 |
| WO | 200006568 A1 | 2/2000 |
| WO | 200006569 A1 | 2/2000 |
| WO | 200119355 A2 | 3/2001 |
| WO | 200119776 A2 | 3/2001 |
| WO | 200119778 A1 | 3/2001 |
| WO | 200119780 A2 | 3/2001 |
| WO | 2002002557 A2 | 1/2002 |
| WO | 200242301 A1 | 5/2002 |
| WO | 2002066478 A1 | 8/2002 |
| WO | 200270462 | 9/2002 |
| WO | 200270510 A2 | 9/2002 |
| WO | 200395451 A1 | 11/2003 |
| WO | 200435578 A1 | 4/2004 |
| WO | 2008008517 A3 | 12/2008 |
| WO | 2009143156 A3 | 1/2010 |
| WO | 2011115804 A1 | 9/2011 |
| WO | 2011147809 A1 | 12/2011 |
| WO | 2012028647 A1 | 3/2012 |
| WO | 2012059549 A1 | 5/2012 |
| WO | 2012004258 A9 | 6/2012 |
| WO | 2011113606 A8 | 10/2012 |
| WO | 2012130322 A1 | 10/2012 |
| WO | 2013037736 A1 | 3/2013 |
| WO | 2013037914 A1 | 3/2013 |
| WO | 2012143796 A3 | 6/2013 |
| WO | 2014187922 A1 | 11/2014 |
| WO | 2015144605 A1 | 10/2015 |
| WO | 2016084866 A1 | 6/2016 |
| WO | 2016085783 A1 | 6/2016 |
| WO | 2016085784 A1 | 6/2016 |
| WO | 2016088813 A1 | 6/2016 |
| WO | 2017050732 A1 | 3/2017 |
| WO | 2017097671 A1 | 6/2017 |
| WO | 2017097792 A1 | 6/2017 |
| WO | 2018015196 A1 | 1/2018 |
| WO | 2018114501 A1 | 6/2018 |
| WO | 2018114503 A1 | 6/2018 |
| WO | 2018227427 A1 | 12/2018 |
| WO | 2018228909 A1 | 12/2018 |
| WO | 2020109109 A1 | 6/2020 |
| WO | 2020225185 A1 | 11/2020 |
| WO | 2020225188 A1 | 11/2020 |

OTHER PUBLICATIONS

Artursson, P. et al. (Mar. 1991). "Correlation Between Oral Drug Absorption in Humans and Apparent Drug Permeability Coefficients in Human Intestinal Epithelial (CACO-2) Cells," Biochemical and Biophysical Research Communications 175(3): 880-885.
Bayliss et al., (2015). "The role of pH-sensitive TASK channels in central respiratory chemoreception," Pflugers Arch. 467, 467:917-929.
Berg et al., (Jul. 28, 2004). "Motoneurons Express Heteromeric TWIK-Related Acid-Sensitive K+ (Task) Channels Containing TASK-1 (KCNK3) and TASK-3 (KCNK9) Subunits," The Journal of Neuroscience 24(30):6693-6702.
Berry et al., (Mar. 12, 1997). "Upper Airway Anesthesia Reduces Phasic Genioglossus Activity During Sleep Apnea," Am J Respir Crit Care Med 156:127-132.
Bittner et al., (2009). "TASK1 modulates inflammation and neurodegeneration in autoimmune inflammation of the central nervous system," Brain 132:2501-2516.
Bittner, S. et al. (2012). "The TASK1 channel inhibitor A293 shows efficacy in a mouse model of multiple sclerosis," Experimental Neurology, 238:149-155.
Bittner, S. et al. (2013). "Endothelial TWIK-related potassium channel-1 (TREK1) regulates immune-cell trafficking into the CNS," Nature Medicine, 19(9):1161-1169.
Bobak, N. et al. (2011). "Volume regulation of murine T lymphocytes relies on voltage-dependent and two-pore domain potassium channels," Biochimica et Biophysica Acta, 1808:2036-2044.
Brouillette et al. (1979). "A neuromuscular mechanism maintaining extrathoracic airway patency," American Physiological Society 49:772-779.
Comer, J. et al. (2001). "Lipophilicity Profiles: Theory and Measurement" in Pharmacokinetic Optimization in Drug Research Biological, Physicochemical, and Computational Strategies, Testa, B. et al. eds., Verlag Helvetica Chimica Acta: Zürich, Switzerland, pp. 275-304.
Czirják et al. (2000). "TASK (TWIK-Related Acid-Sensitive K+ Channel) is Expressed in Glomerulosa Cells of Rat Adrenal Cortex and Inhibited by Angiotensin II," Molecular Endocrinology 14(6):863-874.
Decher et al. (2001). "Characterization of TASK-4, a novel member of the pH-sensitive, two-pore domain potassium channel family," FEBS Letters 492:84-89.
Decher et al. (2011). "Knock-Out of the Potassium Channel TASK-1 Leads to a Prolonged QT Interval and a Disturbed QRS Complex," Cell Physiol Biochem 28:77-86.
Ertl, P. et al. (2000). "Fast Calculation of Molecular Polar Surface Area as a Sum of Fragment-Based Contributions and Its Application to the Prediction of Drug Transport Properties," J. Med. Chem. 43(20):3714-3717.
Greene, T.W. et al. (1999) "Protective Groups in Organic Synthesis," 3rd Edition, John Wiley & Sons, Inc.
Hollandt et al. (2000). "Upper Airway Resistance Syndrome (UARS)—Obstructive Snoring," HNO 48:628-634.
Hörig, H. et al. (2004). "From bench to clinic and back: Perspective on the 1st IQPC Translational Research conference," Journal of Translational Medicine, 2(44):1-8.
International Preliminary Report on Patentability mailed on Jun. 12, 2018, for PCT Application No. PCT/EP2016/079973, filed on Dec. 7, 2016, 9 pages.
International Search Report & Written Opinion mailed on Feb. 20, 2017, for PCT/EP2016/079973, filed Dec. 7, 2016, 11 pages (German Language).
International Search Report & Written Opinion mailed on Jan. 26, 2017, for PCT/EP2016/079544, filed Dec. 2, 2016, 13 pages (German Language).
International Search Report and Written Opinion mailed on Aug. 13, 2018, for PCT/EP2018/064980, filed on Jun. 7, 2018, 11 pages.
International Search Report and Written Opinion mailed on Jul. 6, 2018, for PCT/EP2018/064977, filed on Jun. 7, 2018, 12 pages (German Language).

(56) References Cited

OTHER PUBLICATIONS

International Search Report and Written Opinion mailed on Oct. 17, 2017, for PCT/EP2017/067273, filed on Jul. 10, 2017, 13 pages (German Language).

Jungbauer, S. et al. (2017). "Sex-dependent differences in the in vivo respiratory pheynotype of the TASK-1 potassium channel knockout mouse," Respiratory Physiology & Neurobiology 245: 13-28.

Kim et al., (1999). "TBAK-1 and TASK-1, two-pore K+ channel subunits: kinetic properties and expression in rat heart," American Physiological Society H1669-H1678.

Kim et al., (2004). "Altered expression of KCNK9 in colorectal cancers," APMIS 112:588-594.

Kiper et al., (2015) "Kv1.5 blockers preferentially inhibit TASK-1 channels: TASK-1 as a target against atrial fibrillation and obstructive sleep apnea?" Pfluger Arch—Eur J Physiol 467:1081-1090.

Kocienski, P.J. et al. (2005) "Protecting Groups," 3rd edition, University of Leeds.

Kuppens, T. et al. (2004). "Determination of absolute configuration via vibrational circular dichroism," Drug Discovery Today: Technologies 1(3): 269-275.

Limberg et al., (Oct. 28, 2011). "TASK-1 Channels May Modulate Action Potential Duration of Human Atrial Cardiomyocytes," Cell Physiol Biochem 25:613-624.

Liu et al., (2005). "Protective effects of TASK-3 (KCNK9) and related 2P K channels during cellular stress," Brain Research 1031:164-173.

Meuth et al., (May 23, 2008). "TWIK-related Acid-sensitive K+ Channel 1 (TASK1) and TASK3 Critically Influence T Lymphocyte Effector Functions," The Journal of Biological Chemistry 283(21):14559-14579.

Mu et al., (Mar. 2003). "Genomic amplification and oncogenic properties of the KCNK9 potassium channel gene," Cancer Cell 3:297-302.

Pocsai et al., (2006). "Melanoma cells exhibit strong intracellular TASK-3-specific immunopositivity in both tissue sections and cell culture," Cell Mol Life Sci 63:2364-2376.

Rinne et al., (2015). "TASK-1 and TASK-3 may form heterodimers in human atrial cardiomyocytes," Journal of Molecular and Cellular Cardiology 81:71-80.

Rowland, M. et al. (2011). "Well-Stirred Model of Hepatic Clearance" Appendix E in Clinical Pharmacokinetics and Pharmacodynamics Concepts and Applications, Fourth Edition, Troy, D. et al. eds., Lippincott Williams & Wilkins: Baltimore, MD, pp. 705-708.

Roy, A. et al. (2014). "Anandamide modulates carotid sinus nerve afferent activity via TRPV1 receptors increasing responses to heat," J. Appl. Physiol. 112: 212-224.

Schmidt, C. et al. (2015). "Upregulation of K2p3.1 K+ Current Causes Action Potential Shortening in Patients with Chronic Atrial Fibrillation," Circulation, 132:82-92.

Schmidt, C. et al. (2019). "Genetic Ablation of TASK-1 (Tandem of P Domains in a Weak Inward Rectifying K+ Channel-Related Acid-Sensitive K+ Channel-1) (K2p3.1) K+ Channels Suppresses Atrial Fibrillation and Prevents Electrical Remodeling," Circ Arrhythm Electrophysiol, 12:1-10.

Schäfer, S. et al. (2008). "Failure is an option: learning from unsuccessful proof-of-concept trials," Drug Discovery Today, 13(21/22):913-916.

Stephens, P.J., (2004). "Vibrational Circular Dichroism Spectroscopy: A New Tool for the Stereochemical Characterization of Chiral Molecules" Chapter 26 in Computational Medicinal Chemistry for Drug Discovery, Bultinck, P. et al. eds., Marcel Dekker, Inc.: New York, NY, pp. 699-725.

Stühmer (1992). "Electrophysiological Recording from Xenopus Oocytes," Methods in Enzymology 207: 319-339.

Tang et al. (2009). "Endothelin-1 Inhibits Background Two-Pore Domain Channel TASK-1 in Primary Human Pulmonary Artery Smooth Muscle Cells," Am J Respir Cell Mol Biol 41:476-483.

Trapp et al. (Aug. 27, 2008). "A Role for TASK-1 (KCNK3) Channels in the Chemosensory Control of Breathing," The Journal of Neuroscience 28(35):8844-8850.

U.S. Appl. No. 17/296,914, filed internationally on Nov. 20, 2019, for Stein et al. (U.S. Patent Application is not submitted herewith pursuant to the waiver of 37 C.F.R. § 1.98(a)(2)(iii) issued by the Office on Sep. 21, 2004.).

Verse et al. (1999). "EMG Activity of the Genioglossus Muscle as One Parameter for Diagnosing for Obstructive Sleep Apnea," Somnologie 3:14-20 (Summary in English).

Vrints et al. (2013). "Cardiovascular Mechanisms and Consequences of Obstructive Sleep Aponea," Acta Clinica Belgica 68(3):169-178.

Whiteaker et al. (2001). "Validation of FLIPR Membrane Potential Dye for High Throughput Screening of Potassium Channel Modulators," Journal of Biomolecular Screening 6(5): 305-312.

Wiedmann, F. et al. (2020). "Pharmacologic TWIK-Related Acid-Sensitive K+ Channel (TASK-1) Potassium Channel Inhibitor A293 Facilitates Acute Cardioversion of Paroxysmal Atrial Fibrillation in a Porcine Large Animal Model," J Am Heart Assoc. 9:1-16.

Wirth et al. (2013). "Sensitization of Upper Airway Mechanoreceptors as a New Pharmacologic Principle to Treat Obstructive Sleep Apnea: Investigations with AVE0118 in Anesthetized Pigs," SLEEP 36(5): 699-708.

Borsotto, M. et al. (2015). "Targeting two-pore domain K+ channels TREK-1 and TASK-3 for the treatment of depression: A new therapeutic concept." Br. J. Pharmacol. 172, 771-784.

Cooper, A. et al. (2020). "Inhibition of histone deacetylation rescues phenotype in a mouse model of Birk-Barel intellectual disability syndrome." Nat. Commun. 11, 1-14.

Cotten, J.F. (2013) "TASK-1 (KCNK3) and TASK-3 (KCNK9) tandem pore potassium channel antagonists stimulate breathing in isoflurane-anesthetized rats." Anesth. Analg. 116, 810-816.

Cunningham, K.P. et al. (2020). "Effects of the ventilatory stimulant, doxapram on human TASK-3 (KCNK9, K2P9.1) channels and TASK-1 (KCNK3, K2P3.1) channels." Acta Physiol. 228, e13361.

Donner, B.C. et al. (2011). "Functional role of TASK-1 in the heart: Studies in TASK-1-deficient mice show prolonged cardiac repolarization and reduced heart rate variability." Basic Res. Cardiol. 106, 75-87.

Ehling P. et al. (2015). "The CNS under pathophysiologic attack—examining the role of $K_2p$ channels." Pflugers Arch. 467(5):959-972.

Gada, K. et al. (2019). "Two-pore domain potassium channels: Emerging targets for novel analgesic drugs: IUPHAR Review 26." Br. J. Pharmacol. 176, 256-266.

García, G. et al. (2019). "Spinal TASK-1 and TASK-3 modulate inflammatory and neuropathic pain." Eur. J. Pharmacol. 862, 11 pages.

Gierten, J. et al. (2010). "The human cardiac K2P3.1 (TASK-1) potassium leak channel is a molecular target for the class III antiarrhythmic drug amiodarone." Naunyn Schmiedebergs Arch. Pharmacol. 381, 261-270.

Gotter, A.L. et al. (2011). "TASK-3 as a potential antidepressant target." Brain Res. 2011, 1416, 69-79.

Gurney, A. et al. (2009). "Two-pore potassium channels in the cardiovascular system." Eur. Biophys. J. 38, 305-318.

Koizumi, H. et al. (2010). "TASK channels contribute to the K+-dominated leak current regulating respiratory rhythm generation in vitro." J. Neurosci. 30, 4273-4284.

Kraft, M. et al. (2021). "Current Drug Treatment Strategies for Atrial Fibrillation and TASK-1 Inhibition as an Emerging Novel Therapy Option." Front. Pharmacol. 12, 1-21.

Liang, B. et al. (2014). "Genetic variation in the two-pore domain potassium channel, TASK-1, may contribute to an atrial substrate for arrhythmogenesis." J. Mol. Cell. Cardiol. 67, 69-76.

Liao, P. et al. (2019). "Selective activation of TWIK-related acid-sensitive K+ 3 subunit-containing channels is analgesic in rodent models." Sci. Transl. Med. 11, 1-12.

Linden, A.M. et al. (2007). "TASK-3 knockout mice exhibit exaggerated nocturnal activity, impairments in cognitive functions, and reduced sensitivity to inhalation anesthetics." J. Pharmacol. Exp. Ther. 2007, 323, 924-934.

(56) References Cited

OTHER PUBLICATIONS

Marsh, B. et al. (2012). "Leak K channel mRNAs in dorsal root ganglia: Relation to inflammation and spontaneous pain behaviour." Mol. Cell. Neurosci. 49, 375-386.

Mondéjar-Parreño, G. (2022). "Unraveling the Role of K2P Channels in Atrial Fibrillation." Front. Biosci. 14(4), 31, 1-13.

Pang, D.S. et al. (2009). "An unexpected role for TASK-3 potassium channels in network oscillations with implications for sleep mechanisms and anesthetic action." Proc. Natl. Acad. Sci. USA, 106, 17546-17551.

Putzke, C. et al. (2007). "The acid-sensitive potassium channel TASK-1 in rat cardiac muscle." Cardiovasc. Res. 75, 59-68.

Ratte, A. et al. (2019). "Antiarrhythmic Properties of Ranolazine: Inhibition of Atrial Fibrillation Associated TASK-1 Potassium Channels." Front. Pharmacol. 10, 1-13.

Ren, W.J. et al. (2020). "TASK-3: New Target for Pain-Relief." Neurosci. Bull. 36, 951-954.

Schmidt, C. et al. (2017). "Inverse remodeling of K2P3.1 K+ channel expression and action potential duration in left ventricular dysfunction and atrial fibrillation: Implications for patient-specific antiarrhythmic drug therapy." Eur. Heart J., 38, 1764-1774.

Sörmann, J. et al. (2022). "Gain-of-function mutations in KCNK3 cause a developmental disorder with sleep apnea." Nat Genet 54, 1534-1543.

Trapp et al. (2008). "A Role for TASK-1 (KCNK3) Channels in the Chemosensory Control of Breathing," J. Neurosci. 28: 8844-8850.

Veale, E.L. et al. (2014). "Recovery of current through mutated TASK3 potassium channels underlying Birk Barel Syndrome." Mol. Pharmacol. 2014, 85, 397-407.

Wiedmann, F. et al. (2020). "The Experimental TASK-1 Potassium Channel Inhibitor A293 Can Be Employed for Rhythm Control of Persistent Atrial Fibrillation in a Translational Large Animal Model." Front. Physiol. 11, 1-13.

Wiedmann, F. et al. (2022). "MicroRNAs Regulate TASK-1 and Are Linked to Myocardial Dilatation in Atrial Fibrillation." J. Am. Heart Assoc. 11, 1-24.

Wiedmann, F. et al. (2022). "Treatment of atrial fibrillation with doxapram: TASK-1 potassium channel inhibition as a novel pharmacological strategy." Cardiovasc. Res. 118, 1728-1741.

Zhang C. et al. (2007). "Relationship between TWIK-related acid-sensitive K+ channel-1 and TWIK-related acid-sensitive K+ channel-3 expression and the occurrence of central sleep apnea: experiment with rats." Natl Med J China. 87(41):2929-2931.

DIAZABICYCLIC SUBSTITUTED IMIDAZOPYRIMIDINES AND THEIR USE FOR THE TREATMENT OF BREATHING DISORDERS

CROSS REFERENCE TO RELATED APPLICATIONS

This application is a divisional of U.S. application Ser. No. 16/622,233, which adopts the International Filing Date of Jun. 7, 2018, which is a national stage application under 35 U.S.C. § 371 of International Application No. PCT/EP2018/064977, filed internationally on Jun. 7, 2018, which claims the benefit of priority to European Application Nos. 17176046.5, filed Jun. 14, 2017, and 17193252.8, filed Sep. 26, 2017.

The present application relates to novel diazabicyclically substituted imidazo[1,2-a]pyrimidine derivatives, to processes for their preparation, to their use alone or in combinations for the treatment and/or prevention of diseases, and to their use for preparing medicaments for the treatment and/or prevention of diseases, in particular for treatment and/or prevention of respiratory disorders including sleep-related respiratory disorders such as obstructive sleep apnoeas and central sleep apnoeas and snoring.

Potassium channels are virtually ubiquitous membrane proteins which are involved in a large number of different physiological processes. This also includes the regulation of the membrane potential and the electric excitability of neurons and muscle cells. Potassium channels are divided into three major groups which differ in the number of transmembrane domains (2, 4 or 6). The group of potassium channels where two pore-forming domains are flanked by four transmembrane domains is referred to as K2P channels. Functionally, the K2P channels mediate, substantially time- and voltage-independently, $K^+$ background currents, and their contribution to the maintenance of the resting membrane potential is crucial. The family of the K2P channels includes 15 members which are divided into six subfamilies, based on similarities in sequence, structure and function: TWIK, TREK, TASK, TALK, THIK and TRESK.

Of particular interest are TASK-1 (KCNK3 or K2P3.1) and TASK-3 (KCNK9 or K2P9.1) of the TASK (TWIK-related acid-sensitive $K^+$ channel) subfamily. Functionally, these channels are characterized in that, during maintenance of voltage-independent kinetics, they have "leak" or "background" currents flowing through them, and they respond to numerous physiological and pathological influences by increasing or decreasing their activity. Characteristic of TASK channels is the sensitive reaction to a change in extracellular pH: the channels are inhibited at acidic pH and activated at alkaline pH.

TASK-1 is expressed mainly in the central nervous system and in the cardiovascular system. Relevant expression of TASK-1 was demonstrated in the brain, in spinal ganglia, in motoneurons of the Nervus hypoglossus and Nervus trigeminus, in the heart, Glomus caroticum, the pulmonary artery, aorta, lung, pancreas, placenta, uterus, kidney, adrenal gland, small intestine and stomach, and also on T lymphocytes. TASK-3 is expressed mainly in the central nervous system. Relevant expression of TASK-3 was demonstrated in the brain, in motoneurons of the Nervus hypoglossus and Nervus trigeminus and in neuroepithelial cells of the Glomus caroticum and the lung, and also on T lymphocytes. A lower expression is found in the heart, stomach, testicular tissue and adrenal gland.

TASK-1 and TASK-3 channels play a role in respiratory regulation. Both channels are expressed in the respiratory neurons of the respiratory centre in the brain stem, inter alia in neurons which generate the respiratory rhythm (ventral respiratory group with pre-Bötzinger complex), and in the noradrenergic Locus caeruleus, and also in serotonergic neurons of the raphe nuclei. Owing to the pH dependency, here the TASK channels have the function of a sensor which translates changes in extracellular pH into corresponding cellular signals [Bayliss et al., *Pflugers Arch.* 467, 917-929 (2015)]. TASK-1 and TASK-3 are also expressed in the Glomus caroticum, a peripheral chemoreceptor which measures pH, $O_2$ and $CO_2$ content of the blood and transmits signals to the respiratory centre in the brain stem to regulate respiration. It was shown that TASK-1 knock-out mice have a reduced ventilatory response (increase of respiratory rate and tidal volume) to hypoxia and normoxic hypercapnia [Trapp et al., *J. Neurosci.* 28, 8844-8850 (2008)]. Furthermore, TASK-1 and TASK-3 channels were demonstrated in motoneurons of the Nervus hypoglossus, the XIIth cranial nerve, which has an important role in keeping the upper airways open [Berg et al., *J. Neurosci.* 24, 6693-6702 (2004)].

In a sleep apnoea model in the anaesthetized pig, intranasal administration of a potassium channel blocker which blocks the TASK-1 channel in the nanomolar range led to inhibition of collapsibility of the pharyngeal respiratory musculature and sensitization of the negative pressure reflex of the upper airways. It is assumed that intranasal administration of the potassium channel blocker depolarizes mechanoreceptors in the upper airways and, via activation of the negative pressure reflex, leads to increased activity of the musculature of the upper airways, thus stabilizing the upper airways and preventing collapse. By virtue of this stabilization of the upper airways, the TASK channel blockade may be of great importance for obstructive sleep apnoea and also for snoring [Wirth et al., *Sleep* 36, 699-708 (2013); Kiper et al., *Pflugers Arch.* 467, 1081-1090 (2015)].

Obstructive sleep apnoea (OSA) is a sleep-related respiratory disorder which is characterized by repeat episodes of obstruction of the upper airways. When breathing in, the patency of the upper airways is ensured by the interaction of two opposite forces. The dilative effects of the musculature of the upper airways counteract the negative intraluminal pressure, which constricts the lumen. The active contraction of the diaphragm and the other auxiliary respiratory muscles generates a negative pressure in the airways, thus constituting the driving force for breathing. The stability of the upper airways is substantially determined by the coordination and contraction property of the dilating muscles of the upper airways.

The Musculus genioglossus plays a decisive role in the pathogenesis of obstructive sleep apnoea. The activity of the Musculus genioglossus increases with decreasing pressure in the pharynx in the sense of a dilative compensation mechanism. Innervated by the Nervus hypoglossus, it drives the tongue forward and downward, thus widening the pharyngeal airway [Verse et al., *Somnologie* 3, 14-20 (1999)]. Tensioning of the dilating muscles of the upper airways is modulated inter alia via mechanoreceptors/stretch receptors in the nasal cavity/pharynx [Bouillette et al., *J. Appl. Physiol. Respir. Environ. Exerc. Physiol.* 46, 772-779 (1979)]. In sleeping patients suffering from serious sleep apnoea, under local anaesthesia of the upper airway an additional reduction of the activity of the Musculus genioglossus can be observed [Berry et al., *Am. J. Respir. Crit. Care Med.* 156, 127-132 (1997)]. Patients suffering from obstructive sleep apnoea have high mortality and morbidity as a result of cardiovascular disorders such as hypertension, myocardial infarction and stroke [Vrints et al., *Acta Clin. Belg.* 68, 169-178 (2013)].

In the case of central sleep apnoea, owing to impaired brain function and impaired respiratory regulation there are episodic inhibitions of the respiratory drive. Central respiratory disorders result in mechanical respiratory arrests, i.e. during these episodes there is no breathing activity; temporarily, all respiratory muscles including the diaphragm are at rest. In the case of central sleep apnoea, there is no obstruction of the upper airways.

In the case of primary snoring, there is likewise no obstruction of the upper airways. However, owing to the constriction of the upper airways, the flow rate of the air that is inhaled and exhaled increases. This, combined with the relaxed musculature, causes the soft tissues of the oral cavity and the pharynx to flutter in the stream of air. This gentle vibration then generates the typical snoring noises.

Obstructive snoring (upper airway resistance syndrome, heavy snoring, hypopnoea syndrome) is caused by repeat partial obstruction of the upper airways during sleep. This results in an increased airway resistance and thus in an increase in work of breathing with considerable fluctuations in intrathoracic pressure. During inspiration, the negative intrathoracic pressure may reach values similar to those that are encountered as a result of complete airway obstruction during obstructive sleep apnoea. The pathophysiological consequences for heart, circulation and sleep quality correspond to those of obstructive sleep apnoea. As in obstructive sleep apnoea, the pathogenesis is assumed to be an impaired reflex mechanism of the pharynx-dilating muscles during inspiration when sleeping. Frequently, obstructive snoring is the preliminary stage of obstructive sleep apnoea [Hollandt et al., *HNO* 48, 628-634 (2000)].

In addition, TASK channels also appear to play a role in the apoptosis of neurons. In the animal model of myelin oligodendrocyte glycoprotein (MOG)-induced autoimmune encephalomyelitis, an animal model of multiple sclerosis, TASK-1 knock-out mice showed reduced neuronal degeneration. By preventing neuronal apoptosis, inhibition of TASK channels appears to act neuroprotectively, and may thus be of interest for the treatment of neurodegenerative disorders [Bittner et al., *Brain* 132, 2501-2516 (2009)].

Furthermore, it has been described that T lymphocytes express TASK-1 and TASK-3 channels and that inhibition of these channels leads to reduced cytokine production and proliferation after stimulation of T lymphocytes. The selective inhibition of TASK channels on T lymphocytes improved the course of the disease in an animal model of multiple sclerosis. The blockade of TASK channels may therefore also be of importance for treatment of autoimmune disorders [Meuth et al., *J. Biol. Chem.* 283, 14559-14579 (2008)].

TASK-1 and TASK-3 are also expressed in the heart [Rinne et al., *J. Mol. Cell. Cardiol.* 81, 71-80 (2015)]. Since TASK-1 is expressed particularly strongly in the nervous stimuli conduction system and in the atrium, this channel may have a role in disrupting stimuli conduction or triggering supraventricular arrhythmias. In the heart, TASK-1 appears to contribute to a background current which for its part contributes to maintenance of the resting potential, to action potential duration and to repolarization [Kim et al., *Am. J. Physiol.* 277, H1669-1678 (1999)]. Using human heart muscle cells, it was shown that blockade of the TASK-1 ion current results in a longer action potential [Limberg et al., *Cell. Physiol. Biochem.* 28, 613-624 (2011)]. Furthermore, for TASK-1 knock-out mice a prolonged QT time was demonstrated [Decher et al., *Cell. Physiol. Biochem.* 28, 77-86 (2011)]. Inhibition of TASK channels may therefore be of importance for the treatment of cardiac arrhythmias, in particular atrial fibrillation.

In certain vessels, TASK channels also appear to play a role in the regulation of the vascular tone. A relevant expression of TASK-1 was noticed in smooth muscles of pulmonary and mesenteric arteries. In studies on smooth muscle cells of human pulmonary arteries, it was shown that TASK-1 plays a role in the regulation of the pulmonary vascular tone. TASK-1 may be involved in hypoxic and acidosis-induced pulmonary vasoconstriction [Tang et al., *Am. J. Respir. Cell. Mol. Biol.* 41, 476-483 (2009)].

In glomerulosa cells of the adrenal cortex, TASK-1 plays a role in potassium conductivity [Czirjak et al., *Mol. Endocrinol.* 14, 863-874 (2000)].

Possibly, TASK channels also play an important role in apoptosis and tumorigenesis. In breast cancer, colon cancer and lung cancer biopsies and also in metastasizing prostate cancer and in melanoma cells, TASK-3 has been found to be strongly overexpressed [Mu et al., *Cancer Cell* 3, 297-302 (2003); Kim et al., *APMIS* 112, 588-594 (2004); Pocsai et al., *Cell. Mol. Life Sci.* 63, 2364-2376 (2006)]. A point mutation at the TASK-3 channel, which switches off the channel function, simultaneously cancels the tumour-forming action (proliferation, tumour growth, apoptosis resistance) [Mu et al., *Cancer Cell* 3, 297-302 (2003)]. Overexpression of TASK-3 and TASK-1 in a murine fibroblast cell line (C8 cells) inhibits intracellular apoptosis routes [Liu et al., *Brain Res.* 1031, 164-173 (2005)]. Accordingly, the blockade of TASK channels may also be relevant for the treatment of various neoplastic disorders.

Therefore, it is an object of the present invention to provide novel substances which act as potent and selective blockers of TASK-1 and TASK-3 channels and, as such, are suitable in particular for the treatment and/or prevention of respiratory disorders including sleep-related respiratory disorders such as obstructive and central sleep apnoeas and snoring, and also other disorders.

US 2002/0022624-A1 describes various azaindole derivatives including imidazo[1,2-a]pyridines as substance P antagonists for the treatment of CNS disorders. WO 02/02557-A2 and WO 2009/143156-A2 disclose 2-phenylimidazo[1,2-a]pyridine derivatives which, as modulators of $GABA_A$ receptors, are likewise suitable for treating CNS disorders. WO 2011/113606-A1 and WO 2012/143796-A2 disclose bicyclic imidazole derivatives suitable for the treatment of bacterial infections and inflammatory disorders. EP 2671582-A1 discloses further bicyclic imidazole derivatives and options for their therapeutic use as inhibitors of T type calcium channels. WO 2012/130322-A1 describes 2,6-diaryl-3-(piperazinomethyl)imidazo[1,2-a]pyridine derivatives which, by virtue of their HIF-1 inhibiting activity, are suitable in particular for the treatment of inflammatory and hyperproliferative disorders. WO 2014/187922-A1 discloses various 2-phenyl-3-(heterocyclomethyl)imidazo[1,2-a]pyridine and -imidazo[1,2-a]pyrazine derivatives which can be employed as inhibitors of glucose transporters (GLUT) for treating inflammatory, proliferative, metabolic, neurological and/or autoimmune disorders. WO 2015/144605-A1 and WO 2017/050732-A1, inter alia, describe acylated bicyclic amine compounds suitable as inhibitors of autotaxin and of lysophosphatidic acid production for the treatment of various disorders. WO 2016/084866-A1, WO 2016/085783-A1 and WO 2016/088813-A1 disclose acylated diazabicyclic compounds which, by virtue of their antagonistic action on orexin receptors, can be used for treating neurodegenerative, neurological and psychiatric disorders, mental disorders and eating and sleep disorders, in particular sleeplessness.

Furthermore, the compound ethyl 4-[(2-phenylimidazo[1,2-a]pyrimidin-3-yl)methyl]piperazin-1-carboxylate [CAS Registry No. 1783141-19-4] has been indexed by Chemical Abstracts as "Chemical Library" substance without literature reference; a medicinal-therapeutic application of this compound has hitherto not been described.

The present invention provides compounds of the general formula (I)

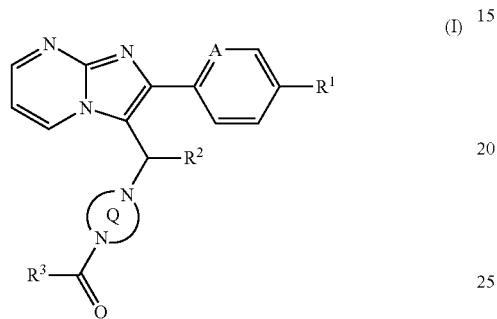

(I)

in which the ring Q represents a diazaheterobicyclic system of the formula

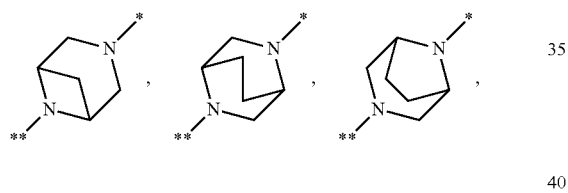

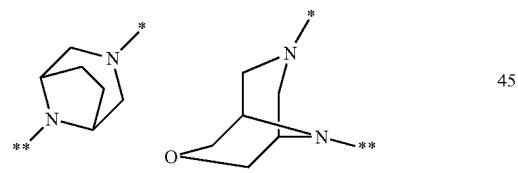

in which * denotes the bond to the adjacent $CHR^2$ group and ** the bond to the carbonyl group, A represents CH or N, $R^1$ represents halogen, cyano, cyclopropyl or cyclobutyl
  where $(C_1-C_4)$-alkyl may be up to trisubstituted by fluorine and cyclopropyl and cyclobutyl may be up to disubstituted by fluorine, $R^2$ represents hydrogen or methyl, and $R^3$ represents $(C_4-C_6)$-cycloalkyl in which a ring $CH_2$ group may be replaced by —O—, or $R^3$ represents a phenyl group of the formula (a), a pyridyl group of the formula (b) or (c) or an azole group of the formula (d), (e) or (f)

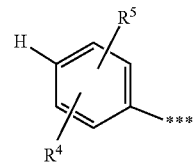

(a)

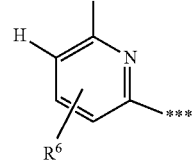

(b)

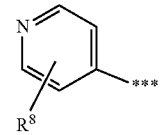

(c)

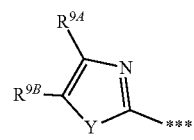

(d)

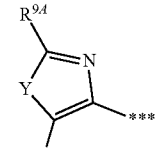

(e)

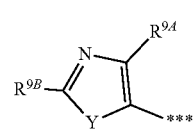

(f)

in which *** marks the bond to the adjacent carbonyl group and $R^4$ represents hydrogen, fluorine, chlorine, bromine or methyl, $R^5$ represents hydrogen, fluorine, chlorine, bromine, cyano, $(C_1-C_3)$-alkyl or $(C_1-C_3)$-alkoxy,
  where $(C_1-C_3)$-alkyl and $(C_1-C_3)$-alkoxy may each be up to trisubstituted by fluorine, $R^6$ represents hydrogen, fluorine, chlorine, bromine or methyl, $R^7$ represents hydrogen, $(C_1-C_3)$-alkoxy, cyclobutyloxy, oxetan-3-yloxy, tetrahydrofuran-3-yloxy, tetrahydro-2H-pyran-4-yloxy, mono-$(C_1-C_3)$-alkylamino, di-$(C_1-C_3)$-alkylamino or $(C_1-C_3)$-alkylsulfanyl,
  where $(C_1-C_3)$-alkoxy may be up to trisubstituted by fluorine, $R^8$ represents hydrogen, fluorine, chlorine, bromine, $(C_1-C_3)$-alkyl or $(C_1-C_3)$-alkoxy, $R^{9A}$ and $R^{9B}$ are identical or different and independently of one another represent hydrogen, fluorine, chlorine, bromine, $(C_1-C_3)$-alkyl, cyclopropyl or $(C_1-C_3)$-alkoxy
  where $(C_1-C_3)$-alkyl and $(C_1-C_3)$-alkoxy may each be up to trisubstituted by fluorine, and Y represents O or S, or R³ represents an —OR¹⁰ or —NR¹¹R¹² group in which R¹⁰ represents $(C_1-C_6)$-alkyl, $(C_4-C_6)$-cycloalkyl or $[(C_3-C_6)$-cycloalkyl]methyl, R¹¹ represents hydrogen or $(C_1-C_3)$-alkyl and R¹² represents $(C_1-C_6)$-alkyl, $(C_3-C_6)$-cycloalkyl, phenyl or benzyl, where $(C_1-C_6)$-alkyl may be up to trisubstituted by fluorine, and where phenyl and the phenyl group in benzyl may be up to trisubstituted by identical or different radicals selected from the group consisting of fluorine, chlorine, methyl, ethyl, trifluoromethyl, methoxy, ethoxy, trifluoromethoxy and (trifluoromethyl)sulfanyl, or R¹¹ and R¹² are attached to one another and, together with the nitrogen atom to which they are bonded, form a pyrrolidine, piperidine, morpholine or thiomorpholine ring, and the salts, solvates and solvates of the salts thereof.

Inventive compounds are the compounds of the formula (I) and the salts, solvates and solvates of the salts thereof, the compounds of the formulae (I-A), (I-B), (I-C), (I-D) and (I-E) cited hereinafter that are encompassed by formula (I) and the salts, solvates and solvates of the salts thereof, and the compounds cited hereinafter as working examples that are encompassed by formula (I) and the salts, solvates and solvates of the salts thereof, if the compounds cited hereinafter that are encompassed by formula (I) are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for the isolation, purification or storage of the compounds of the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof. The stereoisomerically homogeneous constituents can be isolated from such mixtures of enantiomers and/or diastereomers in a known manner; chromatography processes are preferably employed for the purpose, especially HPLC chromatography on chiral or achiral separation phases. In the case of chiral amines as intermediates or end products, separation is alternatively also possible via diastereomeric salts using enantiomerically pure carboxylic acids.

If the compounds of the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass from the atomic mass which usually or predominantly occurs in nature. Examples of isotopes which can be incorporated into a compound according to the invention are those of hydrogen, carbon, nitrogen, oxygen, phosphorus, sulfur, fluorine, chlorine, bromine and iodine, such as ²H (deuterium), ³H (tritium), ¹³C, ¹⁴C, ¹⁵N, ¹⁷O, ¹⁸O, ³²P, ³³P, ³³S, ³⁴S, ³⁵S, ³⁶S, ¹⁸F, ³⁶Cl, ⁸²Br, ¹²³I, ¹²⁴I, ¹²⁹I and ¹³¹I. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labelled with ³H or ¹⁴C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. Isotopic variants of the compounds of the invention can be prepared by commonly used processes known to those skilled in the art, for example by the methods described further down and the procedures described in the working examples, by using corresponding isotopic modifications of the respective reagents and/or starting compounds.

The present invention additionally also encompasses prodrugs of the compounds according to the invention. The term "prodrugs" refers here to compounds which may themselves be biologically active or inactive, but are converted while present in the body, for example by a metabolic or hydrolytic route, to compounds of the invention.

In the context of the present invention, unless specified otherwise, the substituents and radicals are defined as follows:

In the context of the invention, $(C_1-C_6)$-alkyl is a straight-chain or branched alkyl radical having 1 to 6 carbon atoms. Examples include: methyl, ethyl, n-propyl, isopropyl, n-butyl, isobutyl, sec-butyl, tert-butyl, n-pentyl, 2-pentyl, 3-pentyl, neopentyl, n-hexyl, 2-hexyl and 3-hexyl.

In the context of the invention, $(C_1-C_4)$-alkyl is a straight-chain or branched alkyl radical having 1 to 4 carbon atoms. Examples include: methyl, ethyl, n-propyl, isopropyl, n-butyl, isobutyl, sec-butyl and tert-butyl.

In the context of the invention, $(C_1-C_3)$-alkyl is a straight-chain or branched alkyl radical having 1 to 3 carbon atoms. Examples include: methyl, ethyl, n-propyl and isopropyl.

(C₁-C₃)-Alkoxy in the context of the invention is a straight-chain or branched alkoxy radical having 1 to 3 carbon atoms. Examples include: methoxy, ethoxy, n-propoxy and isopropoxy.

Mono-(C₁-C₃)-alkylamino in the context of the invention is an amino group having a straight-chain or branched alkyl substituent having 1 to 3 carbon atoms. Examples include: methylamino, ethylamino, n-propylamino and isopropylamino.

Di-(C₁-C₃)-alkylamino in the context of the invention is an amino group having two identical or different straight-chain or branched alkyl substituents each having 1 to 3 carbon atoms. Examples include: N,N-dimethylamino, N,N-diethylamino, N-ethyl-N-methylamino, N-methyl-N-n-propylamino, N-isopropyl-N-methylamino, N,N-di-n-propylamino, N-isopropyl-N-n-propylamino and N,N-diisopropylamino.

(C₁-C₃)-Alkylsulfanyl [also referred to as (C₁-C₃)-alkylthio] in the context of the invention is a straight-chain or branched alkyl radical having 1 to 3 carbon atoms which is attached to the remainder of the molecule via a sulfur atom. Examples include: methylsulfanyl, ethylsulfanyl, n-propylsulfanyl and isopropylsulfanyl.

(C₃-C₆)-Cycloalkyl in the context of the invention is a monocyclic saturated cycloalkyl group having 3 to 6 ring carbon atoms. Examples include: cyclopropyl, cyclobutyl, cyclopentyl and cyclohexyl.

(C₄-C₆)-Cycloalkyl in the context of the invention is a monocyclic saturated cycloalkyl group having 4 to 6 carbon atoms. Examples include: cyclobutyl, cyclopentyl and cyclohexyl.

Halogen in the context of the invention includes fluorine, chlorine, bromine and iodine. Preference is given to fluorine, chlorine or bromine.

In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred. Particular preference is given to substitution by one substituent.

Preference is given in the context of the present invention to compounds of the formula (I) in which
the ring Q represents a diazaheterobicyclic system of the formula

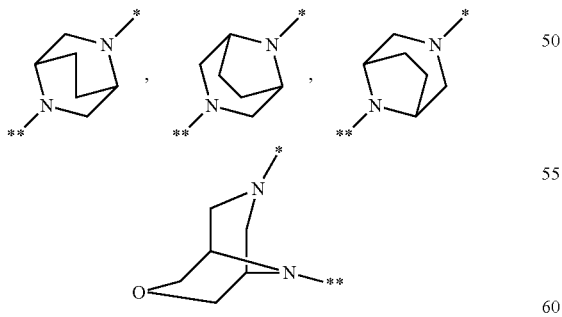

in which * denotes the bond to the adjacent CHR² group and ** the bond to the carbonyl group,
A represents CH,
R¹ represents fluorine, chlorine, bromine, methyl, isopropyl, tert-butyl, cyclopropyl or cyclobutyl,
R² represents hydrogen,
and
R³ represents cyclobutyl, cyclopentyl or cyclohexyl
or
R³ represents a phenyl group of the formula (a), a pyridyl group of the formula (b) or an azole group of the formula (d), (e) or (f)

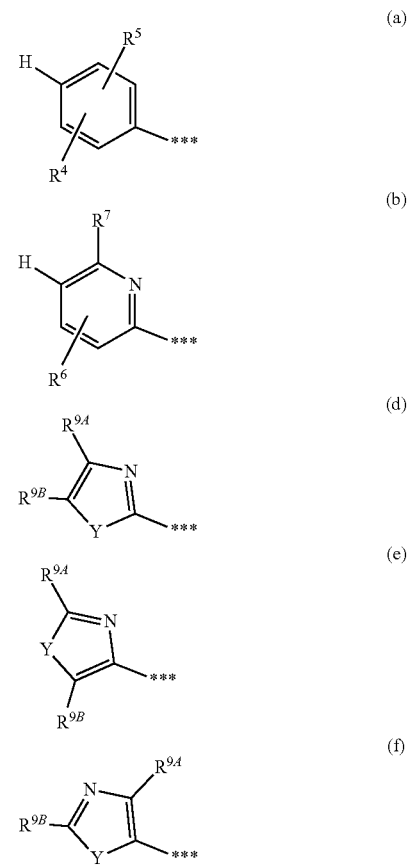

in which *** marks the bond to the adjacent carbonyl group and
R⁴ represents hydrogen, fluorine or chlorine,
R⁵ represents fluorine, chlorine, cyano, (C₁-C₃)-alkyl, (C₁-C₃)-alkoxy or trifluoromethoxy,
R⁶ represents hydrogen, fluorine, chlorine, bromine or methyl,
R⁷ represents (C₁-C₃)-alkoxy, cyclobutyloxy or (C₁-C₃)-alkylsulfanyl,
where (C₁-C₃)-alkoxy may be up to trisubstituted by fluorine,
R⁹ᴬ and R⁹ᴮ are identical or different and independently of one another represent hydrogen, chlorine, bromine, (C₁-C₃)-alkyl or cyclopropyl,
where (C₁-C₃)-alkyl may be up to trisubstituted by fluorine,
and
Y represents O or S,
and the salts, solvates and solvates of the salts thereof.

A particular embodiment of the present invention relates to compounds of the formula (I) in which
the ring Q represents a diazaheterobicyclic system of the formula

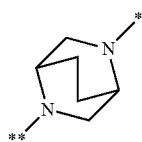

in which * denotes the bond to the adjacent CHR² group and ** the bond to the carbonyl group, and the salts, solvates and solvates of the salts thereof.

A further particular embodiment of the present invention relates to compounds of the formula (I) in which the ring Q represents a diazaheterobicyclic system of the formula

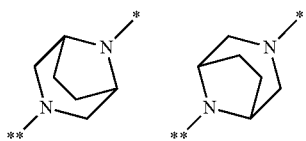

in which * denotes the bond to the adjacent CHR² group and ** the bond to the carbonyl group, and the salts, solvates and solvates of the salts thereof.

A further particular embodiment of the present invention relates to compounds of the formula (I) in which the ring Q represents a diazaheterobicyclic system of the formula

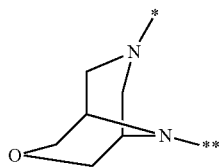

in which * denotes the bond to the adjacent CHR² group and ** the bond to the carbonyl group, and the salts, solvates and solvates of the salts thereof.

A further particular embodiment of the present invention relates to compounds of the formula (I) in which A represents CH, and the salts, solvates and solvates of the salts thereof.

A further particular embodiment of the present invention relates to compounds of the formula (I) in which R¹ represents chlorine, bromine, isopropyl or cyclopropyl, and the salts, solvates and solvates of the salts thereof.

A further particular embodiment of the present invention relates to compounds of the formula (I) in which R² represents hydrogen, and the salts, solvates and solvates of the salts thereof.

A further particular embodiment of the present invention relates to compounds of the formula (I) in which R³ represents cyclopentyl or cyclohexyl, and the salts, solvates and solvates of the salts thereof.

A further particular embodiment of the present invention relates to compounds of the formula (I) in which R³ represents a phenyl group of the formula (a)

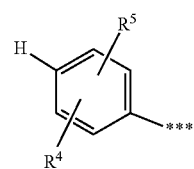

(a)

in which *** marks the bond to the adjacent carbonyl group,

R⁴ represents hydrogen, fluorine or chlorine and

R⁵ represents fluorine, chlorine, $(C_1-C_3)$-alkyl or $(C_1-C_3)$-alkoxy, and the salts, solvates and solvates of the salts thereof.

A further particular embodiment of the present invention relates to compounds of the formula (I) in which R³ represents a pyridyl group of the formula (b)

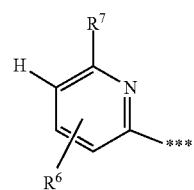

(b)

in which *** marks the bond to the adjacent carbonyl group,

R⁶ represents hydrogen, fluorine, chlorine, bromine or methyl and

R⁷ represents $(C_1-C_3)$-alkoxy, cyclobutyloxy or $(C_1-C_3)$-alkylsulfanyl, where $(C_1-C_3)$-alkoxy may be up to trisubstituted by fluorine, and the salts, solvates and solvates of the salts thereof.

A further particular embodiment of the present invention relates to compounds of the formula (I) in which R³ represents an azole group of the formula (d), (e) or (f)

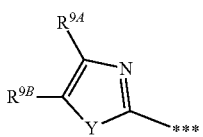

(d)

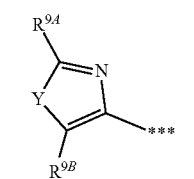

(e)

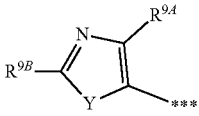

(f)

in which *** marks the bond to the adjacent carbonyl group, $R^{9A}$ and $R^{9B}$ are identical or different and independently of one another represent hydrogen, chlorine, bromine, $(C_1-C_3)$-alkyl or cyclopropyl, where $(C_1-C_3)$-alkyl may be up to trisubstituted by fluorine, and Y represents O or S, and the salts, solvates and solvates of the salts thereof.

In the context of the present invention, particular preference is given to compounds of the formula (I) in which the ring Q represents a diazaheterobicyclic system of the formula

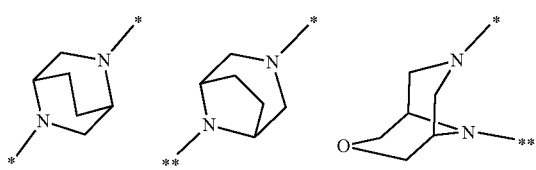

in which * denotes the bond to the adjacent $CHR^2$ group and ** the bond to the carbonyl group, A represents CH, $R^1$ represents chlorine, bromine, isopropyl or cyclopropyl, $R^2$ represents hydrogen, and $R^3$ represents cyclopentyl or cyclohexyl, or $R^3$ represents a phenyl group of the formula (a), a pyridyl group of the formula (b) or an azole group of the formula (d), (e) or (f)

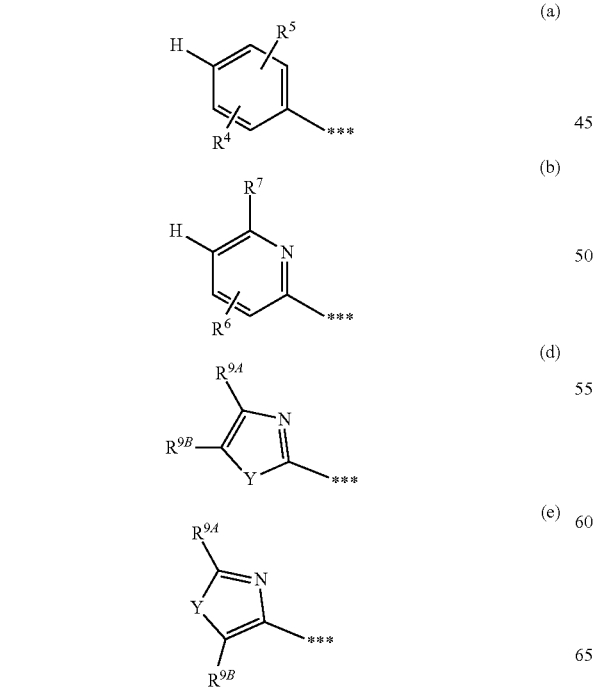

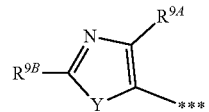

in which *** marks the bond to the adjacent carbonyl group and $R^4$ represents hydrogen, fluorine or chlorine, $R^5$ represents fluorine, chlorine, methyl, isopropyl, methoxy or ethoxy, $R^6$ represents hydrogen, fluorine, chlorine, bromine or methyl, $R^7$ represents methoxy, difluoromethoxy, trifluoromethoxy, isopropoxy, cyclobutyloxy or methylsulfanyl, $R^{9A}$ and $R^{9B}$ are identical or different and independently of one another represent hydrogen, methyl, trifluoromethyl, ethyl, isopropyl or cyclopropyl, and Y represents O or S, and the salts, solvates and solvates of the salts thereof.

The individual radical definitions specified in the respective combinations or preferred combinations of radicals are, independently of the respective combinations of the radicals specified, also replaced as desired by radical definitions of other combinations. Particular preference is given to combinations of two or more of the abovementioned preferred ranges.

The invention furthermore provides a process for preparing compounds of the formula (I) according to the invention in which the radical $R^2$ represents hydrogen, characterized in that a compound of the formula (II)

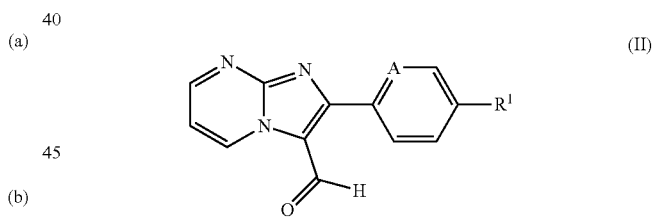

in which A and $R^1$ have the meanings given above is reacted in the presence of a suitable reducing agent either

[A] with a compound of the formula (III)

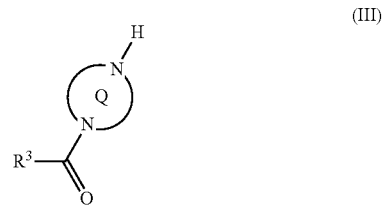

in which $R^3$ and the ring Q have the meanings given above to give a compound of the formula (I-A)

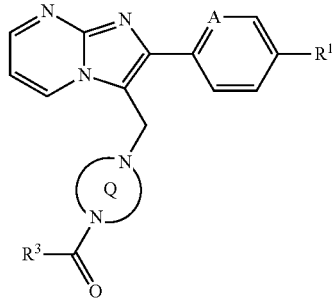
(I-A)

in which A, R¹, R³ and the ring Q have the meanings given above or

[B] with a protected diazaheterobicyclic system of the formula (IV)

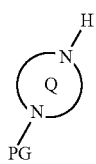
(IV)

in which the ring Q has the meaning given above and

PG represents a suitable amino protecting group, for example tert-butoxycarbonyl, benzyloxycarbonyl or (9H-fluoren-9-ylmethoxy)carbonyl at first to give a compound of the formula (V)

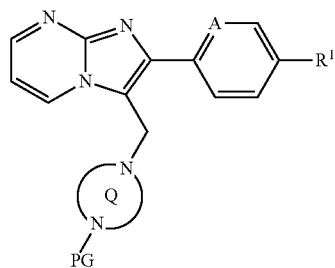
(V)

in which A, PG, R¹ and the ring Q have the meanings given above, then the protecting group PG is cleaved and the resulting compound of the formula (VI)

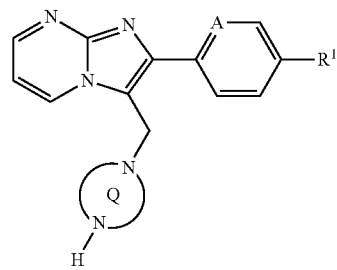
(VI)

in which A, R¹ and the ring Q have the meanings given above is then reacted, depending on the specific definition of the R³ radical,

[B-1] with a carboxylic acid of the formula (VII)

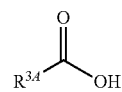
(VII)

in which $R^{3A}$ represents $(C_4-C_6)$-cycloalkyl in which a ring $CH_2$ group may be replaced by —O—, or is a phenyl group of the formula (a), a pyridyl group of the formula (b) or (c) or an azole group of the formula (d), (e) or (f), as described above, with activation of the carboxylic acid function in (VII), or is reacted with the corresponding acid chloride of the formula (VIII)

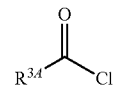
(VIII)

in which $R^{3A}$ has the meaning given above to give a compound of the formula (I-B)

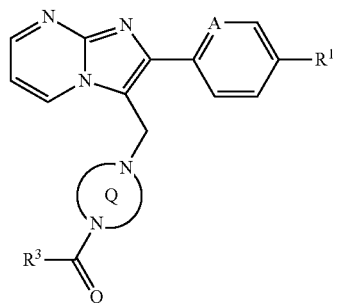
(I-B)

in which A, R¹, $R^{3A}$ and the ring Q have the meanings given above or

[B-2] with a chloroformate or carbamoyl chloride of the formula (IX)

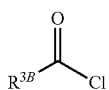
(IX)

in which
R³ᴮ represents the —OR¹⁰ or —NR¹¹ᴬR¹² group in which
R¹⁰ and R¹² have the meanings given above
and
R¹¹ᴬ has the definition of R¹¹ given above, but is not hydrogen,
to give a compound of the formula (I-C)

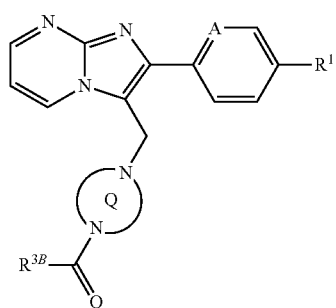
(I-C)

in which A, R¹, R³ᴮ and the ring Q have the meanings given above
or
[B-3] with an isocyanate of the formula (X)

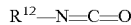
R¹²—N=C=O     (X)

in which R¹² has the meaning given above
to give a compound of the formula (I-D)

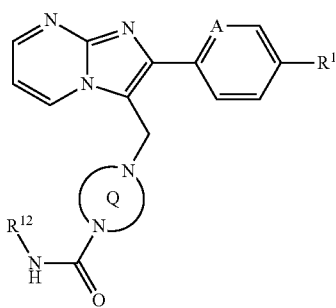
(I-D)

in which A, R¹, R¹² and the ring Q have the meanings given above
and the compounds of the formulae (I-A), (I-B), (I-C) and (I-D) thus obtained are optionally separated into their enantiomers and/or diastereomers and/or optionally converted with the appropriate (i) solvents and/or (ii) acids to the solvates, salts and/or solvates of the salts thereof.

Suitable reducing agents for the process steps [A] (II)+(III)→(I-A) and [B] (II)+(IV)→(V) [reductive aminations] for such purposes are customary alkali metal borohydrides such as sodium borohydride, sodium cyanoborohydride or sodium triacetoxyborohydride; preference is given to using sodium triacetoxyborohydride. The addition of an acid, such as acetic acid in particular, and/or of a dehydrating agent, for example molecular sieve or trimethyl orthoformate or triethyl orthoformate, may be advantageous in these reactions.

Suitable solvents for these reactions are especially alcohols such as methanol, ethanol, n-propanol or isopropanol, ethers such as diisopropyl ether, methyl tert-butyl ether, tetrahydrofuran, 1,4-dioxane or 1,2-dimethoxyethane, polar aprotic solvents such as acetonitrile or N,N-dimethylformamide (DMF) or mixtures of such solvents; preference is given to using tetrahydrofuran. The reactions are generally effected within a temperature range of 0° C. to +50° C.

The protecting group PG used in compound (IV) may be a standard amino protecting group, for example tert-butoxycarbonyl (Boc), benzyloxycarbonyl (Z) or (9H-fluoren-9-ylmethoxy)carbonyl (Fmoc); preference is given to using tert-butoxycarbonyl (Boc). The detachment of the protecting group in method step [B] (V)→(VI) is effected by known methods. Thus, the tert-butoxycarbonyl group is typically cleaved by treatment with a strong acid such as hydrogen chloride, hydrogen bromide or trifluoroacetic acid, in an inert solvent such as diethyl ether, 1,4-dioxane, dichloromethane or acetic acid. In the case of benzyloxycarbonyl as protecting group, this is preferably removed by hydrogenolysis in the presence of a suitable palladium catalyst such as palladium on activated carbon. The (9H-fluoren-9-ylmethoxy)carbonyl group is generally cleaved with the aid of a secondary amine base such as diethylamine or piperidine [see e.g. T. W. Greene and P. G. M. Wuts, *Protective Groups in Organic Synthesis*, Wiley, New York, 1999; P. J. Kocienski, *Protecting Groups*, 3ʳᵈ edition, Thieme, 2005].

Certain compounds of the formula (V), especially those in which PG is tert-butoxycarbonyl, likewise have significant inhibitory activity with respect to TASK-1 and/or TASK-3, and in this respect are also encompassed by the scope of definition of the present invention, i.e. the compounds of the formula (I).

The process step [B-1] (VI)+(VII)→(I-B) [amide formation] is conducted by known methods with the aid of a condensing or activating agent. Suitable agents of this kind are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, α-chlorenamines such as 1-chloro-N,N,2-trimethylprop-1-en-1-amine, 1,3,5-triazine derivatives such as 4-(4,6-dimethoxy-1,3,5-triazin-2-yl)-4-methylmorpholinium chloride, phosphorus compounds such as n-propanephosphonic anhydride (PPA), diethyl cyanophosphonate, diphenylphosphoryl azide (DPPA), bis(2-oxo-3-oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(1H-6-chlorobenzotriazol-1-yl)-1,1,3,3-tetramethyluronium tetrafluoroborate (TCTU), O-(benzotriazol-1-yl)-N,N,N',N'-tetramethyluronium hexafluorophosphate (HBTU) O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and also as base an alkali metal carbonate, for example sodium carbonate or potassium carbonate, or a tertiary amine base such as triethylamine, N,N-diisopropylethylamine, N-methylmorpholine (NMM), N-methylpiperidine (NMP), pyridine or 4-N,N-dimethylaminopyridine (DMAP). The condensing agent or activating agent used with preference is O-(7-azabenzotriazol-1-yl)-N,N,N',N'-tetramethyluronium hexafluorophosphate (HATU) in combination with N,N-diisopropylethylamine as base.

The alternative process via the carbonyl chloride (VIII) [(VI)+(VIII)→(I-B)] is generally effected in the presence of a base such as sodium carbonate, potassium carbonate, triethylamine, N,N-diisopropylethylamine, N-methylmorpholine (NMM), N-methylpiperidine (NMP), pyridine, 2,6-dimethylpyridine, 4-N,N-dimethylaminopyridine (DMAP), 1,5-diazabicyclo[4.3.0]non-5-ene (DBN) or 1,8-diazabicyclo[5.4.0]undec-7-ene (DBU); preference is given to using triethylamine or N,N-diisopropylethyl amine.

Suitable inert solvents for these amide-forming reactions are, for example, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP); it is also possible to use mixtures of such solvents. Preference is given to using dichloromethane, 1,2-dichloroethane, tetrahydrofuran, N,N-dimethylformamide or mixtures of these solvents. The reactions are generally conducted within a temperature range of from –20° C. to +60° C., preferably at from 0° C. to +40° C.

The process [B-2] (VI)+(IX)→(I-C) [formation of urethanes or substituted ureas] is conducted under similar reaction conditions with regard to solvent, addition of base and temperature as described above for the amide formation [B-1] (VI)+(VIII)→(I-B).

The reaction [B-3] (VI)+(X)→(I-D) is likewise effected in one of the above-listed inert solvents or solvent mixtures at a temperature in the range from 0° C. to +60° C.; the addition of a base in this reaction can optionally be dispensed with.

The amine compound (VI) can also be used in the process steps [B-1] (VI)+(VII) or (VIII)→(I-B), [B-2] (VI)+(IX)→(I-C) and [B-3] (VI)+(X)→(I-D) in the form of a salt, for example as hydrochloride or trifluoroacetate. In such a case, the conversion is effected in the presence of an appropriately increased amount of the respective auxiliary base used.

Compounds of the formula (I) according to the invention in which the radical $R^2$ represents methyl can be obtained by reacting the carbaldehyde of the formula (II) already mentioned above

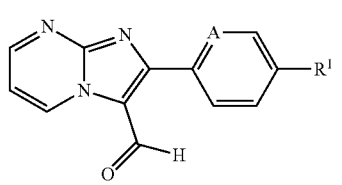

(II)

in which A and $R^1$ have the meanings given above initially with methylmagnesium bromide to give the secondary alcohol of the formula (XI)

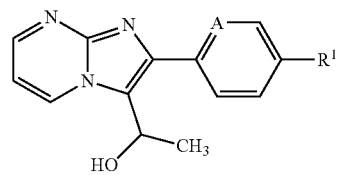

(XI)

in which A and $R^1$ have the meanings given above, then converting this with the aid of triphenylphosphine and carbon tetrabromide into the corresponding bromide of the formula (XII)

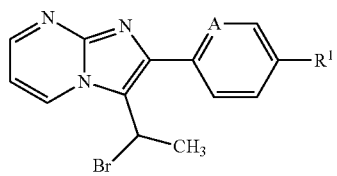

(XII)

in which A and $R^1$ have the meanings given above, subsequently reacting with a protected diazaheterobicyclic system of the formula (IV)

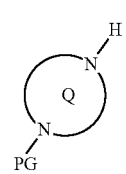

(IV)

in which the ring Q has the meaning given above and

PG represents a suitable amino protecting group, for example tert-butoxycarbonyl, benzyloxycarbonyl or (9H-fluoren-9-ylmethoxy)carbonyl to give a compound of the formula (XIII)

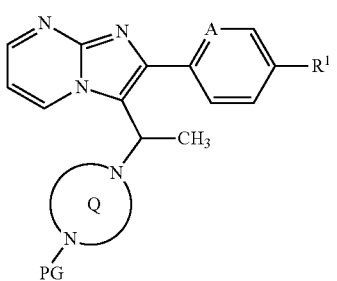

(XIII)

in which A, PG, $R^1$ and the ring Q have the meanings given above, thereafter cleaving the protecting group PG and then converting the resulting compound of the formula (XIV)

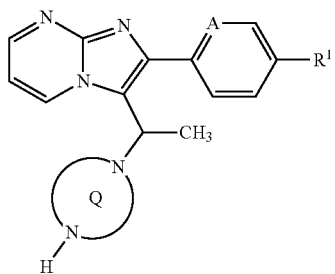

in which A, R¹ and the ring Q have the meanings given above depending on the specific meaning of the radical R³ according to one of the processes [B-1], [B-2] and [B-3] described above into the target compound of the formula (I-E)

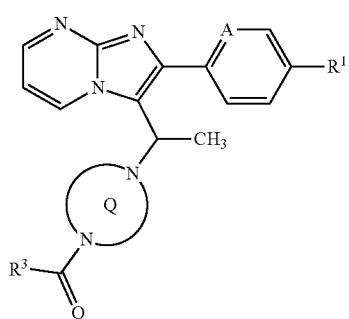

in which A, R¹, R³ and the ring Q have the meanings given above and optionally separating the latter into their enantiomers and/or diastereomers and/or optionally reacting them with the corresponding (i) solvents and/or (ii) acids to give solvates, salts and/or solvates of the salts thereof.

The conversion of the carbaldehyde (II) with methylmagnesium bromide into the secondary alcohol (XI) is typically carried out in an ethereal solvent such as diethyl ether, diisopropyl ether, methyl tert-butyl ether, tetrahydrofuran or a mixture thereof in a temperature range from −20° C. to +40° C. The subsequent conversion into the bromide (XII) is advantageously carried out under mild conditions using the reagent combination of triphenylphosphine and carbon tetrabromide in the presence of triethylamine as base ("Appel reaction"). The reaction is preferably carried out in dichloromethane as inert solvent in a temperature range from −10° C. to +30° C. For the subsequent reaction with the diazaheterobicyclic system (IV), the bromide (XII) is preferably not isolated beforehand but employed directly as crude product in a one-pot process with change of solvent. For this reaction (XII)+(IV)→(XIII), the solvent used is preferably acetonitrile, and the reaction generally takes place in a temperature range from +20° C. to +60° C.

The process steps (XIII)→(XIV) and (XIV)→(I-E) finally are carried out analogously to those described above for the processes [B] (V)→(VI) and [B-1], [B-2] or [B-3].

The processes described above can be conducted at atmospheric, elevated or reduced pressure (for example in the range from 0.5 to 5 bar); in general, the reactions are each carried out at atmospheric pressure.

Separation of the compounds of the invention into the corresponding enantiomers and/or diastereomers can, as appropriate, optionally also be carried out at the early stage of the compounds (III), (IV), (V) or (VI) and (XI), (XIII) or (XIV), respectively, converted further in separated form in accordance with the process steps described above. Such a separation of stereoisomers can be conducted by customary methods known to the person skilled in the art. In the context of the present invention, preference is given to using chromatographic methods on chiral or achiral separation phases; in the case of chiral amines as intermediates or end products, separation can alternatively be effected via diastereomeric salts with the aid of enantiomerically pure carboxylic acids.

For their part, the compounds of the formula (II) can be prepared by processes known from the literature by condensing 2-aminopyrimidine (XV)

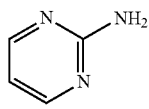

under the influence of a base with a compound of the formula (XVI)

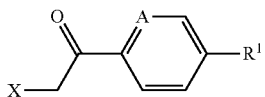

in which A and R¹ have the meanings given above and

X represents a suitable leaving group, for example chlorine, bromine or iodine to give an imidazo[1,2-a]pyrimidine derivative of the formula (XVII)

in which A and R¹ have the definitions given above and then formylating this with a mixture of N,N-dimethylformamide and phosphorus oxychloride to give (II).

The condensation reaction (XV)+(XVI)→(XVII) is typically conducted in an alcoholic solvent such as methanol, ethanol, n-propanol, isopropanol or n-butanol, in an ether such as diethyl ether, diisopropyl ether, methyl tert-butyl ether, tetrahydrofuran, 1,4-dioxane, 1,2-dimethoxyethane or bis(2-methoxyethyl) ether, in a dipolar aprotic solvent such as N,N-dimethylformamide (DMF), N,N'-dimethylpropyleneurea (DMPU) or N-methylpyrrolidinone (NMP), or else in water, at a temperature in the range from +50° C. to +150° C.; the solvent used is preferably ethanol or water.

Bases suitable for this reaction are in particular alkali metal bicarbonates or carbonates such as sodium bicarbonate or potassium bicarbonate or lithium carbonate, sodium carbonate, potassium carbonate or caesium carbonate, alkali metal hydroxides such as sodium hydroxide or potassium hydroxide, or else alumina; preference is given to using sodium bicarbonate or sodium hydroxide.

Optionally—if the reaction temperature is increased appropriately—the reaction can also be carried out without addition of a base.

The regioselective formylation (XVII)→(II) is carried out under the standard conditions of a Vilsmaier-Haack reaction by treatment of (XVII) with a preformed mixture of N,N-dimethylformamide and phosphorus oxychloride which is used in a large excess and simultaneously also serves as solvent. The reaction is generally carried out within a temperature range of from 0° C. to +100° C.

The compounds of the formulae (III), (IV), (VII), (VIII), (IX), (X), (XV) and (XVI) are either commercially available or described as such in the literature, or they can be prepared in a simple manner from other commercially available compounds by methods familiar to the person skilled in the art and known from the literature. Numerous detailed procedures and further literature references can also be found in the experimental section, in the section on the preparation of the starting compounds and intermediates.

The preparation of the compounds of the invention can be illustrated by way of example by the following reaction schemes:

Scheme 1

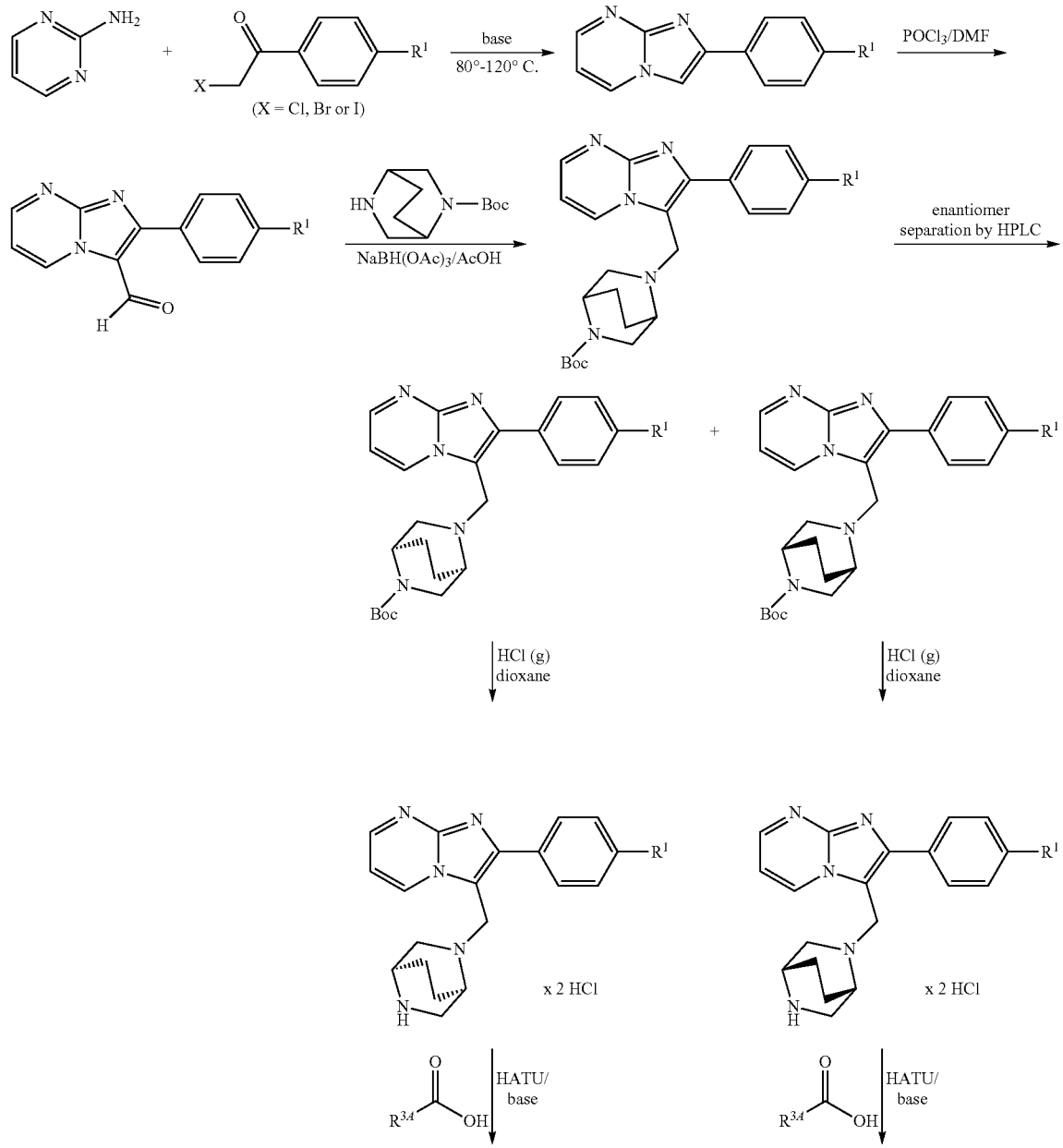

25 26
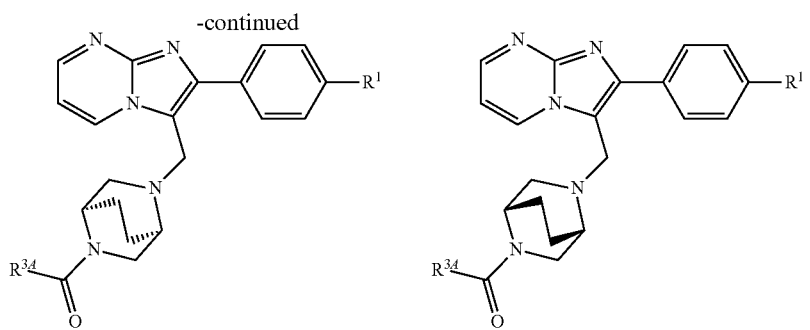
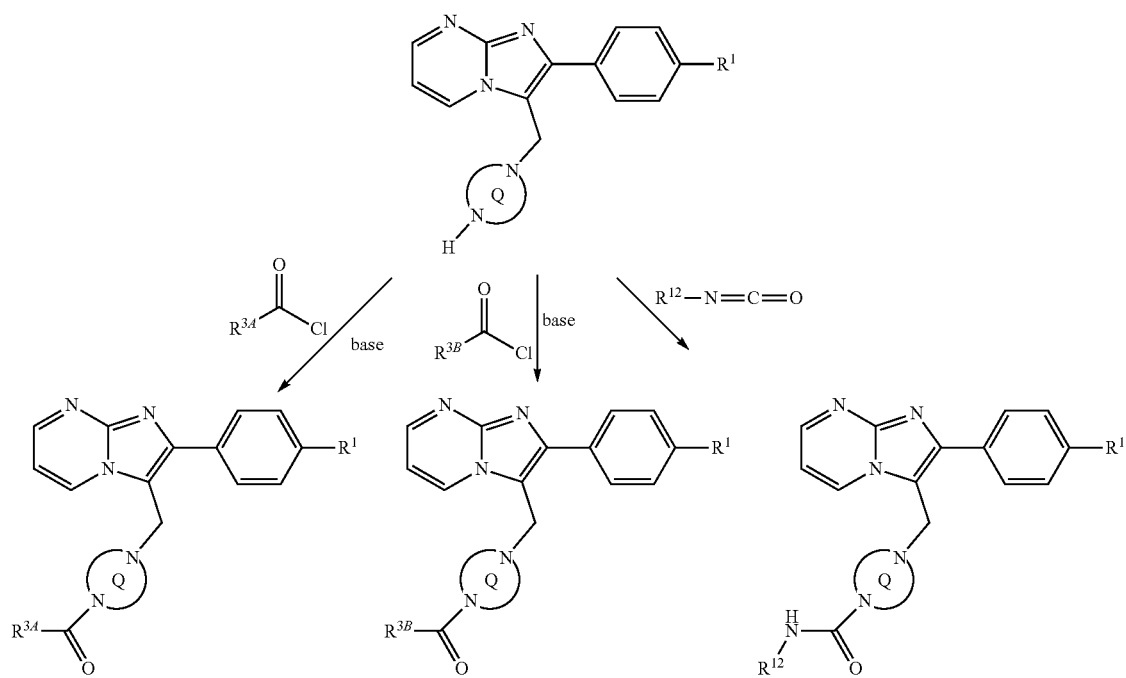
Scheme 2
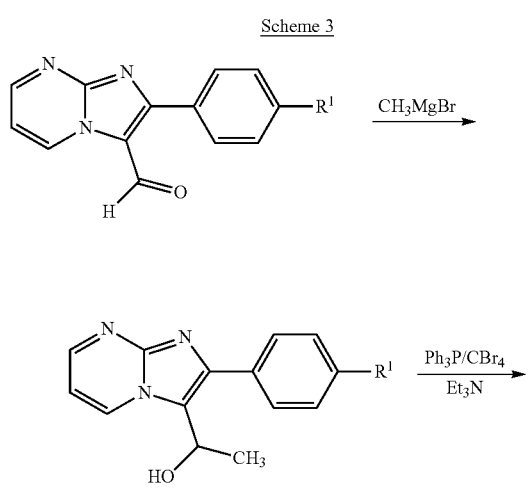
Scheme 3
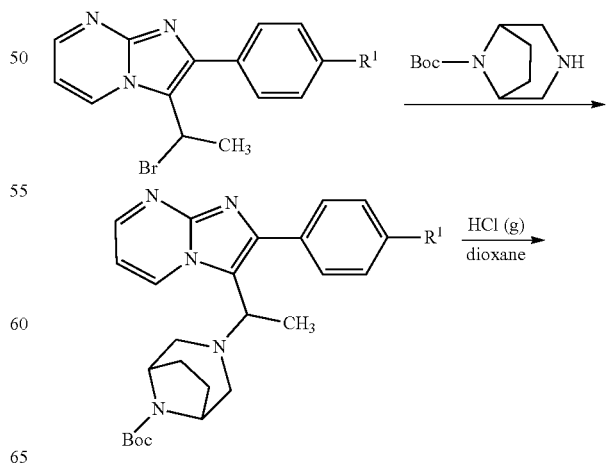

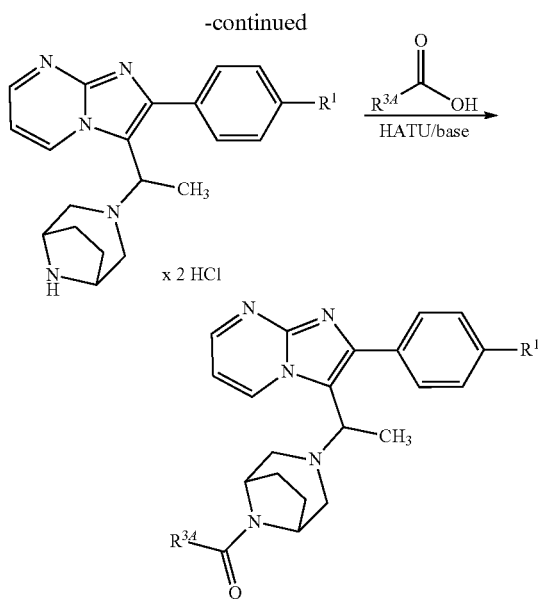

The compounds of the invention have valuable pharmacological properties and can be used for prevention and treatment of diseases in humans and animals.

The compounds of the invention are potent and selective blockers of TASK-1 and TASK-3 channels and are therefore suitable for the treatment and/or prevention of disorders and pathological processes, in particular those caused by activation of TASK-1 and/or TASK-3 or by activated TASK-1 and/or TASK-3, and of disorders secondary to damage caused by TASK-1 and/or TASK-3.

For the purposes of the present invention, this includes in particular disorders from the group of the respiratory disorders and sleep-related respiratory disorders, such as obstructive sleep apnoea (in adults and children), primary snoring, obstructive snoring (upper airway resistance syndrome, heavy snoring, hypopnoea syndrome), central sleep apnoea, mixed sleep apnoeas, Cheyne-Stokes respiration, primary sleep apnoea of infancy, apparent life-threatening event, central sleep apnoea as a result of the use of medicaments or the use of other substances, obesity hypoventilation syndrome, disrupted central respiratory drive, sudden infant death, primary alveolar hypoventilation syndrome, postoperative hypoxia and apnoea, muscular respiratory disorders, respiratory disorders following long-term ventilation, respiratory disorders during adaptation in high mountains, acute and chronic pulmonary diseases with hypoxia and hypercapnia, sleep-related non-obstructive alveolar hypoventilation and the congenital central alveolar hypoventilation syndrome.

The compounds of the invention can additionally be used for treatment and/or prevention of neurodegenerative disorders such as dementia, dementia with Lewy bodies, Alzheimer's disease, Parkinson's disease, Huntington's disease, Pick's disease, Wilson's disease, progressive supranuclear paresis, corticobasal degeneration, tauopathy, frontotemporal dementia and parkinsonism linked to chromosome 17, multisystem atrophy, spinocerebellar ataxias, spinobulbar muscular atrophy of the Kennedy type, Friedreich's ataxia, dentatorubral-pallidoluysian atrophy, amyotrophic lateral sclerosis, primary lateral sclerosis, spinal muscular atrophy, Creutzfeldt-Jakob disease and variants of Creutzfeldt-Jakob disease, infantile neuroaxonal dystrophy, neurodegeneration with brain iron accumulation, frontotemporal lobar degeneration with ubiquitin proteasome system and familial encephalopathy with neuroserpin inclusions.

In addition, the compounds of the invention can be used for treatment and/or prevention of neuroinflammatory and neuroimmunological disorders of the central nervous system (CNS), for example multiple sclerosis (Encephalomyelitis disseminata), transverse myelitis, Neuromyelitis optica, acute disseminated encephalomyelitis, optic neuritis, meningitis, encephalitis, demyelinating diseases and also inflammatory vascular changes in the central nervous system.

Moreover, the compounds of the invention are suitable for the treatment and/or prevention of neoplastic disorders such as, for example, skin cancer, breast cancer, lung cancer, colon cancer and prostate cancer.

The compounds of the invention are also suitable for treatment and/or prevention of cardiac arrhythmias, for example atrial and ventricular arrhythmias, conduction defects such as first- to third-degree atrio-ventricular blocks, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes and AV nodal re-entrant tachycardia.

Further cardiovascular disorders where the compounds of the invention can be employed for treatment and/or prevention are, for example, heart failure, coronary heart disease, stable and unstable angina pectoris, high blood pressure (hypertension), pulmonary-arterial hypertension (PAH) and other forms of pulmonary hypertension (PH), renal hypertension, peripheral and cardial vascular disorders, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore thromboembolic disorders and ischaemias such as myocardial ischaemia, myocardial infarction, stroke, cardiac hypertrophy, transient and ischaemic attacks, preeclampsia, inflammatory cardiovascular disorders, spasms of the coronary arteries and peripheral arteries, oedema formation such as, for example, pulmonary oedema, cerebral oedema, renal oedema or oedema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilatative cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention can additionally be used for treatment and/or prevention of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of bronchiectasis, pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds of the invention are also suitable for treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immunocomplex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds of the invention for treatment and/or prevention of sequelae of renal insufficiency, for example hypertension, pulmonary oedema, heart failure, uraemia, anaemia, electrolyte disturbances (for example hyperkalaemia, hyponatraemia) and disturbances in bone and carbohydrate metabolism.

In addition, the compounds of the invention are suitable for treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence, for example mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds of the invention are further suitable for treatment and/or prevention of inflammatory disorders and autoimmune disorders such as, for example, rheumatoid disorders, inflammatory eye disorders, chronic obstructive pulmonary disease (COPD), acute respiratory distress syndrome (ARDS), acute lung injury (ALI), alpha-1-antitrypsin deficiency (AATD), pulmonary emphysema (e.g. pulmonary emphysema induced by cigarette smoke), cystic fibrosis (CF), sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epidimytitis, oophoritis, salpingitis and vulvovaginitis, and also for the treatment and/or prevention of fibrotic disorders of internal organs such as, for example, the lung, the heart, the kidney, the bone marrow and especially the liver, of dermatological fibroses and of fibrotic disorders of the eye. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphea, keloids, hypertrophic scarring, nevi, diabetic retinopathy, proliferative vitroretinopathy and disorders of the connective tissue (for example sarcoidosis). The compounds of the invention can likewise be used for promotion of wound healing, for controlling postoperative scarring, for example following glaucoma operations and cosmetically for ageing or keratinized skin.

In addition, the compounds of the invention can be used for treatment and/or prevention of arteriosclerosis, impaired lipid metabolism and dyslipidaemias (hypolipoproteinaemia, hypertriglyceridaemia, hyperlipidaemia, combined hyperlipidaemias, hypercholesterolaemia, abetalipoproteinaemia, sitosterolaemia), xanthomatosis, Tangier disease, adiposity, obesity, metabolic disorders (metabolic syndrome, hyperglycaemia, insulin-dependent diabetes, non-insulin-dependent diabetes, gestation diabetes, hyperinsulinaemia, insulin resistance, glucose intolerance and diabetic sequelae, such as retinopathy, nephropathy and neuropathy), of anaemias such as haemolytic anaemias, in particular haemoglobinopathies such as sickle cell anaemia and thalassaemias, megaloblastic anaemias, iron deficiency anaemias, anaemias owing to acute blood loss, displacement anaemias and aplastic anaemias, of disorders of the gastrointestinal tract and the abdomen (glossitis, gingivitis, periodontitis, oesophagitis, eosinophilic gastroenteritis, mastocytosis, Crohn's disease, colitis, proctitis, anus pruritis, diarrhoea, coeliac disease, hepatitis, hepatic fibrosis, cirrhosis of the liver, pancreatitis and cholecystitis), of disorders of the central nervous system (stroke, epilepsy, depression), immune disorders, thyroid disorders (hyperthyreosis), skin disorders (psoriasis, acne, eczema, neurodermatitis, various forms of dermatitis, keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), of viral diseases (caused by influenza, adeno and corona viruses, for example HPV, HCMV, HIV, SARS), of disorders of the skeletal bone and the joints and also the skeletal muscle, of inflammatory arterial lesions (various forms of arteritis, for example endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, for example cataract, cachexia, osteoporosis, gout, incontinence, leprosy, Sezary syndrome and paraneoplastic syndrome, in the event of rejection reactions after organ transplants and for wound healing and angiogenesis particularly in the case of chronic wounds.

By virtue of their property profile, the compounds of the invention are preferably suitable for treatment and/or prevention of respiratory disorders, in particular of sleep-related respiratory disorders such as obstructive and central sleep apnoeas and also primary and obstructive snoring, for treatment and/or prevention of cardiac arrhythmias and also for treatment and/or prevention of neurodegenerative, neuroinflammatory and neuroimmunological disorders.

The aforementioned well-characterized diseases in humans can also occur with comparable aetiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a process for treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders. Preferred examples of combination active ingredients suitable for this purpose include:

respiratory stimulants, by way of example and with preference theophylline, doxapram, nikethamide or caffeine;

psychostimulants, by way of example and with preference modafinil or armodafinil;

amphetamines and amphetamine derivatives, by way of example and with preference amphetamine, metamphetamine or methylphenidate;

serotonin reuptake inhibitors, by way of example and with preference fluoxetine, paroxetine, citalopram, escitalopram, sertraline, fluvoxamine or trazodone;

serotonin precursors, by way of example and with preference L-tryptophan;

selective serotonin noradrenaline reuptake inhibitors, by way of example and with preference venlafaxine or duloxetine;

noradrenergic and specific serotonergic antidepressants, by way of example and with preference mirtazapine;

selective noradrenaline reuptake inhibitors, by way of example and with preference reboxetine;

tricyclic antidepressants, by way of example and with preference amitriptyline, protriptyline, doxepine, trimipramine, imipramine, clomipramine or desipramine;

alpha2-adrenergic agonists, by way of example and with preference clonidine;

GABA agonists, by way of example and with preference baclofen;

alpha sympathomimetics, by way of example and with preference xylometazoline, oxymetazoline, phenylephrine, naphazoline, tetryzoline or tramazoline;

glucocorticoids, by way of example and with preference fluticasone, budesonide, beclometasone, mometasone, tixocortol or triamcinolone;

cannabinoid receptor agonists;

carboanhydrase inhibitors, by way of example and with preference acetazolamide, methazolamide or diclofenamide;

opioid and benzodiazepine receptor antagonists, by way of example and with preference flumazenil, naloxone or naltrexone;

cholinesterase inhibitors, by way of example and with preference neostigmine, pyridostigmine, physostigmine, donepezil, galantamine or rivastigmine;

N-methyl-D-aspartate and glutamate antagonists, by way of example and with preference amantadine, memantine or sabeluzole;

nicotine receptor agonists;

leukotriene receptor antagonists, by way of example and with preference montelukast or tipelukast;

dopamine receptor antagonists, by way of example and with preference dromperidone, metoclopramide or benzamide, butyrophenone or phenothiazine derivatives;

appetite suppressants, by way of example and with preference sibutramine, topiramate, phentermine, lipase inhibitors or cannabinoid receptor antagonists;

proton pump inhibitors, by way of example and with preference pantoprazole, omeprazole, esomeprazole, lansoprazole or rabeprazole;

organic nitrates and NO donors, for example sodium nitroprusside, nitroglycerin, isosorbide mononitrate, isosorbide dinitrate, molsidomine or SIN-1, and inhaled NO;

compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;

NO- and haem-independent activators of soluble guanylate cyclase (sGC), such as in particular the compounds described in WO 01/19355, WO 01/19776, WO 01/19778, WO 01/19780, WO 02/070462 and WO 02/070510;

NO-independent but haem-dependent stimulators of soluble guanylate cyclase (sGC), such as in particular riociguat, vericiguat and the compounds described in WO 00/06568, WO 00/06569, WO 02/42301, WO 03/095451, WO 2011/147809, WO 2012/004258, WO 2012/028647 and WO 2012/059549;

prostacyclin analogs and IP receptor agonists, by way of example and with preference iloprost, beraprost, treprostinil, epoprostenol or selexipag;

endothelin receptor antagonists, by way of example and with preference bosentan, darusentan, ambrisentan or sitaxsentan;

compounds which inhibit human neutrophile elastase (HNE), by way of example and with preference sivelestat or DX-890 (reltran);

compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);

compounds which block the binding of serotonin to its receptors, by way of example and with preference antagonists of the 5-HT$_{2B}$ receptor such as PRX-08066;

antagonists of growth factors, cytokines and chemokines, by way of example and with preference antagonists of TGF-β, CTGF, IL-1, IL-4, IL-5, IL-6, IL-8, IL-13 and integrins;

Rho kinase-inhibiting compounds, by way of example and with preference fasudil, Y-27632, SLx-2119, BF-66851, BF-66852, BF-66853, KI-23095 or BA-1049;

compounds which influence the energy metabolism of the heart, by way of example and with preference etomoxir, dichloroacetate, ranolazine or trimetazidine;

compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

anti-obstructive agents as used, for example, for treatment of chronic obstructive pulmonary disease (COPD) or bronchial asthma, by way of example and with preference from the group of the inhalatively or systemically administered agonists of the beta-adrenergic receptor (beta-mimetics) and the inhalatively administered antimuscarinergic substances;

antiinflammatory, immunomodulating, immunosuppressive and/or cytotoxic agents, by way of example and with preference from the group of the systemically or inhalatively administered corticosteroids and also dimethyl fumarate, fingolimod, glatiramer acetate, β-interferons, natalizumab, teriflunomide, mitoxantrone, immunoglobulins, acetylcysteine, montelukast, tipelukast, azathioprine, cyclophosphamide, hydroxycarbamide, azithromycin, interferon-γ, pirfenidone or etanercept;

antifibrotic agents, by way of example and with preference lysophosphatidic acid receptor 1 (LPA-1) antagonists, CTGF inhibitors, IL-4 antagonists, IL-13 antagonists, TGF-β antagonists or pirfenidone;

antithrombotic agents, by way of example and with preference from the group of platelet aggregation inhibitors, the anticoagulants and the profibrinolytic substances;

hypotensive active ingredients, by way of example and with preference from the group of the calcium antagonists, angiotensin AII antagonists, ACE inhibitors, vasopeptidase inhibitors, endothelin antagonists, renin inhibitors, alpha receptor blockers, beta receptor blockers, mineralocorticoid receptor antagonists and also the diuretics; and/or active ingredients altering lipid metabolism, for example and with preference from the group of the thyroid receptor agonists, cholesterol synthesis inhibitors such as, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbents, bile acid reabsorption inhibitors and lipoprotein(a) antagonists.

In a preferred embodiment of the invention, the compounds of the invention are administered in combination with a beta-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscarinergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, betamethasone, beclomethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha receptor blockers, beta receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1 receptor blocker, by way of example and with preference prazosin.

In a preferred embodiment of the invention, the compounds of the invention are administered in combination with a beta receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, preferred examples being losartan, candesartan, valsartan, telmisartan or embusartan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

Particular preference is given to combinations of the compounds of the invention with one or more further active ingredients selected from the group consisting of respiratory stimulants, psychostimulants, serotonin reuptake inhibitors, noradrenergic, serotonergic and tricyclic antidepressants, sGC stimulators, mineralocorticoid receptor antagonists, antiinflammatory drugs, immunomodulators, immunosuppressives and cytotoxic drugs.

If required, the substances of the invention can also be employed in conjunction with the use of one or more medical technical devices or auxiliaries, provided that this does not lead to unwanted and unacceptable side-effects. Medical devices and auxiliaries suitable for such a combined application are, by way of example and with preference:

- devices for positive airway pressure ventilation, by way of example and with preference CPAP (continuous positive airway pressure) devices, BiPAP (bilevel positive airway pressure) devices and IPPV (intermittent positive pressure ventilation) devices;
- neurostimulators of the Nervus hypoglossus;
- intraoral auxiliaries, by way of example and with preference protrusion braces;
- nasal disposable valves;
- nasal stents.

The present invention further provides medicaments which comprise at least one compound of the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, intrapulmonal (inhalative), nasal, intranasal, pharyngeal, lingual, sublingual, buccal, rectal, dermal, transdermal, conjunctival or otic route, or as an implant or stent.

The compounds according to the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include inter alia preparations for injection and infusion in the form of solutions, suspensions, emulsions, lyophilizates or sterile powders.

Suitable for the other administration routes are, for example, pharmaceutical forms for inhalation (including powder inhalers, nebulizers, metered aerosols), nasal drops, solutions or sprays, throat sprays, tablets for lingual, sublingual or buccal administration, films/wafers or capsules, suppositories, eye drops, eye ointments or eyewashes, ocular inserts, ear drops, sprays, powders, washes or tampons, vaginal capsules, aqueous suspensions (lotions, shaking mixtures), lipophilic suspensions, emulsions, microemulsions, ointments, creams, transdermal therapeutic systems (e.g. patches), milk, pastes, foams, dusting powders, implants or stents.

Preference is given to oral, intravenous, intranasal and pharyngeal administration.

In one embodiment, administration is by the intranasal route. In one embodiment, intranasal administration is effected with the aid of nose drops or a nasal spray. In one embodiment, intranasal administration is effected with the aid of a nasal spray.

The compounds according to the invention can be converted to the administration forms mentioned. This can be done in a manner known per se, by mixing with inert, nontoxic, pharmaceutically suitable excipients. These excipients include

- fillers and carriers (for example cellulose, microcrystalline cellulose, for example Avicel®, lactose, mannitol, starch, calcium phosphates, for example Di-Cafos®),
- ointment bases (for example vaseline, paraffins, triglycerides, waxes, wool wax, wool wax alcohols, lanolin, hydrophilic ointment, polyethylene glycols),
- suppository bases (for example polyethylene glycols, cocoa butter, hard fat),
- solvents (e.g. water, ethanol, isopropanol, glycerol, propylene glycol, mid-chain triglycerides fatty oils, liquid polyethylene glycols, paraffins),
- surfactants, emulsifiers, dispersants or wetting agents (for example sodium dodecylsulfate, lecithin, phospholipids, fatty alcohols, for example Lanette®, sorbitan fatty acid esters, for example Span®, polyoxyethylene sorbitan fatty acid esters, for example Tween®, polyoxyethylene fatty acid glycerides, for example Cremophor®, polyoxyethylene fatty acid esters, polyoxyethylene fatty alcohol ethers, glycerol fatty acid esters, poloxamers, for example Pluronic®),
- buffer substances, and also acids and bases (for example phosphates, carbonates, citric acid, acetic acid, hydrochloric acid, sodium hydroxide, ammonium carbonate, trometamol, triethanolamine),
- isotonizing agents (for example glucose, sodium chloride),
- adsorbents (for example finely divided silicas),
- viscosity-increasing agents, gel formers, thickeners or binders (for example polyvinylpyrrolidone, methyl cellulose, hydroxypropyl cellulose, hydroxypropyl methylcellulose, carboxymethyl cellulose-sodium, starch, carbomers, polyacrylic acids, for example Carbopol®, alginates, gelatins),
- disintegrants (for example modified starch, carboxymethyl cellulose-sodium, sodium starch glycolate, for example Explotab®, crosslinked polyvinylpyrrolidone, croscarmellose-sodium, for example AcDiSol®),
- flow regulators, lubricants, glidants and mould release agents (for example magnesium stearate, stearic acid, talc, finely divided silicas, for example Aerosil®),
- coating agents (for example sugar, shellac) and film formers for films or diffusion membranes with fast or modified dissolution (for example polyvinylpyrrolidones, for example Kollidon®, polyvinyl alcohol, ethyl cellulose, hydroxypropyl cellulose, hydroxypropyl methyl cellulose, hydroxypropyl methyl cellulose phthalate, cellulose acetate, cellulose acetate phthalate, polyacrylates, polymethacrylates, for example Eudragit®),
- capsule materials (e.g. gelatins, hydroxypropyl methyl cellulose), natural polymers (for example albumins),
synthetic polymers (for example polylactides, polyglycolides, polyacrylates, polymethacrylates, for example Eudragit®, polyvinylpyrrolidones, for example Kollidon®, polyvinyl alcohols, polyvinyl acetates, polyethylene oxides, polyethylene glycols and the copolymers and block copolymers thereof),
plasticizers (for example polyethylene glycols, propylene glycol, glycerol, triacetin, triacetyl citrate, dibutyl phthalate),
penetrants,
stabilizers (e.g. antioxidants, for example ascorbic acid, sodium ascorbate, ascorbyl palmitate, butylhydroxyanisole, butylhydroxytoluene, propyl gallate),
preservatives (for example parabens, sorbic acid, sodium benzoate, thiomersal, benzalkonium chloride, chlorhexidine acetate),
dyes (e.g. inorganic pigments, for example iron oxides, titanium dioxide),
aromas, sweeteners, flavour and/or odour correctors.

In general, it has been found to be advantageous in the case of parenteral administration to administer amounts of active compound of about 0.001 to 1 mg/kg, preferably about 0.01 to 0.5 mg/kg, of body weight to achieve effective results. In the case of oral administration the dosage is about 0.01 to 100 mg/kg, preferably about 0.01 to 20 mg/kg and most preferably 0.1 to 10 mg/kg body weight. In the case of intrapulmonary administration, the amount of active compound is generally about 0.1 to 50 mg per inhalation.

In one embodiment, the dosage in the case of intranasal administration is about 0.1 µg to 500 µg per day. In a further embodiment, the dosage in the case of intranasal administration is about 1 µg to 250 µg per day. In a further embodiment, the dosage in the case of intranasal administration is about 1 µg to 120 µg per day. In a further embodiment, the dose of about 0.1 µg to 500 µg per day, or of about 1 µg to 250 µg per day, or of about 1 µg to 120 µg per day, is administered once daily by the intranasal route before sleeping. In one embodiment, the dose of about 0.1 µg to 500 µg per day, or of about 1 µg to 250 µg per day, or of about 1 µg to 120 µg per day, is administered once daily with half to each nostril. In one embodiment, the dose of about 0.1 µg to 500 µg per day, or of about 1 µg to 250 µg per day, or of about 1 µg to 120 µg per day, is administered once daily with half to each nostril before sleeping.

It may nevertheless be necessary in some cases to deviate from the stated amounts of active compounds, specifically as a function of body weight, route of administration, individual response to the active ingredient, nature of the preparation and time or interval over which administration takes place. Thus in some cases it may be sufficient to manage with less than the aforementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

Abbreviations and Acronyms abs. absolute
Ac acetyl
aq. aqueous, aqueous solution
Boc tert-butoxycarbonyl
br. broad (in NMR signal)
Ex. Example
Bu butyl
c concentration
cat. catalytic
CI chemical ionization (in MS)
d doublet (in NMR)
d day(s)
DCI direct chemical ionization (in MS)
dd doublet of doublets (in NMR)
DMF N,N-dimethylformamide
DMSO dimethyl sulfoxide
dq doublet of quartets (in NMR)
dt doublet of triplets (in NMR)
EI electron impact ionization (in MS)
eq. equivalent(s)
ESI electrospray ionization (in MS)
Et ethyl
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high-pressure, high-performance liquid chromatography
iPr isopropyl
conc. concentrated (in the case of a solution)
LC liquid chromatography
LC-MS liquid chromatography-coupled mass spectrometry
lit. literature (reference)
m multiplet (in NMR)
Me methyl
min minute(s)
MS mass spectrometry
NMR nuclear magnetic resonance spectrometry
Ph phenyl
Pr propyl
q quartet (in NMR)
quant. quantitative (in chemical yield)
RP reverse phase (in HPLC)
RT room temperature
$R_t$ retention time (in HPLC, LC-MS)
s singlet (in NMR)
SFC supercritical liquid chromatography
t triplet (in NMR)
tBu tert-butyl
TFA trifluoroacetic acid
THF tetrahydrofuran
UV ultraviolet spectrometry
v/v volume to volume ratio (of a solution)
tog. together LC-MS and HPLC Methods:

Method 1 (LC-MS):
Instrument: Waters Acquity SQD UPLC System; column: Waters Acquity UPLC HSS T31.8 µm, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; temperature: 50° C.; flow rate: 0.40 ml/min; UV detection: 208-400 nm.

Method 2 (LC-MS):
MS instrument: Thermo Scientific FT-MS; instrument type UHPLC: Thermo Scientific UltiMate 3000; column: Waters HSS T3 C18 1.8 µm, 75 mm×2.1 mm; mobile phase A: 1 l of water+0.01% formic acid, mobile phase B: 1 l of acetonitrile+0.01% formic acid; gradient: 0.0 min 10%

B→2.5 min 95% B→3.5 min 95% B; temperature: 50° C.; flow rate: 0.90 ml/min; UV detection: 210 nm/optimum integration path 210-300 nm.

Method 3 (LC-MS):

MS instrument: Waters Micromass QM; HPLC instrument: Agilent 1100 series; column: Agilent ZORBAX Extend-C18 3.5 µm, 50 mm×3.0 mm; mobile phase A: 1 l of water+0.01 mol of ammonium carbonate, mobile phase B: 1 l of acetonitrile; gradient: 0.0 min 98% A→0.2 min 98% A→3.0 min 5% A→4.5 min 5% A; temperature: 40° C.; flow rate: 1.75 ml/min; UV detection: 210 nm.

Method 4 (LC-MS):

MS instrument: Waters Micromass Quattro Micro; HPLC instrument: Waters UPLC Acquity; column: Waters BEH C18 1.7 µm, 50 mm×2.1 mm; mobile phase A: 1 l of water+0.01 mol of ammonium formate, mobile phase B: 1 l of acetonitrile; gradient: 0.0 min 95% A→0.1 min 95% A→2.0 min 15% A→2.5 min 15% A→2.51 min 10% A→3.0 min 10% A; temperature: 40° C.; flow rate: 0.5 ml/min; UV detection: 210 nm.

Method 5 (LC-MS):

Instrument: Agilent MS Quad 6150 with HPLC Agilent 1290; column: Waters Acquity UPLC HSS T3 1.8 µm, 50 mm×2.1 mm; mobile phase A: 1 l of water+0.25 ml of 99% strength formic acid, mobile phase B: 1 l of acetonitrile+0.25 ml of 99% strength formic acid; gradient: 0.0 min 90% A→0.3 min 90% A→1.7 min 5% A→3.0 min 5% A; flow rate: 1.20 ml/min; temperature: 50° C.; UV detection: 205-305 nm.

Method 6 (LC-MS):

MS instrument: Waters Single Quad MS System; HPLC instrument: Waters UPLC Acquity; column: Waters BEH C18 1.7 µm, 50 mm×2.1 mm; mobile phase A: 1 l of water+1.0 ml of 25% strength ammonia, mobile phase B: 1 l of acetonitrile; gradient: 0.0 min 92% A→0.1 min 92% A→1.8 min 5% A→3.5 min 5% A; temperature: 50° C.; flow rate: 0.45 ml/min; UV detection: 210 nm (208-400 nm).

Method 7 (LC-MS):

MS instrument: Waters SQD; HPLC instrument: Waters UPLC; column: Zorbax SB-Aq (Agilent), 50 mm×2.1 mm, 1.8 µm; mobile phase A: water+0.025% formic acid, mobile phase B: acetonitrile+0.025% formic acid; gradient: 0.0 min 98% A→0.9 min 25% A→1.0 min 5% A→1.4 min 5% A→1.41 min 98% A→1.5 min 98% A; temperature: 40° C.; flow rate: 0.60 ml/min; UV detection: DAD, 210 nm.

Method 8 (Preparative HPLC):

Instrument: Abimed Gilson 305; column: Reprosil C18 10 µm, 250 mm×30 mm; mobile phase A: water, mobile phase B: acetonitrile; gradient: 0-3 min 10% B, 3-27 min 10% B→95% B, 27-34.5 min 95% B, 34.5-35.5 min 95% B→10% B, 35.5-36.5 min 10% B; flow rate: 50 ml/min; room temperature; UV detection: 210 nm.

Method 9 (Preparative HPLC):

Instrument: Waters Prep LC/MS System; column: XBridge C18 5 µm, 100 mm×30 mm; mobile phase A: water, mobile phase B: acetonitrile; gradient profile: 0-2 min 10% B, 2-2.2 min→30% B, 2.2-7 min→70% B, 7-7.5 min→92% B, 7.5-9 min 92% B; flow rate: 65 ml/min+5 ml 2% ammonia in water; room temperature; UV detection: 200-400 nm; at-column injection (complete injection).

Further Details:

The percentages in the example and test descriptions which follow are, unless indicated otherwise, percentages by weight; parts are parts by weight. Solvent ratios, dilution ratios and concentration data for liquid/liquid solutions are based in each case on volume.

Purity figures are generally based on corresponding peak integrations in the LC/MS chromatogram, but may additionally also have been determined with the aid of the $^1$H NMR spectrum. If no purity is stated, the purity is generally >95% according to automated peak integration in the LC/MS chromatogram, or the purity has not been determined explicitly.

Stated yields in % of theory are generally corrected for purity if a purity of <100% is indicated. In solvent-containing or contaminated batches, the formal yield may be ">100%"; in these cases the yield is not corrected for solvent or purity.

In cases where the reaction products were obtained by trituration, stirring or recrystallization, it was frequently possible to isolate further amounts of product from the respective mother liquor by chromatography. However, a description of this chromatography is dispensed with hereinbelow unless a large part of the total yield could only be isolated in this step.

Melting points and melting ranges, if stated, are uncorrected.

The descriptions of the coupling patterns of $^1$H NMR signals that follow have in some cases been taken directly from the suggestions of the ACD SpecManager (ACD/Labs Release 12.00, Product version 12.5) and have not necessarily been strictly scrutinized. In some cases, the suggestions of the SpecManager were adjusted manually. Manually adjusted or assigned descriptions are generally based on the optical appearance of the signals in question and do not necessarily correspond to a strict, physically correct interpretation. In general, the stated chemical shift refers to the centre of the signal in question. In the case of broad multiplets, an interval is given. Signals obscured by solvent or water were either tentatively assigned or have not been listed.

The $^1$H NMR data of synthesis intermediates and working examples can also be stated in the form of $^1$H NMR peak lists. Here, for each signal peak, first the δ value in ppm and then the signal intensity in round brackets are listed. The δ value/signal intensity number pairs of different signal peaks are listed separated by commas; accordingly, the peak list for a compound has the form: $δ_1$ (intensity$_1$), $δ_2$ (intensity$_2$), . . . , $δ_i$ (intensity$_i$), . . . , $δ_n$ (intensity$_n$).

The intensity of sharp signals correlates with the height of the signals (in cm) in a printed example of an NMR spectrum and shows the true ratios of the signal intensities in comparison with other signals. In the case of broad signals, several peaks or the middle of the signal and their relative intensity may be given in comparison to the most intense signal in the spectrum. The lists of the $^1$H NMR peaks are similar to the conventional $^1$H NMR printouts and thus usually contain all peaks listed in a conventional NMR interpretation. In addition, like classic $^1$H NMR printouts, they may comprise solvent signals, signals of stereoisomers of the target compound in question, peaks of impurities, $^{13}$C satellite peaks and/or rotation side bands. Peaks of stereoisomers of the target compound and/or peaks of impurities usually have a lower intensity on average than the peaks of the target compound (for example with a purity of >90%). Such stereoisomers and/or impurities may be typical of the particular preparation process. Their peaks can thus help in identifying reproduction of the preparation process with reference to "by-product fingerprints". An expert calculating the peaks of a target compound by known methods (MestreC, ACD simulation, or using empirically determined expected values) can, if required, isolate the peaks of the target compound, optionally using additional intensity filters. This isolation would be similar to the peak picking in question in conventional $^1$H NMR interpretation.

A detailed description of the presentation of NMR data in the form of peak lists can be found in the publication "Citation of NMR Peaklist Data within Patent Applications" (see http://www.researchdisclosure.com/searching-disclosures, Research Disclosure Database Number 605005, 2014, 1 Aug. 2014). In the peak picking routine described in the stated Research Disclosure, the parameter "MinimumHeight" can be set between 1% and 4%. However, depending on the type of chemical structure and/or on the concentration of the compound to be analysed, it may also be advisable to set the parameter "MinimumHeight" to values of <1%.

All reactants or reagents whose preparation is not described explicitly hereinafter were purchased commercially from generally accessible sources. For all other reactants or reagents whose preparation is likewise not described hereinafter and which were not commercially obtainable or were obtained from sources which are not generally accessible, a reference is given to the published literature in which their preparation is described.

$^1$H-NMR (400 MHz, DMSO-$d_6$, δ/ppm): 7.07 (dd, 1H), 7.53 (d, 2H), 8.03 (d, 2H), 8.41 (s, 1H), 8.54 (dd, 1H), 8.97 (dd, 1H).

Example 2A 2-(4-Isopropylphenyl)imidazo[1,2-a]pyrimidine

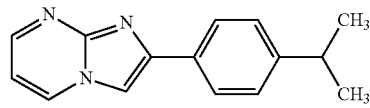

Sodium bicarbonate (0.52 g, 6.22 mmol) was added to a solution of 2-bromo-1-(4-isopropylphenyl)ethanone (1.0 g, 4.15 mmol) and pyrimidin-2-amine (0.43 g, 4.6 mmol) in 50 ml of ethanol, and the mixture was stirred at 80° C. for 5 hours. The mixture was then concentrated to dryness. The residue was stirred with diethyl ether and the solid that remained was filtered off and dried at 40° C. under reduced pressure overnight. This gave 1.15 g of the crude target product, which was used in subsequent reactions without further purification.

LC-MS (Method 2): $R_t$=1.48 min; m/z=238 (M+H)$^+$.

$^1$H-NMR (400 MHz, DMSO-$d_6$, δ/ppm): 1.24 (d, 6H), 2.87-3.00 (m, 1H), 7.04 (dd, 1H), 7.34 (d, 2H), 7.92 (d, 2H), 8.33 (s, 1H), 8.51 (dd, 1H), 8.95 (dd, 1H).

Analogously to Examples 1A and 2A, the following compound was prepared from the starting materials specified:

| Example | Name/Structure/Starting materials | Analytical data |
|---|---|---|
| 3A | 2-(4-bromophenyl)imidazo[1,2-a]pyrimidine<br><br>from 2-bromo-1-(4-bromophenyl)ethanone and pyrimidin-2-amine | $^1$H-NMR (400 MHz, DMSO-$d_6$): δ [ppm] = 7.07 (dd, 1H), 7.67 (d, 2H), 7.97 (d, 2H), 8.42 (s, 1H), 8.54 (dd, 1H), 8.97 (dd, 1H).<br>LC-MS (Method 2):<br>$R_t$ = 1.34 min; m/z = 274/276 (M + H)$^+$. |

Starting Compounds and Intermediates

Example 1A 2-(4-Chlorophenyl)imidazo[1,2-a]pyrimidine

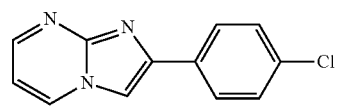

Sodium bicarbonate (10.8 g, 128 mmol) was added to a solution of 2-bromo-1-(4-chlorophenyl)ethanone (20.0 g, 85.7 mmol) and pyrimidin-2-amine (8.96 g, 94.2 mmol) in 200 ml of ethanol, and the mixture was stirred at 80° C. for 5 hours. The batch was then cooled to 0° C. (ice bath). The resulting precipitate was filtered off and washed twice with an ethanol/water mixture (1:1). The solid was then dried under reduced pressure at 40° C. overnight. This gave 15.9 g (69.23 mmol, 80.8% of theory) of the target product.

LC-MS (Method 2): $R_t$=1.25 min; m/z=230 (M+H)$^+$.

Example 4A 2-(4-Chlorophenyl)imidazo[1,2-a]pyrimidine-3-carbaldehyde

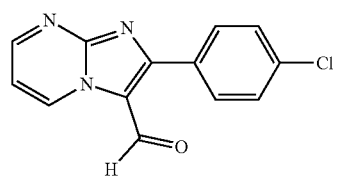 [SMILES: O=Cc1c(-c2ccc(Cl)cc2)nc2ncccn12]

300 ml of DMF were initially charged and cooled to 0° C. Phosphorus oxychloride (16 ml, 173 mmol) was then slowly added dropwise. The solution was then slowly warmed to room temperature and stirred at this temperature for another hour. 2-(4-Chlorophenyl)imidazo[1,2-a]pyrimidine (15.9 g, 69.2 mmol) was then added a little at a time. After the addition had ended, the reaction mixture was heated to 80° C. and stirred at this temperature for 1 hour. The batch was then cooled to 0° C. (ice bath). The resulting solid was filtered off with suction, washed repeatedly with water and dried in a high-vacuum drying cabinet at 40° C. overnight. This gave 13.75 g (53.36 mmol, 77% of theory) of the target product.

LC-MS (Method 2): $R_t$=1.44 min; m/z=258 (M+H)$^+$.

$^1$H-NMR (400 MHz, DMSO-d$_6$): δ [ppm]=7.46 (dd, 1H), 7.65 (d, 2H), 8.01 (d, 2H), 8.91 (dd, 1H), 9.83 (dd, 1H), 10.07 (s, 1H).

Example 5A 2-(4-Isopropylphenyl)imidazo[1,2-a]pyrimidine-3-carbaldehyde

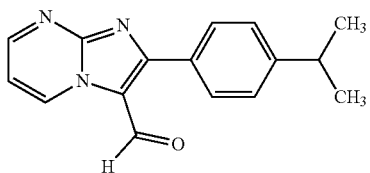 [SMILES: CC(C)c1ccc(-c2nc3ncccn3c2C=O)cc1]

50 ml of DMF were initially charged and cooled to 0° C. Phosphorus oxychloride (2.86 ml, 30.66 mmol) was then slowly added dropwise. The solution was then slowly warmed to room temperature and stirred at this temperature for another hour. 2-(4-Isopropylphenyl)imidazo[1,2-a]pyrimidine (2.91 g, 12.26 mmol) was then added a little at a time. After the addition had ended, the reaction mixture was heated to 80° C. and stirred at this temperature for 1 hour. The batch was then cooled to 0° C. (ice bath). The solid obtained was filtered off with suction and dried under reduced pressure. The resulting crude product was subsequently purified twice by column chromatography (Biotage Isolera, Biotage SNAP-KP-NH column, mobile phase cyclohexane/ethyl acetate gradient). This gave 3 g (11.3 mmol, 92% of theory) of the target compound.

LC-MS (Method 2): $R_t$=1.75 min; m/z=266 (M+H)$^+$.

$^1$H-NMR (400 MHz, DMSO-d$_6$): δ [ppm]=1.27 (d, 6H), 2.92-3.07 (m, 1H), 7.39-7.52 (m, 3H), 7.90 (d, 2H), 8.89 (dd, 1H), 9.83 (dd, 1H), 10.08 (s, 1H).

Analogously to Examples 4A and 5A, the following compound was prepared from the starting material specified:

Example 7A

7-{[2-(4-Chlorophenyl)imidazo[1,2-a]pyrimidin-3-yl]methyl}-3-oxa-7,9-diazabicyclo[3.3.1]nonane dihydrochloride

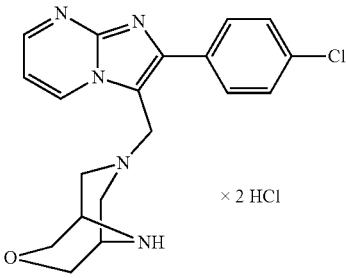 [SMILES: Clc1ccc(-c2nc3ncccn3c2CN2CC3COCC(C2)N3)cc1]

With stirring, 12 ml of a 4 M solution of hydrogen chloride in dioxane were added to tert-butyl 7-{[2-(4-chlorophenyl)imidazo[1,2-a]pyrimidin-3-yl]methyl}-3-oxa-7,9-diazabicyclo[3.3.1]nonane-9-carboxylate (1.52 g, 3.23 mmol). The mixture was stirred at room temperature overnight. The solids obtained were then filtered off with suction, washed repeatedly with diethyl ether and dried under high vacuum at 40° C. This gave 1.76 g of the target product.

LC-MS (Method 2): $R_t$=0.71 min; m/z=370 (M+H)$^+$.

Example 8A

7-{[2-(4-Isopropylphenyl)imidazo[1,2-a]pyrimidin-3-yl]methyl}-3-oxa-7,9-diazabicyclo[3.3.1]nonane dihydrochloride

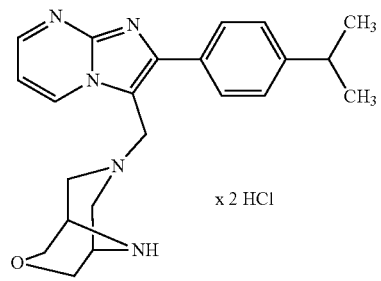 [SMILES: CC(C)c1ccc(-c2nc3ncccn3c2CN2CC3COCC(C2)N3)cc1]

| Example | Name/Structure/Starting material | Analytical data |
|---|---|---|
| 6A | 2-(4-bromophenyl)imidazo[1,2-a]pyrimidine-3-carbaldehyde<br><br>from 2-(4-bromophenyl)imidazo[1,2-a]pyrimidine | $^1$H-NMR (400 MHz, DMSO-d$_6$): δ [ppm] = 7.46 (dd, 1H), 7.79 (d, 2H), 7.94 (d, 2H), 8.91 (dd, 1H), 9.83 (dd, 1H), 10.07 (s, 1H).<br>LC-MS (Method 1):<br>$R_t$ = 0.78 min; m/z = 302/304 (M + H)$^+$. |

With stirring, 2.2 ml of a 4 M solution of hydrogen chloride in dioxane were added to tert-butyl 7-{[2-(4-isopropylphenyl)imidazo[1,2-a]pyrimidin-3-yl]methyl}-3-oxa-7,9-diazabicyclo[3.3.1]nonane-9-carboxylate (420 mg, 0.88 mmol). The mixture was stirred at room temperature overnight. The solids obtained were then filtered off with suction, washed repeatedly with diethyl ether and dried under high vacuum at 40° C. This gave 430 mg of the target product.

LC-MS (Method 2): $R_t$=0.87 min; m/z=378 (M+H)$^+$.

Example 9A 2-(4-Chlorophenyl)-3-(3,8-diazabicyclo[3.2.1]oct-3-ylmethyl)imidazo[1,2-a]pyrimidine dihydrochloride

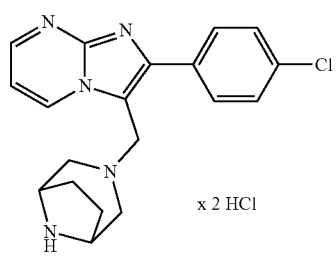 [SMILES: Clc1ccc(-c2nc3ncccn3c2CN2CC3CCC(C2)N3)cc1]

With stirring, 15 ml of a 4 M solution of hydrogen chloride in dioxane were added to tert-butyl 3-{[2-(4-chlorophenyl)imidazo[1,2-a]pyrimidin-3-yl]methyl}-3,8-diazabicyclo[3.2.1]octane-8-carboxylate (2.72 g, 6.00 mmol). The mixture was stirred at room temperature overnight. The solids obtained were then filtered off with suction, washed repeatedly with diethyl ether and dried under high vacuum at 40° C. This gave 3.5 g of the target product.

LC-MS (Method 6): $R_t$=1.36 min; m/z=354 (M+H)$^+$.

Example 10A 3-(3,8-Diazabicyclo[3.2.1]oct-3-ylmethyl)-2-(4-isopropylphenyl)imidazo[1,2-a]pyrimidine dihydrochloride

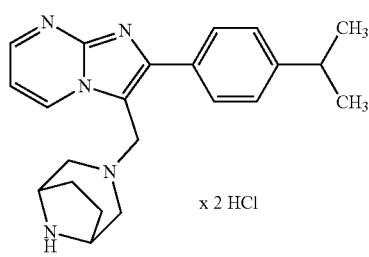 [SMILES: CC(C)c1ccc(-c2nc3ncccn3c2CN2CC3CCC(C2)N3)cc1]

With stirring, 2.57 ml of a 4 M solution of hydrogen chloride in dioxane were added to tert-butyl 3-{[2-(4-isopropylphenyl)imidazo[1,2-a]pyrimidin-3-yl]methyl}-3,8-diazabicyclo[3.2.1]octane-8-carboxylate (493 mg, 1.03 mmol). The mixture was stirred at room temperature overnight. The reaction solution was then concentrated to dryness and the resulting residue was dried under high vacuum at 40° C. This gave 393 mg of the target product.

LC-MS (Method 2): $R_t$=0.93 min; m/z=362 (M+H)$^+$.

Example 11A 2-(4-Chlorophenyl)-3-(2,5-diazabicyclo[2.2.2]oct-2-ylmethyl)imidazo[1,2-a]pyrimidine dihydrochloride (Enantiomer 1)

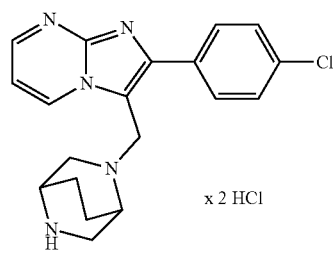 [SMILES: Clc1ccc(-c2nc3ncccn3c2CN2CC3CCC2CN3)cc1]

With stirring, 7.1 ml of a 4 M solution of hydrogen chloride in dioxane were added to tert-butyl 5-{[2-(4-chlorophenyl)imidazo[1,2-a]pyrimidin-3-yl]methyl}-2,5-diazabicyclo[2.2.2]octane-2-carboxylate (Enantiomer 1; 1.29 g, 2.84 mmol). The mixture was stirred at room temperature overnight. The solids obtained were then filtered off with suction, washed repeatedly with diethyl ether and dried under high vacuum at 40° C. This gave 1.4 g of the target product.

LC-MS (Method 2): $R_t$=0.79 min; m/z=354 (M+H)$^+$.

Example 12A 2-(4-Chlorophenyl)-3-(2,5-diazabicyclo[2.2.2]oct-2-ylmethyl)imidazo[1,2-a]pyrimidine dihydrochloride (Enantiomer 2)

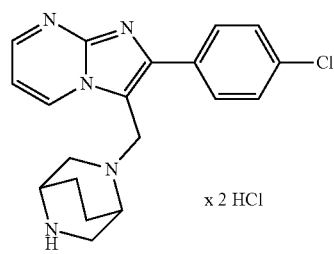 [SMILES: Clc1ccc(-c2nc3ncccn3c2CN2CC3CCC2CN3)cc1]

With stirring, 3.9 ml of a 4 M solution of hydrogen chloride in dioxane were added to tert-butyl 5-{[2-(4-chlorophenyl)imidazo[1,2-a]pyrimidin-3-yl]methyl}-2,5-diazabicyclo[2.2.2]octane-2-carboxylate (Enantiomer 2; 710 mg, 1.56 mmol). The mixture was stirred at room temperature overnight. The solids obtained were then filtered off with suction, washed repeatedly with diethyl ether and dried under high vacuum at 40° C. This gave 740 mg of the target product.

LC-MS (Method 1): $R_t$=0.49 min; m/z=354 (M+H)$^+$.

Example 13A 3-(2,5-Diazabicyclo[2.2.2]oct-2-ylmethyl)-2-(4-isopropylphenyl)imidazo[1,2-a]pyrimidine dihydrochloride (Enantiomer 1)

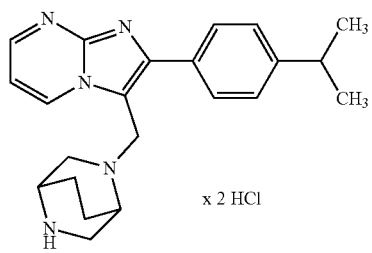 [SMILES: CC(C)c1ccc(-c2nc3ncccn3c2CN2CC3CCC2CN3)cc1]

With stirring, 4.2 ml of a 4 M solution of hydrogen chloride in dioxane were added to tert-butyl 5-{[2-(4-isopropylphenyl)imidazo[1,2-a]pyrimidin-3-yl]methyl}-2,5-diazabicyclo[2.2.2]octane-2-carboxylate (Enantiomer 1; 774 mg, 1.88 mmol). The mixture was stirred at room temperature overnight. The solids obtained were then filtered off with suction, washed repeatedly with diethyl ether and dried under high vacuum at 40° C. This gave 850 mg of the target product.

LC-MS (Method 1): $R_t$=0.54 min; m/z=362 (M+H)$^+$.

Example 14A 3-(2,5-Diazabicyclo[2.2.2]oct-2-ylmethyl)-2-(4-isopropylphenyl)imidazo[1,2-a]pyrimidine dihydrochloride (Enantiomer 2)

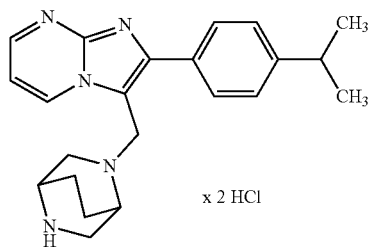 [SMILES: CC(C)c1ccc(-c2nc3ncccn3c2CN2CC3CCC2CN3)cc1]

With stirring, 4.0 ml of a 4 M solution of hydrogen chloride in dioxane were added to tert-butyl 5-{[2-(4-isopropylphenyl)imidazo[1,2-a]pyrimidin-3-yl]methyl}-2,5-diazabicyclo[2.2.2]octane-2-carboxylate (Enantiomer 2; 734 mg, 1.59 mmol). The mixture was stirred at room temperature overnight. The solids obtained were then filtered off with suction, washed repeatedly with diethyl ether and dried under high vacuum at 40° C. This gave 761 mg of the target product.

LC-MS (Method 1): $R_t$=0.55 min; m/z=362 (M+H)$^+$.

Example 15A

1-[2-(4-Chlorophenyl)imidazo[1,2-a]pyrimidin-3-yl]ethanol (racemate)

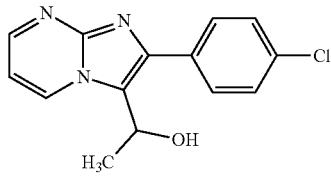 [SMILES: CC(O)c1c(-c2ccc(Cl)cc2)nc2ncccn12]

2-(4-Chlorophenyl)imidazo[1,2-a]pyrimidine-3-carbaldehyde (500 mg, 1.94 mmol) was suspended in 5 ml of THF. Subsequently, with ice cooling, methylmagnesium bromide in diethyl ether (3.0 M, 710 µl, 2.1 mmol) was added and the mixture was stirred at room temperature for 1 h. Then, a further 4 ml of THF and more methylmagnesium bromide in diethyl ether (3.0 M, 237 µl, 0.7 mmol) were added. The mixture was stirred at room temperature overnight. Aqueous ammonium chloride solution was then added, followed by water and ethyl acetate. The resulting organic phase was separated off, washed with saturated sodium chloride solution, dried over magnesium sulfate, filtered and concentrated to dryness under reduced pressure on a rotary evaporator. The residue was stirred in diethyl ether. The solid that remained was filtered off with suction and dried in a high-vacuum drying cabinet at 40° C. overnight. This gave 370 mg (1.35 mmol, 70% of theory) of the target product.

LC-MS (Method 2): $R_t$=1.22 min; m/z=274 (M+H)$^+$.

Example 16A 2-(4-Chlorophenyl)-3-[1-(3,8-diazabicyclo[3.2.1]oct-3-yl)ethyl]imidazo[1,2-a]pyrimidine dihydrochloride (racemate)

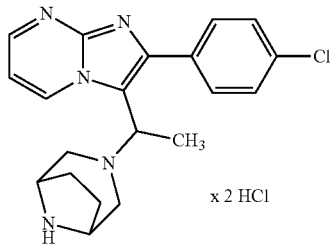 [SMILES: CC(c1c(-c2ccc(Cl)cc2)nc2ncccn12)N1CC2CCC(C1)N2]

With stirring, 0.21 ml of a 4 M solution of hydrogen chloride in dioxane and 0.2 ml of dioxane were added to tert-butyl 3-{1-[2-(4-chlorophenyl)imidazo[1,2-a]pyrimidin-3-yl]ethyl}-3,8-diazabicyclo[3.2.1]octane-8-carboxylate (racemate; 39.8 mg, 0.09 mmol). The mixture was stirred at room temperature overnight. The reaction solution was then concentrated to dryness and the resulting residue was dried under high vacuum at 40° C. This gave 41 mg of the target product.

LC-MS (Method 2): $R_t$=0.86 min; m/z=256/258 (M+H)$^+$.

Analogously to Examples 7A-14A, the following compounds were prepared from the starting material specified in each case:

| Example | Name/Structure/Starting material | Analytical data |
|---|---|---|
| 17A | 2-(4-bromophenyl)-3-(2,5-diazabicyclo[2.2.2]oct-2-ylmethyl)imidazo[1,2-a]pyrimidine dihydrochloride (racemate)<br>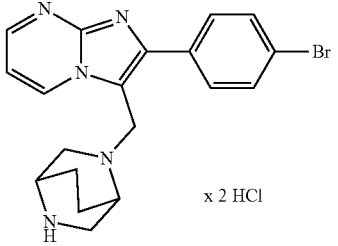<br>x 2 HCl<br>from tert-butyl 5-{[2-(4-bromophenyl)imidazo[1,2-a]pyrimidin-3-yl]methyl}-2,5-diazabicyclo[2.2.2]octane-2-carboxylate (racemate) | LC-MS (Method 6):<br>$R_t$ = 1.65 min; m/z = 398/400 (M + H)$^+$. |
| 18A | 2-(4-bromophenyl)-3-(3,8-diazabicyclo[3.2.1]oct-3-ylmethyl)imidazo[1,2-a]pyrimidine dihydrochloride<br>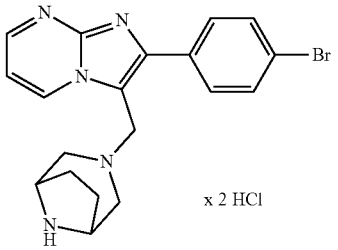<br>x 2 HCl<br>from tert-butyl 3-{[2-(4-bromophenyl)imidazo[1,2-a]pyrimidin-3-yl]methyl}-3,8-diazabicyclo[3.2.1]octane-8-carboxylate | LC-MS (Method 6):<br>$R_t$ = 1.56 min; m/z = 398/400 (M + H)$^+$. |

Example 19A 2-(4-Cyclopropylphenyl)-3-(3,8-diazabicyclo[3.2.1]octan-3-ylmethyl)imidazo[1,2-a]pyrimidine dihydrochloride

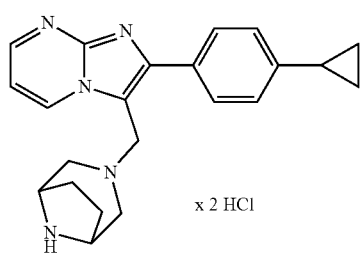 [SMILES: c1cnc2nc(-c3ccc(C4CC4)cc3)c(CN3CC4CCC(C3)N4)n2c1]

tert-Butyl 3-{[2-(4-cyclopropylphenyl)imidazo[1,2-a]pyrimidin-3-yl]methyl}-3,8-diazabicyclo[3.2.1]octane-8-carboxylate (720 mg, 1.57 mmol) was dissolved in 3 ml of dioxane, and 3.92 ml of a 4 M solution of hydrogen chloride in dioxane were added with stirring. The mixture was stirred at room temperature overnight. The reaction solution was then concentrated to dryness and the resulting residue was dried under high vacuum at 40° C. This gave 808 mg of the target product.

LC-MS (Method 1): $R_t$=0.48 min; m/z=360 (M+H)$^+$.

Working Examples

Example 1 tert-Butyl 7-{[2-(4-chlorophenyl)imidazo[1,2-a]pyrimidin-3-yl]methyl}-3-oxa-7,9-diazabicyclo[3.3.1]nonane-9-carboxylate

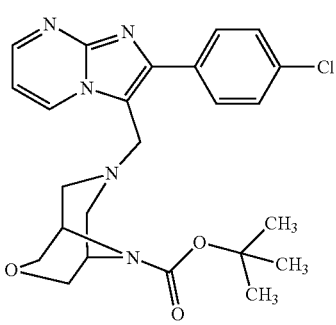 [SMILES: CC(C)(C)OC(=O)N1C2COCC1CN(Cc1c(-c3ccc(Cl)cc3)nc3ncccn13)C2]

Under argon and at room temperature, 2-(4-chlorophenyl)imidazo[1,2-a]pyrimidine-3-carbaldehyde (1.50 g, 5.82 mmol) was dissolved in 25 ml of THF, and tert-butyl 3-oxa-7,9-diazabicyclo[3.3.1]nonane-9-carboxylate (1.59 g, 6.99 mmol) and acetic acid (670 µl, 12 mmol) were added.

Sodium triacetoxyborohydride (1.85 g, 8.73 mmol) was then added a little at a time, and the reaction solution was stirred at room temperature overnight. Then water was gradually and carefully added dropwise (caution: evolution of gas), and subsequently ethyl acetate was added. The resulting organic phase was removed and the aqueous phase was extracted twice with ethyl acetate. The combined organic phases were washed with saturated sodium chloride solution, dried over magnesium sulfate, filtered and concentrated to dryness under reduced pressure on a rotary evaporator. The residue obtained was crystallized from diethyl ether. The crystals formed were filtered off with suction and dried in a high-vacuum drying cabinet at 40° C. overnight. This gave 1.52 g (3.23 mmol, 56% of theory) of the target compound.

LC-MS (Method 2): $R_t$=1.65 min; m/z=470/472 (M+H)$^+$.

$^1$H-NMR (400 MHz, DMSO-d$_6$): δ [ppm]=1.40 (s, 9H), 2.42 (br. d, 2H), 2.87 (br. d, 2H), 3.57 (br. d, 2H), 3.72 (br. dd, 2H), 3.84 (br. d, 2H), 3.92 (s, 2H), 7.08 (dd, 1H), 7.55 (d, 2H), 7.96 (d, 2H), 8.58 (dd, 1H), 9.28 (dd, 1H).

Example 2 tert-Butyl 7-{[2-(4-isopropylphenyl)imidazo[1,2-a]pyrimidin-3-yl]methyl}-3-oxa-7,9-diazabicyclo[3.3.1]nonane-9-carboxylate

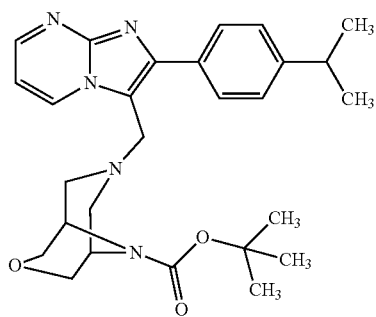 [SMILES: CC(C)c1ccc(-c2nc3ncccn3c2CN2CC3COCC(C2)N3C(=O)OC(C)(C)C)cc1]

Under argon and at room temperature, 2-(4-isopropylphenyl)imidazo[1,2-a]pyrimidine-3-carbaldehyde (500 mg, 1.89 mmol) was dissolved in 10 ml of THF, and tert-butyl 3-oxa-7,9-diazabicyclo[3.3.1]nonane-9-carboxylate (516 mg, 2.26 mmol) and acetic acid (220 μl, 3.77 mmol) were added. Sodium triacetoxyborohydride (599 mg, 2.83 mmol) was then added a little at a time, and the reaction solution was stirred at room temperature overnight. Then water was gradually and carefully added dropwise (caution: evolution of gas), and subsequently ethyl acetate was added. The resulting organic phase was removed and the aqueous phase was extracted twice with ethyl acetate. The combined organic phases were washed with saturated sodium chloride solution, dried over magnesium sulfate, filtered and concentrated to dryness under reduced pressure on a rotary evaporator. The residue obtained was purified by column chromatography (Biotage Isolera, Biotage SNAP-KP-NH column; mobile phase: cyclohexane/ethyl acetate gradient). This gave 431 mg (0.9 mmol, 48% of theory) of the target compound.

LC-MS (Method 2): $R_t$=1.79 min; m/z=478 (M+H)$^+$.

$^1$H-NMR (400 MHz, DMSO-d$_6$): δ [ppm]=1.25 (d, 6H), 1.40 (s, 9H), 2.39 (br. d, 2H), 2.87 (br. d, 2H), 2.90 (m, 1H), 3.57 (br. d, 2H), 3.72 (br. dd, 2H), 3.84 (br. d, 2H), 3.95 (s, 2H), 7.05 (dd, 1H), 7.36 (d, 2H), 7.80 (d, 2H), 8.55 (dd, 1H), 9.27 (dd, 1H).

Example 3 tert-Butyl 5-{[2-(4-chlorophenyl)imidazo[1,2-a]pyrimidin-3-yl]methyl}-2,5-diazabicyclo[2.2.2]octane-2-carboxylate (racemate)

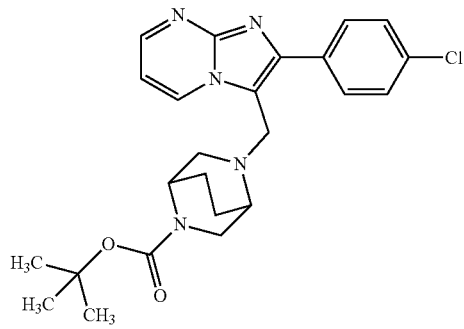 [SMILES: CC(C)(C)OC(=O)N1CC2CCC1CN2Cc1c(-c2ccc(Cl)cc2)nc2ncccn12]

Under argon and at room temperature, 2-(4-chlorophenyl)imidazo[1,2-a]pyrimidine-3-carbaldehyde (4.00 g, 15.5 mmol) was dissolved in 100 ml of THF, and tert-butyl 2,5-diazabicyclo[2.2.2]octane-2-carboxylate (3.95 g, 18.6 mmol) and acetic acid (1.8 ml, 31 mmol) were added. Sodium triacetoxyborohydride (4.93 g, 23.3 mmol) was then added a little at a time, and the reaction solution was stirred at room temperature overnight. Further tert-butyl 2,5-diazabicyclo[2.2.2]octane-2-carboxylate (1.6 g, 7.76 mmol) and sodium triacetoxyborohydride (1.2 g, 5.8 mmol) were then added and the reaction solution was once more stirred at room temperature overnight. Then water was gradually and carefully added dropwise (caution: evolution of gas), and subsequently ethyl acetate was added. The resulting organic phase was removed and the aqueous phase was extracted twice with ethyl acetate. The combined organic phases were dried over magnesium sulfate, filtered and concentrated to dryness under reduced pressure on a rotary evaporator. The residue obtained was purified by column chromatography (Biotage Isolera, Biotage SNAP-KP-NH column; mobile phase: cyclohexane/ethyl acetate gradient). This gave 3.17 g (6.7 mmol, 43% of theory) of the target compound.

LC-MS (Method 2): $R_t$=1.55 min; m/z=454/456 (M+H)$^+$.

Example 4 and Example 5 tert-Butyl 5-{[2-(4-chlorophenyl)imidazo[1,2-a]pyrimidin-3-yl]methyl}-2,5-diazabicyclo[2.2.2]octane-2-carboxylate (Enantiomers 1 and 2)

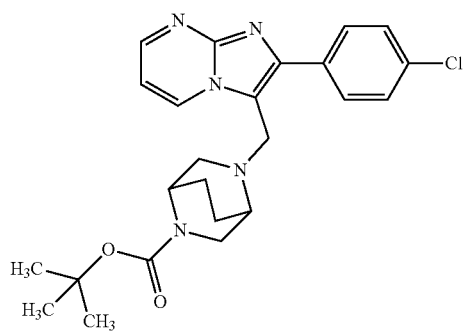 [SMILES: CC(C)(C)OC(=O)N1CC2CCC1CN2Cc1c(-c2ccc(Cl)cc2)nc2ncccn12]

3.17 g (6.70 mmol) of racemic tert-butyl 5-{[2-(4-chlorophenyl)imidazo[1,2-a]pyrimidin-3-yl]methyl}-2,5-diazabicyclo[2.2.2]octane-2-carboxylate (Example 3) were separated into the enantiomers by preparative SFC-HPLC on a chiral phase [column: Daicel Chiralpak OJ-H, 5 µm, 250 mm×30 mm; mobile phase:carbon dioxide/ethanol 85:15 (v/v); flow rate: 150 ml/min; pressure: 135 bar; UV detection: 210 nm; temperature: 38° C.]:

Example 4 (Enantiomer 1)

Yield: 1.29 g
$R_t$=4.15 min; chemical purity >99%; >99% ee
[column: Daicel Chiralpak OJ-H, 3 µm, 100 mm×4.6 mm; mobile phase:carbon dioxide/ethanol 85:15 (v/v); flow rate: 3 ml/min; pressure: 130 bar; temperature: 40° C.; UV detection: 210 nm].
LC-MS (Method 2): $R_t$=1.55 min; m/z=454/456 (M+H)$^+$.
$^1$H-NMR (400 MHz, DMSO-d$_6$): δ [ppm]=1.36 (d, 9H), 1.42-1.55 (m, 1H), 1.57-1.73 (m, 2H), 1.79-1.92 (m, 1H), 2.63-2.80 (m, 3H), 3.09-3.17 (m, 1H), 3.47-3.56 (m, 1H), 3.80 (br. d, 1H), 4.18-4.29 (m, 2H), 7.12 (dd, 1H), 7.56 (d, 2H), 7.84-7.93 (m, 2H), 8.59 (dd, 1H), 9.02 (br. d, 1H).

Example 5 (Enantiomer 2)

Yield: 720 mg
$R_t$=6.6 min; chemical purity >99%; >99% ee
[column: Daicel Chiralpak OJ-H, 3 µm, 100 mm×4.6 mm; mobile phase:carbon dioxide/ethanol 85:15 (v/v); flow rate: 3 ml/min; pressure: 130 bar; temperature: 40° C.; UV detection: 210 nm].
LC-MS (Method 2): $R_t$=1.56 min; m/z=454/456 (M+H)$^+$.
$^1$H-NMR (400 MHz, DMSO-d$_6$): δ [ppm]=1.36 (d, 9H), 1.43-1.55 (m, 1H), 1.57-1.73 (m, 2H), 1.80-1.92 (m, 1H), 2.63-2.80 (m, 3H), 3.14 (br. dd, 1H), 3.47-3.56 (m, 1H), 3.80 (br. d, 1H), 4.18-4.29 (m, 2H), 7.12 (dd, 1H), 7.56 (d, 2H), 7.84-7.94 (m, 2H), 8.59 (dd, 1H), 9.02 (br. d, 1H).

Example 6 tert-Butyl 3-{[2-(4-chlorophenyl)imidazo[1,2-a]pyrimidin-3-yl]methyl}-3,8-diazabicyclo[3.2.1]octane-8-carboxylate

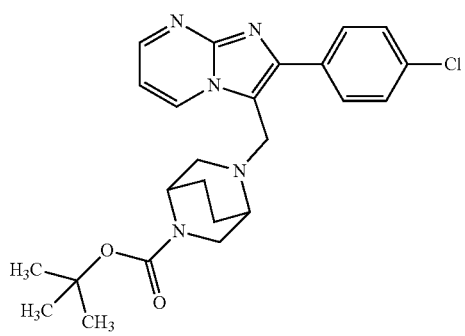

Under argon and at room temperature, 2-(4-chlorophenyl)imidazo[1,2-a]pyrimidine-3-carbaldehyde (1.50 g, 5.82 mmol) was dissolved in 25 ml of THF, and tert-butyl 3,8-diazabicyclo[3.2.1]octane-8-carboxylate (1.48 g, 6.99 mmol) and acetic acid (670 µl, 12 mmol) were added. Sodium triacetoxyborohydride (1.85 g, 8.73 mmol) was then added a little at a time, and the reaction solution was stirred at room temperature overnight. Then water was gradually and carefully added dropwise (caution: evolution of gas), and subsequently ethyl acetate was added. The resulting organic phase was removed and the aqueous phase was extracted twice with ethyl acetate. The combined organic phases were washed with saturated sodium chloride solution, dried over magnesium sulfate, filtered and concentrated to dryness under reduced pressure on a rotary evaporator. The residue obtained was crystallized from diethyl ether. The crystals formed were taken up in acetonitrile and the precipitate that remained was filtered off with suction and dried in a high-vacuum drying cabinet at 40° C. overnight. This gave 840 mg (1.85 mmol, 32% of theory) of the target compound.

LC-MS (Method 2): $R_t$=2.06 min; m/z=454/456 (M+H)$^+$
$^1$H-NMR (400 MHz, DMSO-d$_6$): δ [ppm]=1.39 (s, 9H), 1.64 (br. s, 4H), 2.26 (br. d, 2H), 2.42-2.60 (m, 2H, obscured by DMSO signal), 3.96-4.05 (m, 4H), 7.14 (dd, 1H), 7.56 (d, 2H), 7.95 (d, 2H), 8.59 (dd, 1H), 9.03 (dd, 1H).

Example 7 tert-Butyl 5-{[2-(4-isopropylphenyl)imidazo[1,2-a]pyrimidine-3-yl]methyl}-2,5-diazabicyclo[2.2.2]octane-2-carboxylate (racemate)

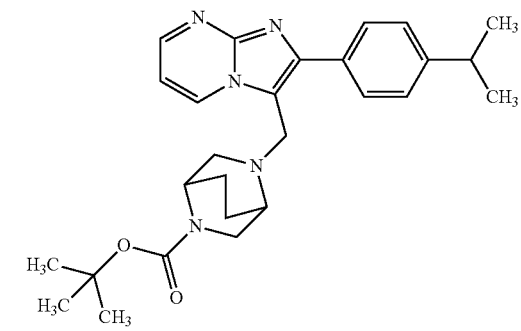 [SMILES: CC(C)c1ccc(-c2nc3ncccn3c2CN2CC3CCC2CN3C(=O)OC(C)(C)C)cc1]

Under argon and at room temperature, 2-(4-isopropylphenyl)imidazo[1,2-a]pyrimidine-3-carbaldehyde (1.50 g, 5.65 mmol) was dissolved in 20 ml of THF, and tert-butyl 2,5-diazabicyclo[2.2.2]octane-2-carboxylate (racemate; 1.44 g, 6.78 mmol) and acetic acid (650 µl, 11.31 mmol) were added. Sodium triacetoxyborohydride (1.8 g, 8.48 mmol) was then added a little at a time, and the reaction solution was stirred at room temperature overnight. Then water was gradually and carefully added dropwise (caution: evolution of gas), and subsequently ethyl acetate was added. The resulting organic phase was removed and the aqueous phase was extracted twice with ethyl acetate. The combined organic phases were washed with saturated sodium chloride solution, dried over magnesium sulfate, filtered and concentrated to dryness under reduced pressure on a rotary evaporator. The residue obtained was purified by column chromatography (Biotage Isolera, Biotage SNAP-KP-NH column; mobile phase: cyclohexane/ethyl acetate gradient). This gave 1760 mg (3.81 mmol, 67% of theory) of the target compound.

LC-MS (Method 2): $R_t$=1.71 min; m/z=462 (M+H)$^+$.

Example 8 and Example 9 tert-Butyl 5-{[2-(4-isopropylphenyl)imidazo[1,2-a]pyrimidin-3-yl]methyl}-2,5-diazabicyclo[2.2.2]octane-2-carboxylate (Enantiomers 1 and 2)

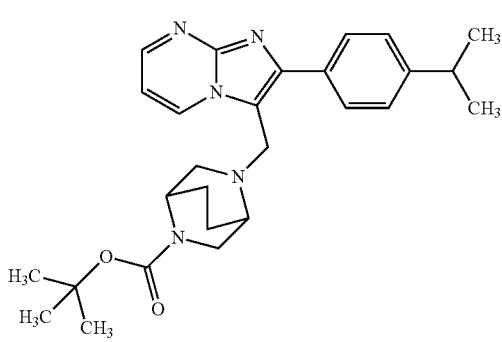 [SMILES: CC(C)c1ccc(-c2nc3ncccn3c2CN2CC3CCC2CN3C(=O)OC(C)(C)C)cc1]

1.66 g (3.59 mmol) of racemic tert-butyl 5-{[2-(4-isopropylphenyl)imidazo[1,2-a]pyrimidin-3-yl]methyl}-2,5-diazabicyclo[2.2.2]octane-2-carboxylate (Example 7) were separated into the enantiomers by preparative SFC-HPLC on a chiral phase [column: Daicel Chiralpak OX—H (SFC), 5 µm, 250 mm×30 mm; mobile phase:carbon dioxide/methanol 62:38 (v/v); flow rate: 80 g/min; pressure: 120 bar; UV detection: 210 nm; temperature: 38° C.]:

Example 8 (Enantiomer 1)

Yield: 774 mg $R_t$=4.91 min; chemical purity >99%; >99% ee

[column: Daicel Chiralpak OX-3 (SFC), 3 µm, 100 mm×4.6 mm; mobile phase:carbon dioxide/ethanol 70:30 (v/v); flow rate: 3 ml/min; pressure: 130 bar; temperature: 40° C.; UV detection: 210 nm].

LC-MS (Method 1): $R_t$=0.85 min; m/z=462 (M+H)$^+$.

$[\alpha]_D^{20}$=+16.21° (c=0.270, Methanol).

$^1$H-NMR (400 MHz, DMSO-$d_6$): δ [ppm]=1.25 (d, 6H), 1.36 (2s, 9H), 1.44-1.56 (m, 1H), 1.66 (br. s, 2H), 1.79-1.95 (m, 1H), 2.65-2.83 (m, 3H), 2.89-3.03 (m, 1H), 3.09-3.20 (m, 1H), 3.53 (br. d, 1H), 3.81 (br. d, 1H), 4.24 (s, 2H), 7.10 (dd, 1H), 7.37 (d, 2H), 7.78 (dd, 2H), 8.56 (dd, 1H), 8.99 (br. d, 1H).

Example 9 (Enantiomer 2)

Yield: 734 mg $R_t$=6.88 min; chemical purity >99%; >99% ee

[column: Daicel Chiralpak OX-3 (SFC), 3 µm, 100 mm×4.6 mm; mobile phase:carbon dioxide/ethanol 70:30 (v/v); flow rate: 3 ml/min; pressure: 130 bar; temperature: 40° C.; UV detection: 210 nm].

LC-MS (Method 1): $R_t$=0.85 min; m/z=462 (M+H)$^+$.

$[\alpha]_D^{20}$=−15.67° (c=0.270, Methanol).

$^1$H-NMR (400 MHz, DMSO-$d_6$): δ [ppm]=1.25 (d, 6H), 1.36 (2s, 9H), 1.44-1.56 (m, 1H), 1.66 (br. s, 2H), 1.79-1.94 (m, 1H), 2.64-2.83 (m, 3H), 2.95 (dt, 1H), 3.09-3.20 (m, 1H), 3.53 (br. d, 1H), 3.81 (br. d, 1H), 4.24 (s, 2H), 7.10 (dd, 1H), 7.37 (d, 2H), 7.78 (dd, 2H), 8.56 (dd, 1H), 8.99 (br. d, 1H).

Example 10 tert-Butyl 3-{1-[2-(4-chlorophenyl)imidazo[1,2-a]pyrimidin-3-yl]ethyl}-3,8-diazabicyclo[3.2.1]octane-8-carboxylate (racemate)

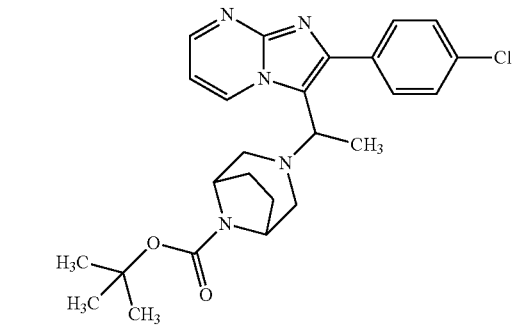 [SMILES: CC(c1c(-c2ccc(Cl)cc2)nc2ncccn12)N1CC2CCC(C1)N2C(=O)OC(C)(C)C]

1-[2-(4-Chlorophenyl)imidazo[1,2-a]pyrimidin-3-yl]ethanol (473 mg, 1.73 mmol) and triphenylphosphine (906 mg, 3.46 mmol) were initially charged in 10 ml of dichloromethane, and carbon tetrabromide (1.15 g, 3.46 mmol) was added a little at a time with cooling (ice bath). Triethylamine (480 µl, 3.5 mmol) was then added, and the mixture was stirred at room temperature for 1 h. The mixture was then concentrated by evaporation and the residue was dissolved in 10 ml of acetonitrile. tert-Butyl 3,8-diazabicyclo[3.2.1]octane-8-carboxylate (734 mg, 3.46 mmol) was added, and the reaction mixture was stirred at 40° C. overnight. The mixture was then once more concentrated to dryness. 400 mg of the residue obtained in this manner were directly separated into the components by preparative HPLC (Method 8). The remainder of the residue was applied to silica gel and pre-purified by column chromatography (Biotage Isolera, Biotage SNAP-KP-NH column, mobile phase cyclohexane/ethyl acetate gradient). The product thus pre-purified was then re-purified by preparative HPLC (Method 8). This gave 50 mg (0.11 mmol, 6% of theory) of the title compound.

LC-MS (Method 2): $R_t$=2.14 min; MS (ESIpos): m/z=468/470 [M+H]$^+$.

Analogously to Examples 1-3 and 6-7, the following compounds were prepared from the starting materials specified in each case:

| Example | Name/Structure/Starting materials | Analytical data |
|---|---|---|
| 11 | tert-butyl 5-{[2-(4-bromophenyl)imidazo[1,2-a]pyrimidin-3-yl]methyl}-2,5-diazabicyclo[2.2.2]octane-2-carboxylate (racemate)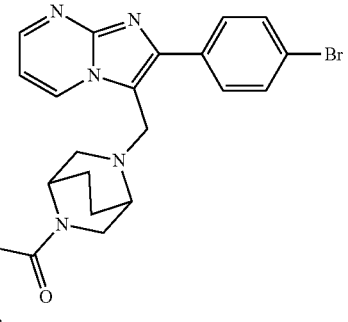from tert-butyl 2,5-diazabicyclo[2.2.2]octane-2-carboxylate (racemate) and 2-(4-bromophenyl)imidazo[1,2-a]pyrimidine-3-carbaldehyde | $^1$H-NMR (400 MHz, DMSO-$d_6$): δ [ppm] = −0.149 (0.44), −0.008 (3.64), 0.008 (3.55), 0.146 (0.45), 1.345 (14.48), 1.374 (16.00), 1.402 (4.45), 1.489 (0.55), 1.654 (0.95), 1.859 (0.54), 2.328 (0.58), 2.670 (1.91), 2.709 (1.58), 2.774 (0.64), 3.118 (0.57), 3.146 (0.65), 3.155 (0.60), 3.515 (0.56), 3.774 (0.61), 3.827 (0.68), 4.235 (4.16), 5.754 (5.06), 7.108 (1.24), 7.119 (1.32), 7.125 (1.31), 7.136 (1.29), 7.679 (3.52), 7.700 (4.83), 7.812 (1.99), 7.824 (1.97), 7.833 (1.62), 7.845 (1.39), 8.579 (1.48), 8.584 (1.62), 8.590 (1.53), 8.594 (1.45), 9.013 (1.24), 9.030 (1.21).<br>LC-MS (Method 2):<br>$R_t$ = 1.68 min; m/z = 498/500 (M + H)$^+$. |
| 12 | tert-butyl 3-{[2-(4-bromophenyl)imidazo[1,2-a]pyrimidin-3-yl]methyl}-3,8-diazabicyclo[3.2.1]octane-2-carboxylate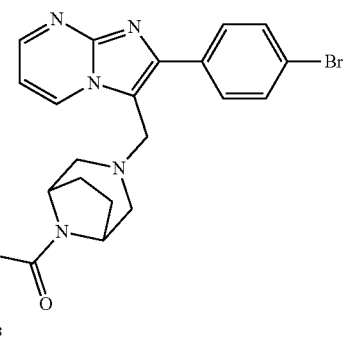from tert-butyl 3,8-diazabicyclo[3.2.1]octane-8-carboxylate and 2-(4-bromophenyl)imidazo[1,2-a]pyrimidine-3-carbaldehyde | $^1$H-NMR (400 MHz, DMSO-$d_6$): δ [ppm] = 1.39 (s, 9H), 1.56-1.73 (m, 4H), 2.26 (br. d, 2H), 2.46-2.60 (m, 2H, obscured by DMSO signal), 3.98 (s, 2H), 4.02 (br. s, 2H), 7.14 (dd, 1H), 7.70 (d, 2H), 7.88 (d, 2H), 8.59 (dd, 1H), 9.03 (dd, 1H).<br>LC-MS (Method 5):<br>$R_t$ = 1.42 min; m/z = 498/500 (M + H)$^+$. |

Example 13

(7-{[2-(4-Chlorophenyl)imidazo[1,2-a]pyrimidin-3-yl]methyl}-3-oxa-7,9-diazabicyclo[3.3.1]non-9-yl)(6-methoxypyridin-2-yl)methanone

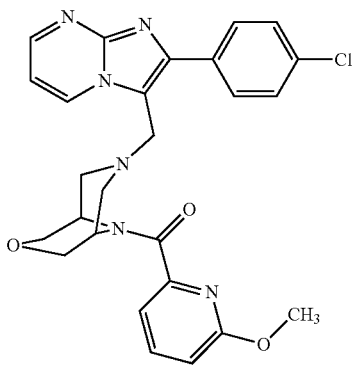 [SMILES: COc1cccc(C(=O)N2C3COCC2CN(Cc2c(-c4ccc(Cl)cc4)nc4ncccn24)C3)n1]

6-Methoxypyridine-2-carboxylic acid (35.1 mg, 230 µmol) was dissolved in 1.5 ml of DMF, 2-(7-aza-1H-benzotriazol-1-yl)-1,1,3,3-tetramethyluronium hexafluorophosphate (HATU) (119 mg, 313 µmol) was added and the mixture was stirred at room temperature for 30 min. 7-{[2-(4-Chlorophenyl)imidazo[1,2-a]pyrimidin-3-yl]methyl}-3-oxa-7,9-diazabicyclo[3.3.1]nonane dihydrochloride (100 mg) and N,N-diisopropylethylamine (180 µl, 1.0 mmol) were then added and the mixture was stirred at room temperature overnight. Thereafter, the reaction mixture was separated directly into its components via preparative HPLC (Method 8). 74 mg (0.15 mmol, 70% of theory) of the title compound were obtained.

LC-MS (Method 2): $R_t$=1.48 min; m/z=505/507 (M+H)$^+$.
$^1$H-NMR (400 MHz, DMSO-$d_6$): δ [ppm]=2.46-2.66 (m, 2H, partially obscured by DMSO signal), 2.91 (br. d, 1H), 3.05 (br. d, 1H), 3.66-3.83 (m, 3H), 3.80 (s, 3H), 3.89 (d, 1H), 3.93-4.03 (m, 2H), 4.20 (br. s, 1H), 4.44 (br. s, 1H), 6.93 (d, 1H), 7.09 (dd, 1H), 7.29 (d, 1H), 7.54 (d, 2H), 7.83 (t, 1H), 7.97 (d, 2H), 8.58 (dd, 1H), 9.28 (dd, 1H).

Example 14

(3-Chloro-6-methoxypyridin-2-yl)(7-{[2-(4-chlorophenyl)imidazo[1,2-a]pyrimidin-3-yl]methyl}-3-oxa-7,9-diazabicyclo[3.3.1]non-9-yl)methanone

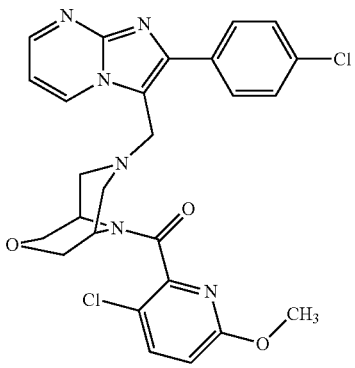 [SMILES: COc1ccc(Cl)c(C(=O)N2C3COCC2CN(Cc2c(-c4ccc(Cl)cc4)nc4ncccn24)C3)n1]

3-Chloro-6-methoxypyridine-2-carboxylic acid (43.1 mg, 230 μmol) was dissolved in 1.5 ml of DMF, 2-(7-aza-1H-benzotriazol-1-yl)-1,1,3,3-tetramethyluronium hexafluorophosphate (HATU) (119 mg, 313 μmol) was added and the mixture was stirred at room temperature for 30 min. 7-{[2-(4-Chlorophenyl)imidazo[1,2-a]pyrimidin-3-yl]methyl}-3-oxa-7,9-diazabicyclo[3.3.1]nonane dihydrochloride (100 mg) and N,N-diisopropylethylamine (180 μl, 1.0 mmol) were then added and the mixture was stirred at room temperature overnight. Thereafter, the reaction mixture was separated directly into its components via preparative HPLC (Method 8). 78 mg (0.15 mmol, 70% of theory) of the title compound were obtained.

LC-MS (Method 1): $R_t$=0.86 min; m/z=539/541 (M+H)$^+$.

Example 15

(7-{[2-(4-Chlorophenyl)imidazo[1,2-a]pyrimidin-3-yl]methyl}-3-oxa-7,9-diazabicyclo[3.3.1]non-9-yl)(3-fluoro-6-methoxypyridin-2-yl)methanone

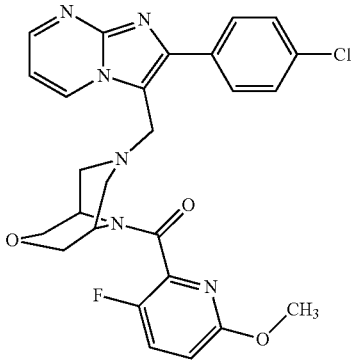 [SMILES: COc1ccc(F)c(C(=O)N2C3COCC2CN(Cc2c(-c4ccc(Cl)cc4)nc4ncccn24)C3)n1]

3-Fluoro-6-methoxypyridine-2-carboxylic acid (39.3 mg, 230 μmol) was dissolved in 1.5 ml of DMF, 2-(7-aza-1H-benzotriazol-1-yl)-1,1,3,3-tetramethyluronium hexafluorophosphate (HATU) (119 mg, 313 μmol) was added and the mixture was stirred at room temperature for 30 min. 7-{[2-(4-Chlorophenyl)imidazo[1,2-a]pyrimidin-3-yl]methyl}-3-oxa-7,9-diazabicyclo[3.3.1]nonane dihydrochloride (100 mg) and N,N-diisopropylethylamine (180 μl, 1.0 mmol) were then added and the mixture was stirred at room temperature overnight. Thereafter, the reaction mixture was separated directly into its components via preparative HPLC (Method 8). 82 mg (0.16 mmol, 76% of theory) of the title compound were obtained.

LC-MS (Method 1): $R_t$=0.82 min; m/z=523/525 (M+H)$^+$.

$^1$H-NMR (400 MHz, DMSO-d$_6$): δ [ppm]=2.45-2.60 (m, 2H, obscured by DMSO signal), 2.90 (br. d, 1H), 3.05 (br. d, 1H), 3.58-3.70 (m, 3H), 3.72-3.84 (m, 1H), 3.80 (s, 3H), 3.89 (d, 1H), 3.98 (s, 2H), 4.45 (br. s, 1H), 6.97 (dd, 1H), 7.08 (dd, 1H), 7.55 (d, 2H), 7.80 (t, 1H), 7.97 (d, 2H), 8.58 (dd, 1H), 9.28 (dd, 1H).

Example 16

(7-{[2-(4-Chlorophenyl)imidazo[1,2-a]pyrimidin-3-yl]methyl}-3-oxa-7,9-diazabicyclo[3.3.1]non-9-yl)[6-(methylsulfanyl)pyridin-2-yl]methanone

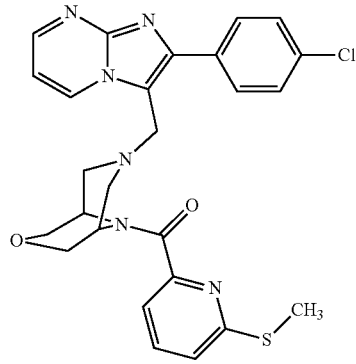 [SMILES: CSc1cccc(C(=O)N2C3COCC2CN(Cc2c(-c4ccc(Cl)cc4)nc4ncccn24)C3)n1]

6-(Methylsulfanyl)pyridine-2-carboxylic acid (38.8 mg, 230 μmol) was dissolved in 1.5 ml of DMF, 2-(7-aza-1H-benzotriazol-1-yl)-1,1,3,3-tetramethyluronium hexafluorophosphate (HATU) (119 mg, 313 μmol) was added and the mixture was stirred at room temperature for 30 min. 7-{[2-(4-Chlorophenyl)imidazo[1,2-a]pyrimidin-3-yl]methyl}-3-oxa-7,9-diazabicyclo[3.3.1]nonane dihydrochloride (100 mg) and N,N-diisopropylethylamine (180 μl, 1.0 mmol) were then added and the mixture was stirred at room temperature overnight. Thereafter, the reaction mixture was separated directly into its components via preparative HPLC (Method 8). 84 mg (0.16 mmol, 77% of theory) of the title compound were obtained.

LC-MS (Method 1): $R_t$=0.85 min; m/z=521/523 (M+H)$^+$.

$^1$H-NMR (400 MHz, DMSO-d$_6$): δ [ppm]=2.46 (s, 3H), 2.56-2.65 (m, 2H), 2.91 (br. d, 1H), 3.06 (br. d, 1H), 3.65-3.81 (m, 3H), 3.86-4.03 (m, 3H), 4.15 (br. s, 1H), 4.46 (br. s, 1H), 7.09 (dd, 1H), 7.40 (dd, 2H), 7.55 (d, 2H), 7.77 (t, 1H), 7.98 (d, 2H), 8.58 (dd, 1H), 9.28 (dd, 1H).

Example 17

(7-{[2-(4-Chlorophenyl)imidazo[1,2-a]pyrimidin-3-yl]methyl}-3-oxa-7,9-diazabicyclo[3.3.1]non-9-yl)(cyclopentyl)methanone

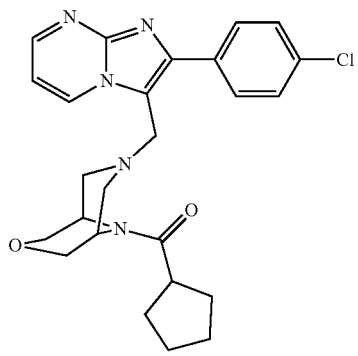 [SMILES: O=C(C1CCCC1)N1C2COCC1CN(Cc1c(-c3ccc(Cl)cc3)nc3ncccn13)C2]

Cyclopentanecarboxylic acid (18 μl, 230 μmol) was dissolved in 1.5 ml of DMF, 2-(7-aza-1H-benzotriazol-1-yl)-1,1,3,3-tetramethyluronium hexafluorophosphate (HATU) (119 mg, 313 μmol) was added and the mixture was stirred at room temperature for 30 min. 7-{[2-(4-Chlorophenyl)imidazo[1,2-a]pyrimidin-3-yl]methyl}-3-oxa-7,9-diazabicyclo[3.3.1]nonane dihydrochloride (100 mg) and N,N-diisopropylethylamine (180 μl, 1.0 mmol) were then added and the mixture was stirred at room temperature overnight. Thereafter, the reaction mixture was separated directly into its components via preparative HPLC (Method 8). 72 mg (0.15 mmol, 74% of theory) of the title compound were obtained.

LC-MS (Method 1): $R_t$=0.81 min; m/z=466/468 (M+H)$^+$.

$^1$H-NMR (400 MHz, DMSO-d$_6$): δ [ppm]=1.43-1.81 (m, 8H), 2.31-2.61 (m, 2H, partially obscured by DMSO signal), 2.86-2.97 (m, 3H), 3.47-3.54 (m, 1H), 3.56-3.63 (m, 1H), 3.77 (dd, 2H), 3.94 (s, 2H), 4.04 (br. s, 1H), 4.32 (br. s, 1H), 7.08 (dd, 1H), 7.55 (d, 2H), 7.97 (d, 2H), 8.59 (dd, 1H), 9.27 (dd, 1H).

Example 18

(3-Fluoro-6-methoxypyridin-2-yl)(7-{[2-(4-isopropylphenyl)imidazo[1,2-a]pyrimidin-3-yl]methyl}-3-oxa-7,9-diazabicyclo[3.3.1]non-9-yl)methanone

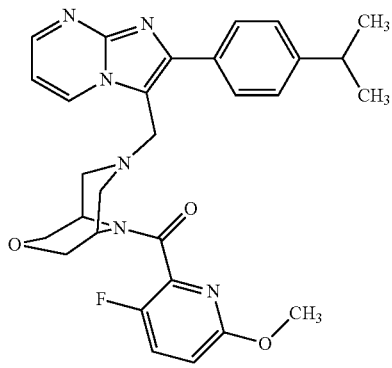 [SMILES: COc1ccc(F)c(C(=O)N2C3COCC2CN(Cc2c(-c4ccc(C(C)C)cc4)nc4ncccn24)C3)n1]

3-Fluoro-6-methoxypyridine-2-carboxylic acid (39 mg, 0.23 mmol) was dissolved in 1.5 ml of DMF, 2-(7-aza-1H-benzotriazol-1-yl)-1,1,3,3-tetramethyluronium hexafluorophosphate (HATU) (117 mg, 0.31 mmol) was added and the mixture was stirred at room temperature for 30 min. 7-{[2-(4-Isopropylphenyl)imidazo[1,2-a]pyrimidin-3-yl]methyl}-3-oxa-7,9-diazabicyclo[3.3.1]nonane dihydrochloride (100 mg) and N,N-diisopropylethylamine (180 μl, 1.0 mmol) were then added and the mixture was stirred at room temperature overnight. Thereafter, the reaction mixture was separated directly into its components via preparative HPLC (Method 8). 83 mg (0.16 mmol, 76% of theory) of the title compound were obtained.

LC-MS (Method 1): $R_t$=0.84 min; m/z=531 (M+H)$^+$.

$^1$H-NMR (400 MHz, DMSO-d$_6$): δ [ppm]=1.26 (d, 6H), 2.46-2.58 (m, 2H, obscured by DMSO signal), 2.86-3.01 (m, 2H), 3.06 (br. d, 1H), 3.57-3.70 (m, 3H), 3.75 (br. d, 1H), 3.79 (s, 3H), 3.89 (d, 1H), 3.99 (s, 2H), 4.46 (br. s, 1H), 6.97 (dd, 1H), 7.06 (dd, 1H), 7.36 (d, 2H), 7.74-7.84 (m, 3H), 8.55 (dd, 1H), 9.26 (dd, 1H).

Example 19

[6-(Difluoromethoxy)pyridin-2-yl](7-{[2-(4-isopropylphenyl)imidazo[1,2-a]pyrimidin-3-yl]methyl}-3-oxa-7,9-diazabicyclo[3.3.1]non-9-yl)methanone

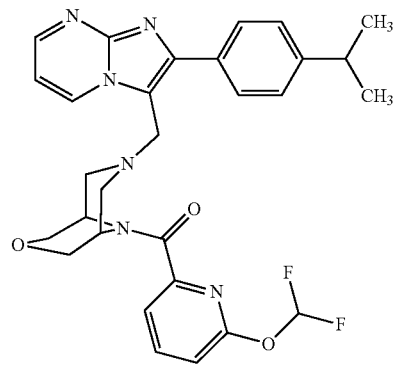 [SMILES: CC(C)c1ccc(-c2nc3ncccn3c2CN2CC3COCC(C2)N3C(=O)c2cccc(OC(F)F)n2)cc1]

6-(Difluoromethoxy)pyridine-2-carboxylic acid (43 mg, 0.23 mmol) was dissolved in 1.5 ml of DMF, 2-(7-aza-1H-benzotriazol-1-yl)-1,1,3,3-tetramethyluronium hexafluorophosphate (HATU) (117 mg, 0.31 mmol) was added and the mixture was stirred at room temperature for 30 min. 7-{[2-(4-Isopropylphenyl)imidazo[1,2-a]pyrimidin-3-yl]methyl}-3-oxa-7,9-diazabicyclo[3.3.1]nonane dihydrochloride (100 mg) and N,N-diisopropylethylamine (180 μl, 1.0 mmol) were then added and the mixture was stirred at room temperature overnight. Thereafter, the reaction mixture was separated directly into its components via preparative HPLC (Method 8). 72 mg (0.13 mmol, 61% of theory) of the title compound were obtained.

LC-MS (Method 1): $R_t$=0.89 min; m/z=549 (M+H)$^+$.

$^1$H-NMR (400 MHz, DMSO-d$_6$): δ [ppm]=1.25 (d, 6H), 2.45-2.64 (m, 3H, partially obscured by DMSO signal), 2.86-2.99 (m, 2H), 3.05 (br. d, 1H), 3.65-3.79 (m, 3H), 3.89 (d, 1H), 4.00 (s, 2H), 4.09 (br. s, 1H), 4.44 (br. s, 1H), 7.06 (dd, 1H), 7.21 (d, 1H), 7.36 (d, 2H), 7.54-7.62 (m, 1H), 7.81 (d, 2H), 8.06 (t, 1H), 8.55 (dd, 1H), 9.28 (dd, 1H).

Example 20

(3-{[2-(4-Chlorophenyl)imidazo[1,2-a]pyrimidin-3-yl]methyl}-3,8-diazabicyclo[3.2.1]oct-8-yl)(6-methoxypyridin-2-yl)methanone

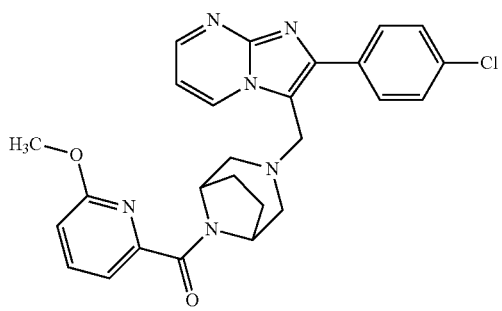 [SMILES: COc1cccc(C(=O)N2C3CCC2CN(Cc2c(-c4ccc(Cl)cc4)nc4ncccn24)C3)n1]

6-Methoxypyridine-2-carboxylic acid (36.4 mg, 237 µmol) was dissolved in 1.5 ml of DMF, 2-(7-aza-1H-benzotriazol-1-yl)-1,1,3,3-tetramethyluronium hexafluorophosphate (HATU) (119 mg, 313 µmol) was added and the mixture was stirred at room temperature for 30 min. 2-(4-Chlorophenyl)-3-(3,8-diazabicyclo[3.2.1]oct-3-ylmethyl)imidazo[1,2-a]pyrimidine dihydrochloride (100 mg) and N,N-diisopropylethylamine (190 µl, 1.1 mmol) were then added and the mixture was stirred at room temperature overnight. Thereafter, the reaction mixture was separated directly into its components via preparative HPLC (Method 8). 79 mg (0.16 mmol, 74% of theory) of the title compound were obtained.

LC-MS (Method 1): $R_t$=1.76 min; m/z=489/491 (M+H)$^+$.

$^1$H-NMR (400 MHz, DMSO-$d_6$): δ [ppm]=1.63-1.84 (m, 4H), 2.45 (br. d, 1H), 2.56-2.65 (m, 2H), 2.73 (dd, 1H), 3.77 (s, 3H), 4.00-4.12 (m, 2H), 4.67 (br. d, 2H), 6.93 (d, 1H), 7.15 (dd, 1H), 7.35 (d, 1H), 7.57 (d, 2H), 7.82 (t, 1H), 7.96 (d, 2H), 8.59 (dd, 1H), 9.06 (dd, 1H).

Example 21

(3-Chloro-6-methoxypyridin-2-yl)(3-{[2-(4-chlorophenyl)imidazo[1,2-a]pyrimidin-3-yl]methyl}-3,8-diazabicyclo[3.2.1]oct-8-yl)methanone

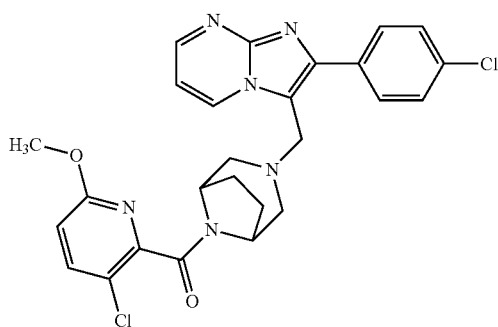 [SMILES: COc1ccc(Cl)c(C(=O)N2C3CCC2CN(Cc2c(-c4ccc(Cl)cc4)nc4ncccn24)C3)n1]

3-Chloro-6-methoxypyridine-2-carboxylic acid (44.5 mg, 237 µmol) was dissolved in 1.5 ml of DMF, 2-(7-aza-1H-benzotriazol-1-yl)-1,1,3,3-tetramethyluronium hexafluorophosphate (HATU) (119 mg, 313 µmol) was added and the mixture was stirred at room temperature for 30 min. 2-(4-Chlorophenyl)-3-(3,8-diazabicyclo[3.2.1]oct-3-ylmethyl)imidazo[1,2-a]pyrimidine dihydrochloride (100 mg) and N,N-diisopropylethylamine (190 µl, 1.1 mmol) were then added and the mixture was stirred at room temperature overnight. Thereafter, the reaction mixture was separated directly into its components via preparative HPLC (Method 8). 56 mg (0.11 mmol, 49% of theory) of the title compound were obtained.

LC-MS (Method 2): $R_t$=1.81 min; m/z=523/524/525 (M+H)$^+$.

$^1$H-NMR (400 MHz, DMSO-$d_6$): δ [ppm]=1.62-1.82 (m, 4H), 2.34-2.46 (m, 2H), 2.47-2.59 (m, 1H, obscured by DMSO signal), 2.69-2.78 (m, 1H), 3.62 (br. s, 1H), 3.79 (s, 3H), 4.06 (s, 2H), 4.59 (br. s, 1H), 6.92 (d, 1H), 7.15 (dd, 1H), 7.57 (d, 2H), 7.87 (d, 1H), 7.94 (d, 2H), 8.59 (dd, 1H), 9.04 (dd, 1H).

Example 22

(3-{[2-(4-Chlorophenyl)imidazo[1,2-a]pyrimidin-3-yl]methyl}-3,8-diazabicyclo[3.2.1]oct-8-yl)(3-fluoro-6-methoxypyridin-2-yl)methanone

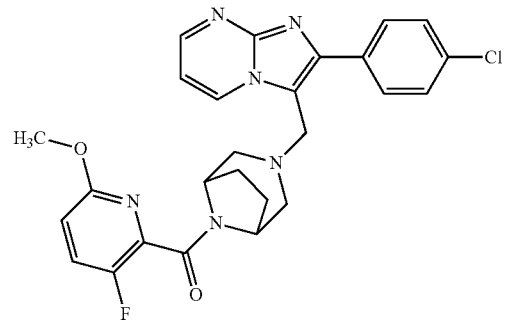 [SMILES: COc1ccc(F)c(C(=O)N2C3CCC2CN(Cc2c(-c4ccc(Cl)cc4)nc4ncccn24)C3)n1]

3-Fluoro-6-methoxypyridine-2-carboxylic acid (40.6 mg, 237 µmol) was dissolved in 1.5 ml of DMF, 2-(7-aza-1H-benzotriazol-1-yl)-1,1,3,3-tetramethyluronium hexafluorophosphate (HATU) (123 mg, 324 µmol) was added and the mixture was stirred at room temperature for 30 min. 2-(4-Chlorophenyl)-3-(3,8-diazabicyclo[3.2.1]oct-3-ylmethyl)imidazo[1,2-a]pyrimidine dihydrochloride (100 mg) and N,N-diisopropylethylamine (190 µl, 1.1 mmol) were then added and the mixture was stirred at room temperature overnight. Thereafter, the reaction mixture was separated directly into its components via preparative HPLC (Method 8). 93 mg (0.18 mmol, 85% of theory) of the title compound were obtained.

LC-MS (Method 2): $R_t$=1.73 min; m/z=507/509 (M+H)$^+$.

$^1$H-NMR (400 MHz, DMSO-$d_6$): δ [ppm]=1.62-1.83 (m, 4H), 2.44 (br. t, 2H), 2.48-2.58 (m, 1H, partially obscured by DMSO signal), 2.75 (dd, 1H), 3.76 (s, 3H), 3.92 (br. s, 1H), 4.01-4.12 (m, 2H), 4.61 (br. s, 1H), 6.95 (dd, 1H), 7.14 (dd, 1H), 7.57 (d, 2H), 7.77 (t, 1H), 7.95 (d, 2H), 8.59 (dd, 1H), 9.06 (dd, 1H).

Example 23

(3-Chloro-6-methoxypyridin-2-yl)(5-{[2-(4-chloro-phenyl)imidazo[1,2-a]pyrimidin-3-yl]methyl}-2,5-diazabicyclo[2.2.2]oct-2-yl)methanone (Enantiomer 1)

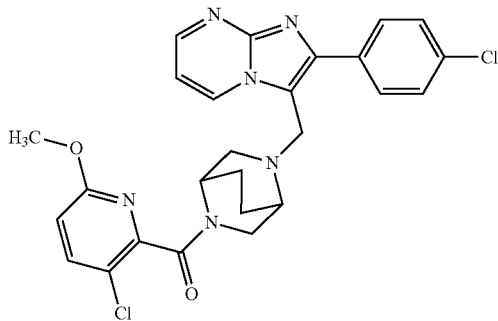 [SMILES: COc1ccc(Cl)c(C(=O)N2CC3CCC2CN3Cc2c(-c3ccc(Cl)cc3)nc3ncccn23)n1]

3-Chloro-6-methoxypyridine-2-carboxylic acid (44.5 mg, 237 μmol) was dissolved in 1.5 ml of DMF, 2-(7-aza-1H-benzotriazol-1-yl)-1,1,3,3-tetramethyluronium hexafluorophosphate (HATU) (123 mg, 324 μmol) was added and the mixture was stirred at room temperature for 30 min. 2-(4-Chlorophenyl)-3-(2,5-diazabicyclo[2.2.2]oct-2-ylmethyl)imidazo[1,2-a]pyrimidine dihydrochloride (Enantiomer 1; 100 mg) and N,N-diisopropylethylamine (190 μl, 1.1 mmol) were then added and the mixture was stirred at room temperature overnight. Thereafter, the reaction mixture was separated directly into its components via preparative HPLC (Method 8). 87 mg (0.16 mmol, 74% of theory) of the title compound were obtained.

LC-MS (Method 2): $R_t$=1.62 min; m/z=523/524/525 (M+H)$^+$.

$^1$H-NMR (400 MHz, DMSO-d$_6$): δ [ppm]=1.52-2.00 (m, 4H), 2.57-3.24 (m, 3.75H), 3.35-3.46 (m, 1.25H), 3.70-3.86 (m, 3.75H), 4.20-4.40 (m, 2.25H), 6.84-6.96 (m, 1H), 7.08-7.19 (m, 1H), 7.49-7.61 (m, 2H), 7.79-7.93 (m, 3H), 8.56-8.64 (m, 1H), 8.98-9.07 (m, 1H).

Example 24

(5-{[2-(4-Chlorophenyl)imidazo[1,2-a]pyrimidin-3-yl]methyl}-2,5-diazabicyclo[2.2.2]oct-2-yl)(3-fluoro-6-methoxypyridin-2-yl)methanone (Enantiomer 2)

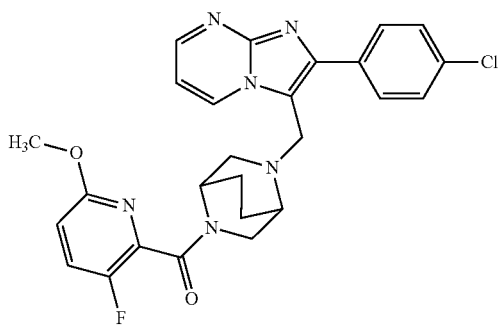 [SMILES: COc1ccc(F)c(C(=O)N2CC3CCC2CN3Cc2c(-c3ccc(Cl)cc3)nc3ncccn23)n1]

3-Fluoro-6-methoxypyridine-2-carboxylic acid (40.6 mg, 237 μmol) was dissolved in 1.5 ml of DMF, 2-(7-aza-1H-benzotriazol-1-yl)-1,1,3,3-tetramethyluronium hexafluorophosphate (HATU) (123 mg, 324 μmol) was added and the mixture was stirred at room temperature for 30 min. 2-(4-Chlorophenyl)-3-(2,5-diazabicyclo[2.2.2]oct-2-ylmethyl)imidazo[1,2-a]pyrimidine dihydrochloride (Enantiomer 2; 100 mg) and N,N-diisopropylethylamine (190 μl, 1.1 mmol) were then added and the mixture was stirred at room temperature overnight. Thereafter, the reaction mixture was separated directly into its components via preparative HPLC (Method 8). 84 mg (0.17 mmol, 77% of theory) of the title compound were obtained.

LC-MS (Method 6): $R_t$=1.52 min; MS (ESIpos): m/z=507/509 [M+H]$^+$.

$^1$H-NMR (400 MHz, DMSO-d$_6$): δ [ppm]=1.50-2.00 (m, 4H), 2.62-2.87 (m, 2.25H), 2.92 (br. s, 0.75H), 3.15 (br. d, 0.25H), 3.38-3.50 (m, 1.5H), 3.56 (br. d, 0.25H), 3.70-3.83 (m, 3.75H), 4.20-4.35 (m, 2H), 4.38 (br. s, 0.25H), 6.89-6.99 (m, 1H), 7.07-7.17 (m, 1H), 7.49-7.60 (m, 2H), 7.70-7.83 (m, 1H), 7.84-7.95 (m, 2H), 8.56-8.63 (m, 1H), 8.99-9.09 (m, 1H).

Example 25

(5-{[2-(4-Chlorophenyl)imidazo[1,2-a]pyrimidin-3-yl]methyl}-2,5-diazabicyclo[2.2.2]oct-2-yl)(6-methoxy-3-methylpyridin-2-yl)methanone (Enantiomer 1)

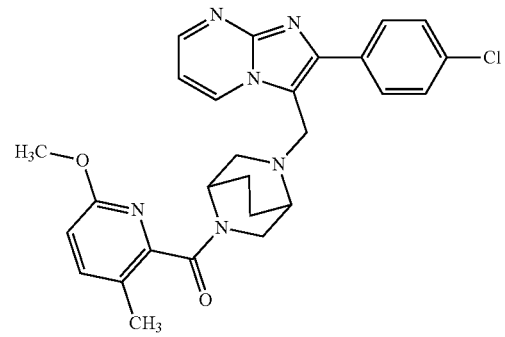 [SMILES: COc1ccc(C)c(C(=O)N2CC3CCC2CN3Cc2c(-c3ccc(Cl)cc3)nc3ncccn23)n1]

6-Methoxy-3-methylpyridine-2-carboxylic acid (39.7 mg, 237 μmol) was dissolved in 1.5 ml of DMF, 2-(7-aza-1H-benzotriazol-1-yl)-1,1,3,3-tetramethyluronium hexafluorophosphate (HATU) (123 mg, 324 μmol) was added and the mixture was stirred at room temperature for 30 min. 2-(4-Chlorophenyl)-3-(2,5-diazabicyclo[2.2.2]oct-2-ylmethyl)imidazo[1,2-a]pyrimidine dihydrochloride (Enantiomer 1; 100 mg) and N,N-diisopropylethylamine (190 μl, 1.1 mmol) were then added and the mixture was stirred at room temperature overnight. Thereafter, the reaction mixture was separated directly into its components via preparative HPLC (Method 8). 25 mg (0.05 mmol, 23% of theory) of the title compound were obtained.

LC-MS (Method 2): $R_t$=1.55 min; MS (ESIpos): m/z=503/505 [M+H]$^+$.

$^1$H-NMR (400 MHz, DMSO-d$_6$): δ [ppm]=1.49-1.97 (m, 4H), 2.02-2.12 (m, 3H), 2.58-2.84 (m, 2.25H), 2.91-3.02 (m, 1H), 3.23 (br. s, 0.75H), 3.34-3.45 (m, 1H), 3.65-3.83 (m, 3.75H), 4.19-4.42 (m, 2.25H), 6.71-6.81 (m, 1H), 7.06-7.17 (m, 1H), 7.49-7.65 (m, 3H), 7.82-7.94 (m, 2H), 8.56-8.63 (m, 1H), 8.97-9.08 (m, 1H).

Example 26

(3-Chloro-6-methoxypyridin-2-yl)(5-{[2-(4-isopropylphenyl)imidazo[1,2-a]pyrimidin-3-yl]methyl}-2,5-diazabicyclo[2.2.2]oct-2-yl)methanone (Enantiomer 2)

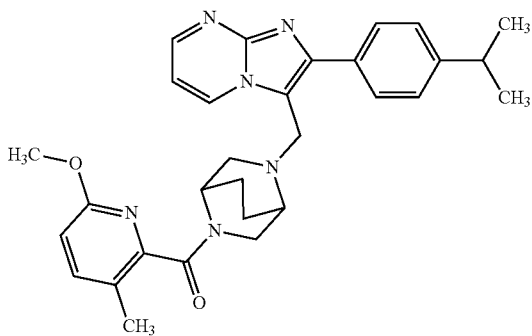 [SMILES: COc1ccc(C)c(C(=O)N2CC3CCC2CN3Cc2c(-c3ccc(C(C)C)cc3)nc3ncccn23)n1]

3-Chloro-6-methoxypyridine-2-carboxylic acid (43 mg, 0.21 mmol) was dissolved in 1.5 ml of DMF, 2-(7-aza-1H-benzotriazol-1-yl)-1,1,3,3-tetramethyluronium hexafluorophosphate (HATU) (121 mg, 0.32 mmol) was added and the mixture was stirred at room temperature for 30 min. 3-(2,5-Diazabicyclo[2.2.2]oct-2-ylmethyl)-2-(4-isopropylphenyl)imidazo[1,2-a]pyrimidine dihydrochloride (Enantiomer 2; 100 mg) and N,N-diisopropylethylamine (190 µl, 1.1 mmol) were then added and the mixture was stirred at room temperature overnight. Thereafter, the reaction mixture was separated directly into its components via preparative HPLC (Method 8). This gave 82 mg (0.15 mmol, content 96%, 70% of theory) of the title compound.

LC-MS (Method 2): $R_t$=1.73 min; m/z=531/533 (M+H)$^+$.
$^1$H-NMR (400 MHz, DMSO-d$_6$): δ [ppm]=1.20-1.31 (m, 6H), 1.53-2.01 (m, 4H), 2.62 (br. d, 0.75H), 2.69-2.85 (m, 1.5H), 2.89-3.03 (m, 2H), 3.21 (br. s, 0.75H), 3.43 (br. d, 1H), 3.70-3.85 (m, 3.75H), 4.21-4.35 (m, 2H), 4.39 (br. s, 0.25H), 6.85-6.96 (m, 1H), 7.05-7.14 (m, 1H), 7.30-7.43 (m, 2H), 7.70-7.87 (m, 2.75H), 7.90 (d, 0.25H), 8.56 (dd, 1H), 8.95-9.04 (m, 1H).

Example 27

(5-Cyclopropyl-1,3-oxazol-4-yl)(5-{[2-(4-isopropylphenyl)imidazo[1,2-a]pyrimidin-3-yl]methyl}-2,5-diazabicyclo[2.2.2]oct-2-yl)methanone (Enantiomer 2)

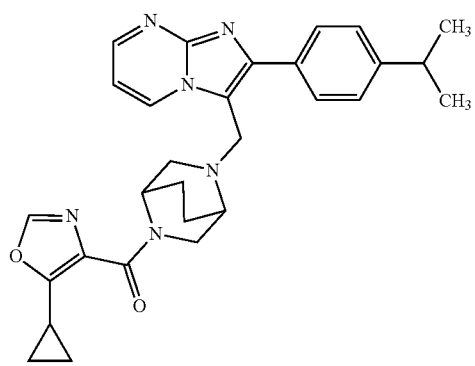 [SMILES: CC(C)c1ccc(-c2nc3ncccn3c2CN2CC3CCC2CN3C(=O)c2ncoc2C2CC2)cc1]

5-Cyclopropyl-1,3-oxazole-4-carboxylic acid (32 mg, 0.21 mmol) was dissolved in 1.35 ml of DMF, 2-(7-aza-1H-benzotriazol-1-yl)-1,1,3,3-tetramethyluronium hexafluorophosphate (HATU) (109 mg, 0.29 mmol) was added and the mixture was stirred at room temperature for 30 min. 3-(2,5-Diazabicyclo[2.2.2]oct-2-ylmethyl)-2-(4-isopropylphenyl)imidazo[1,2-a]pyrimidine dihydrochloride (Enantiomer 2; 90 mg) and N,N-diisopropylethylamine (170 µl, 0.96 mmol) were then added and the mixture was stirred at room temperature overnight. Thereafter, the reaction mixture was separated directly into its components via preparative HPLC (Method 8). 67 mg (0.14 mmol, 71% of theory) of the title compound were obtained.

LC-MS (Method 2): $R_t$=1.51 min; m/z=497 (M+H)$^+$.
$^1$H-NMR (400 MHz, DMSO-d$_6$): δ [ppm]=0.83-0.95 (m, 2H), 0.96-1.08 (m, 2H), 1.25 (d, 6H), 1.51-1.61 (m, 1H), 1.67-1.99 (m, 3H), 2.44-2.57 (m, 0.7H, partially obscured by DMSO signal), 2.57-2.66 (m, 0.3H), 2.73-3.01 (m, 4H), 3.37 (dd, 0.7H), 3.64-3.76 (m, 1H), 4.03 (br. d, 0.3H), 4.23-4.33 (m, 2H), 4.37 (br. s, 0.3H), 4.59 (br. s, 0.7H), 7.06-7.14 (m, 1H), 7.31-7.40 (m, 2H), 7.75-7.83 (m, 2H), 8.12-8.20 (m, 1H), 8.53-8.59 (m, 1H), 8.98-9.06 (m, 1H).

Example 28

(3-Fluoro-6-methoxypyridin-2-yl)(3-{[2-(4-isopropylphenyl)imidazo[1,2-a]pyrimidin-3-yl]methyl}-3,8-diazabicyclo[3.2.1]oct-8-yl)methanone

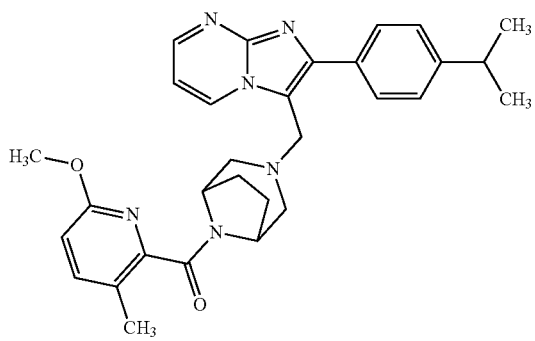 [SMILES: COc1ccc(C)c(C(=O)N2C3CCC2CN(Cc2c(-c4ccc(C(C)C)cc4)nc4ncccn24)C3)n1]

3-Fluoro-6-methoxypyridine-2-carboxylic acid (39.2 mg, 0.21 mmol) was dissolved in 1.5 ml of DMF, 2-(7-aza-1H-benzotriazol-1-yl)-1,1,3,3-tetramethyluronium hexafluorophosphate (HATU) (119 mg, 0.31 mmol) was added and the mixture was stirred at room temperature for 30 min. 3-(3,8-Diazabicyclo[3.2.1]oct-3-ylmethyl)-2-(4-isopropylphenyl)imidazo[1,2-a]pyrimidine dihydrochloride (98 mg) and N,N-diisopropylethylamine (180 µl, 1.04 mmol) were then added and the mixture was stirred at room temperature overnight. Thereafter, the reaction mixture was separated directly into its components via preparative HPLC (Method 8). 65 mg (0.13 mmol, 61% of theory) of the title compound were obtained.

LC-MS (Method 5): $R_t$=1.22 min; MS (ESIpos): m/z=515 [M+H]$^+$.
$^1$H-NMR (400 MHz, DMSO-d$_6$): δ [ppm]=1.26 (d, 6H), 1.63-1.86 (m, 4H), 2.44 (br. t, 2H), 2.48-2.60 (m, 1H, partially obscured by DMSO signal), 2.76 (dd, 1H), 2.96 (quin, 1H), 3.76 (s, 3H), 3.92 (br. s, 1H), 4.00-4.11 (m, 2H), 4.61 (br. s, 1H), 6.95 (dd, 1H), 7.12 (dd, 1H), 7.36 (d, 2H), 7.77 (t, 1H), 7.83 (d, 2H), 8.57 (dd, 1H), 9.02 (dd, 1H).

Example 29

(3-Chloro-6-methoxypyridin-2-yl)(3-{[2-(4-isopropylphenyl)imidazo[1,2-a]pyrimidin-3-yl]methyl}-3,8-diazabicyclo[3.2.1]oct-8-yl)methanone

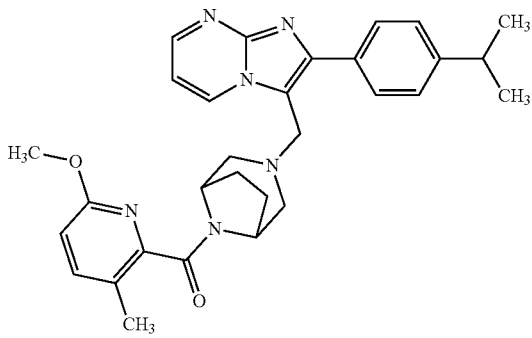 [SMILES: COc1ccc(C)c(C(=O)N2C3CCC2CN(Cc2c(-c4ccc(C(C)C)cc4)nc4ncccn24)C3)n1]

3-Chloro-6-methoxypyridine-2-carboxylic acid (43 mg, 0.23 mmol) was dissolved in 1.5 ml of DMF, 2-(7-aza-1H-benzotriazol-1-yl)-1,1,3,3-tetramethyluronium hexafluorophosphate (HATU) (118 mg, 0.31 mmol) was added and the mixture was stirred at room temperature for 30 min. 3-(3,8-Diazabicyclo[3.2.1]oct-3-ylmethyl)-2-(4-isopropylphenyl)imidazo[1,2-a]pyrimidine dihydrochloride (98 mg) and N,N-diisopropylethylamine (180 µl, 1.04 mmol) were then added and the mixture was stirred at room temperature overnight. Thereafter, the reaction mixture was separated directly into its components via preparative HPLC (Method 8). 67 mg (0.13 mmol, 60% of theory) of the title compound were obtained.

LC-MS (Method 5): $R_t$=1.27 min; MS (ESIpos): m/z=531/533 $[M+H]^+$.

$^1$H-NMR (400 MHz, DMSO-$d_6$): δ [ppm]=1.26 (d, 6H), 1.63-1.84 (m, 4H), 2.41 (br. t, 2H), 2.46-2.57 (m, 1H, obscured by DMSO signal), 2.75 (br. d, 1H), 2.96 (quin, 1H), 3.63 (br. s, 1H), 3.79 (s, 3H), 4.00-4.11 (m, 2H), 4.60 (br. s, 1H), 6.92 (d, 1H), 7.12 (dd, 1H), 7.37 (d, 2H), 7.82 (d, 2H), 7.87 (d, 1H), 8.56 (dd, 1H), 9.01 (dd, 1H).

Analogously to Examples 13-29, the following compounds were prepared from the starting materials specified in each case:

| Example | Name/Structure/Starting materials | Analytical data |
|---|---|---|
| 30 | (7-{[2-(4-chlorophenyl)imidazo[1,2-a]pyrimidin-3-yl]methyl}-3-oxa-7,9-diazabicyclo[3.3.1]non-9-yl)(2-fluorophenyl)methanone<br><br>from 7-{[2-(4-chlorophenyl)imidazo[1,2-a]pyrimidin-3-yl]methyl}-3-oxa-7,9-diazabicyclo[3.3.1]nonane dihydrochloride and 2-fluorobenzoic acid | $^1$H-NMR (400 MHz, DMSO-$d_6$): δ [ppm] = 2.43 (br. d, 1H), 2.47-2.59 (m, 1H, partially obscured by DMSO signal), 2.87 (br. d, 1H), 3.02 (br. d, 1H), 3.37 (br. s, 1H), 3.59 (br. d, 1H), 3.65-3.76 (m, 2H), 3.87 (d, 1H), 3.97 (s, 2H), 4.47 (br. s, 1H), 7.08 (dd, 1H), 7.24-7.34 (m, 2H), 7.41-7.53 (m, 2H), 7.55 (d, 2H), 7.95 (d, 2H), 8.58 (dd, 1H), 9.27 (dd, 1H).<br>LC-MS (Method 2):<br>$R_t$ = 1.53 min; m/z = 492/494 $(M + H)^+$. |

-continued

| Example | Name/Structure/Starting materials | Analytical data |
|---|---|---|
| 31 | (7-{[2-(4-chlorophenyl)imidazo[1,2-a]pyrimidin-3-yl]methyl}-3-oxa-7,9-diazabicyclo[3.3.1]non-9-yl)(3-methoxyphenyl)methanone<br>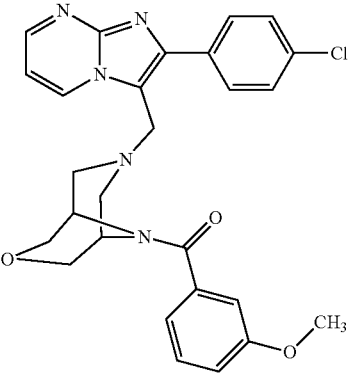<br>from 7-{[2-(4-chlorophenyl)imidazo[1,2-a]pyrimidin-3-yl]methyl}-3-oxa-7,9-diazabicyclo[3.3.1]nonane dihydrochloride and 3-methoxybenzoic acid | $^1$H-NMR (400 MHz, DMSO-d$_6$): δ [ppm] = 2.46-2.55 (m, 1H, obscured by DMSO signal), 2.59 (br. d, 1H), 2.86 (br. d, 1H), 2.99 (br. d, 1H), 3.54-3.75 (m, 4H), 3.77 (s, 3H), 3.85 (d, 1H), 3.98 (s, 2H), 4.39 (br. s, 1H), 6.91-7.12 (m, 4H), 7.36 (t, 1H), 7.55 (d, 2H), 7.97 (d, 2H), 8.57 (dd, 1H), 9.29 (dd, 1H).<br>LC-MS (Method 2):<br>R$_t$ = 1.53 min; m/z = 504/506 (M + H)$^+$. |
| 32 | (3-{[2-(4-chlorophenyl)imidazo[1,2-a]pyrimidin-3-yl]methyl}-3,8-diazabicyclo[3.2.1]oct-8-yl)(2-fluorophenyl)methanone<br>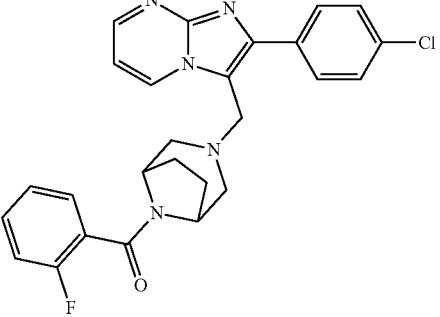<br>from 2-(4-chlorophenyl)-3-(3,8-diazabicyclo[3.2.1]oct-3-ylmethyl)imidazo[1,2-a]pyrimidine dihydrochloride and 2-fluorobenzoic acid | $^1$H-NMR (400 MHz, DMSO-d$_6$): δ [ppm] = 1.60-1.79 (m, 4H), 2.25 (br. d, 1H), 2.42 (br. d, 1H), 2.47-2.60 (m, 1H, partially obscured by DMSO signal), 2.68 (br. d, 1H), 3.66 (br. s, 1H), 4.04 (s, 2H), 4.59 (br. s, 1H), 7.14 (dd, 1H), 7.24-7.32 (m, 2H), 7.40-7.53 (m, 2H), 7.57 (d, 2H), 7.95 (d, 2H), 8.59 (dd, 1H), 9.04 (dd, 1H).<br>LC-MS (Method 2):<br>R$_t$ = 1.73 min; m/z = 476/478 (M + H)$^+$. |
| 33 | (3-{[2-(4-chlorophenyl)imidazo[1,2-a]pyrimidin-3-yl]methyl}-3,8-diazabicyclo[3.2.1]oct-8-yl)[6-(methylsulfanyl)pyridin-2-yl]methanone<br>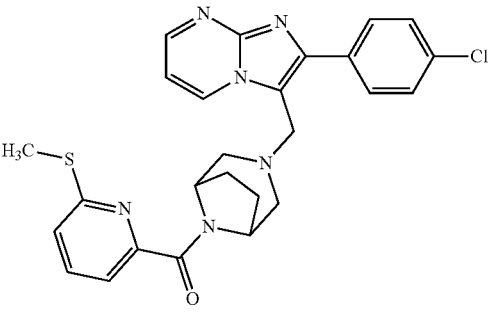<br>from 2-(4-chlorophenyl)-3-(3,8-diazabicyclo[3.2.1]oct-3-ylmethyl)imidazo[1,2-a]pyrimidine dihydrochloride and 6-(methylsulfanyl)pyridine-2-carboxylic acid | $^1$H-NMR (400 MHz, DMSO-d$_6$): δ [ppm] = 1.64-1.83 (m, 4H), 2.40-2.63 (m, 3H, partially obscured by DMSO signal), 2.43 (s, 3H), 2.74 (br. d, 1H), 3.99-4.11 (m, 2H), 4.63 (br. s, 2H), 7.15 (dd, 1H), 7.42 (dd, 2H), 7.57 (d, 2H), 7.75 (t, 1H), 7.97 (d, 2H), 8.55-8.62 (m, 1H), 9.06 (d, 1H).<br>LC-MS (Method 2):<br>R$_t$ = 1.86 min; m/z = 505/507 (M + H)$^+$. |

| Example | Name/Structure/Starting materials | Analytical data |
|---|---|---|
| 34 | (3-{[2-(4-chlorophenyl)imidazo[1,2-a]pyrimidin-3-yl]methyl}-3,8-diazabicyclo[3.2.1]oct-8-yl)(cyclopentyl)methanone<br>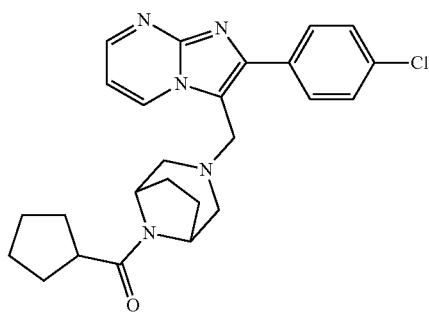<br>from 2-(4-chlorophenyl)-3-(3,8-diazabicyclo[3.2.1]oct-3-ylmethyl)imidazo[1,2-a]pyrimidine dihydrochloride and cyclopentanecarboxylic acid | $^1$H-NMR (400 MHz, DMSO-$d_6$): δ [ppm] = 1.44-1.66 (m, 7H), 1.66-1.80 (m, 5H), 2.26 (br. d, 2H), 2.47-2.66 (m, 2H, partially obscured by DMSO signal), 2.80-2.92 (m, 1H), 3.94-4.06 (m, 2H), 4.28 (br. s, 1H), 4.41 (br. d, 1H), 7.14 (dd, 1H), 7.56 (d, 2H), 7.96 (d, 2H), 8.59 (dd, 1H), 9.05 (dd, 1H).<br>LC-MS (Method 2):<br>$R_t$ = 1.83 min; m/z = 450/452 (M + H)$^+$. |
| 35 | (3-{[2-(4-chlorophenyl)imidazo[1,2-a]pyrimidin-3-yl]methyl}-3,8-diazabicyclo[3.2.1]oct-8-yl)[6-(methylamino)pyridin-2-yl]methanone<br>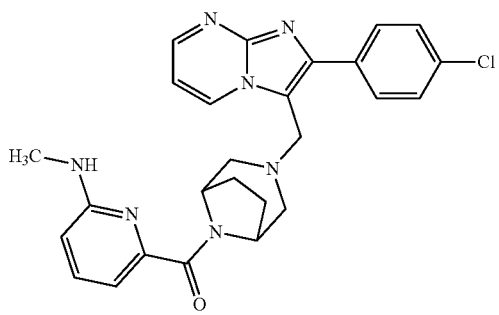<br>from 2-(4-chlorophenyl)-3-(3,8-diazabicyclo[3.2.1]oct-3-ylmethyl)imidazo[1,2-a]pyrimidine dihydrochloride and 6-(methylamino)pyridine-2-carboxylic acid | $^1$H-NMR (400 MHz, DMSO-$d_6$): δ [ppm] = 1.63-1.81 (m, 4H), 2.42 (br. d, 1H), 2.47-2.62 (m, 2H, partially obscured by DMSO signal), 2.64-2.75 (m, 1H), 2.67 (d, 3H), 3.97-4.09 (m, 2H), 4.60 (br. s, 1H), 4.76 (br. s, 1H), 6.51 (d, 1H), 6.65 (q, 1H), 6.82 (d, 1H), 7.14 (dd, 1H), 7.44 (t, 1H), 7.56 (d, 2H), 7.96 (d, 2H), 8.59 (dd, 1H), 9.05 (dd, 1H).<br>LC-MS (Method 2):<br>$R_t$ = 1.51 min; m/z = 532/534 (M − H + HCOOH)—. |
| 36 | (3-{[2-(4-chlorophenyl)imidazo[1,2-a]pyrimidin-3-yl]methyl}-3,8-diazabicyclo[3.2.1]oct-8-yl)(3-methoxyphenyl)methanone<br>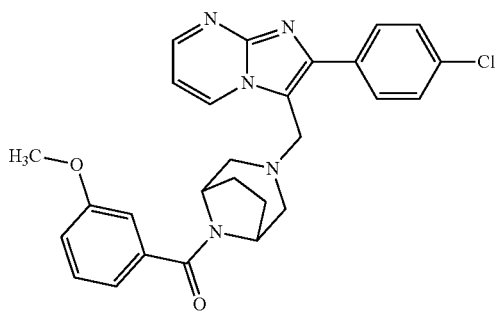<br>from 2-(4-chlorophenyl)-3-(3,8-diazabicyclo[3.2.1]oct-3-ylmethyl)imidazo[1,2-a]pyrimidine dihydrochloride and 3-methoxybenzoic acid | $^1$H-NMR (400 MHz, DMSO-$d_6$): δ [ppm] = 1.64-1.80 (m, 4H), 2.30-2.47 (m, 2H), 2.57-2.74 (m, 2H), 3.78 (s, 3H), 3.92 (br. s, 1H), 4.05 (s, 2H), 4.54 (br. s, 1H), 6.92-7.08 (m, 3H), 7.30 (br. t, 1H), 7.35 (t, 1H), 7.61 (d, 2H), 7.93 (d, 2H), 8.71 (br. d, 1H), 9.15 (br. d, 1H).<br>LC-MS (Method 2):<br>$R_t$ = 1.73 min; m/z = 488/490 (M + H)$^+$. |

| Example | Name/Structure/Starting materials | Analytical data |
|---|---|---|
| 37 | (5-{[2-(4-chlorophenyl)imidazo[1,2-a]pyrimidin-3-yl]methyl}-2,5-diazabicyclo[2.2.2]oct-2-yl)(cyclopentyl)methanone (Enantiomer 1)<br>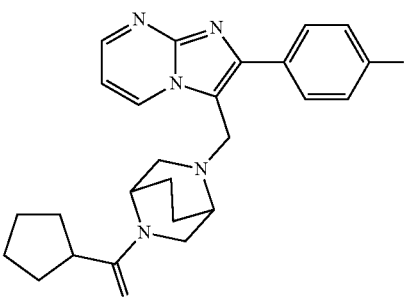<br>from 2-(4-chlorophenyl)-3-(2,5-diazabicyclo[2.2.2]oct-2-ylmethyl)imidazo[1,2-a]pyrimidine dihydrochloride (Enantiomer 1) and cyclopentanecarboxylic acid | $^1$H-NMR (400 MHz, DMSO-d$_6$): δ [ppm] = 1.38-1.79 (m, 11H), 1.82-1.96 (m, 1H), 2.63-2.86 (m, 4H), 3.19 (dd, 0.5H), 3.37 (dd, 0.5H), 3.54 (br. d, 0.5H), 3.75 (br. d, 0.5H), 3.93 (br. d, 0.5H), 4.18-4.31 (m, 2.5H), 7.12 (dd, 1H), 7.56 (d, 2H), 7.89 (d, 2H), 8.59 (dd, 1H), 9.03 (dt, 1H).<br>LC-MS (Method 2):<br>R$_t$ = 1.42 min; m/z = 450/452 (M + H)$^+$. |
| 38 | (5-{[2-(4-chlorophenyl)imidazo[1,2-a]pyrimidin-3-yl]methyl}-2,5-diazabicyclo[2.2.2]oct-2-yl)(3-methoxyphenyl)methanone (Enantiomer 1)<br>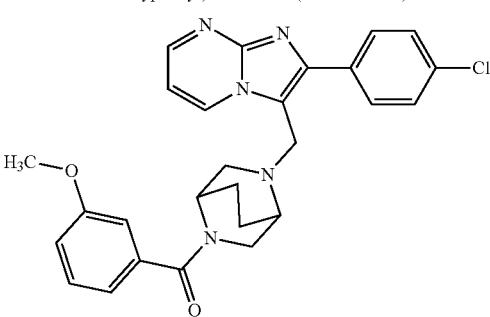<br>from 2-(4-chlorophenyl)-3-(2,5-diazabicyclo[2.2.2]oct-2-ylmethyl)imidazo[1,2-a]pyrimidine dihydrochloride (Enantiomer 1) and 3-methoxybenzoic acid | $^1$H-NMR (400 MHz, DMSO-d$_6$): δ [ppm] = 1.44-1.99 (m, 4H), 2.61-2.72 (m, 1H), 2.76-2.84 (m, 1H), 2.90 (br. s, 1H), 3.17 (br. d, 0.25H), 3.37 (br. d, 0.75H), 3.53 (br. s, 0.75H), 3.63 (br. d, 0.25H), 3.69-3.82 (m, 3.75H), 4.21-4.34 (m, 2.25H), 6.80-6.88 (m, 1.5H), 6.94-7.06 (m, 1.5H), 7.08-7.17 (m, 1H), 7.26-7.39 (m, 1H), 7.50-7.61 (m, 2H), 7.86-7.96 (m, 2H), 8.55-8.63 (m, 1H), 9.00-9.09 (m, 1H).<br>LC-MS (Method 2):<br>R$_t$ = 1.46 min; m/z = 488/490 (M + H)$^+$. |
| 39 | (5-{[2-(4-chlorophenyl)imidazo[1,2-a]pyrimidin-3-yl]methyl}-2,5-diazabicyclo[2.2.2]oct-2-yl)(2-fluorophenyl)methanone (Enantiomer 1)<br>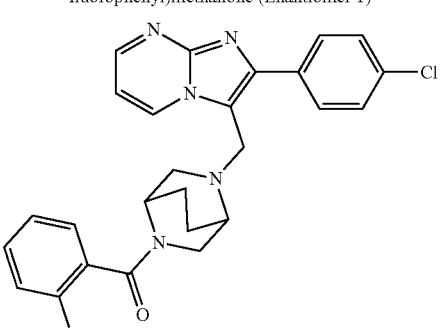<br>from 2-(4-chlorophenyl)-3-(2,5-diazabicyclo[2.2.2]oct-2-ylmethyl)imidazo[1,2-a]pyrimidine dihydrochloride (Enantiomer 1) and 2-fluorobenzoic acid | $^1$H-NMR (400 MHz, DMSO-d$_6$): δ [ppm] = 1.47-1.82 (m, 3H), 1.84-1.98 (m, 1H), 2.46-2.57 (m, 0.75H, obscured by DMSO signal), 2.60-2.87 (m, 2.25H), 2.92 (br. s, 0.75H), 3.02 (br. d, 0.25H), 3.42 (br. d, 1H), 3.77 (br. d, 0.75H), 4.20-4.33 (m, 2H), 4.37 (br. s, 0.25H), 7.09-7.17 (m, 1H), 7.20-7.40 (m, 3H), 7.41-7.61 (m, 3H), 7.83-7.95 (m, 2H), 8.56-8.63 (m, 1H), 8.98-9.08 (m, 1H).<br>LC-MS (Method 2):<br>R$_t$ = 1.49 min; m/z = 476/478 (M + H)$^+$. |

| Example | Name/Structure/Starting materials | Analytical data |
|---|---|---|
| 40 | (5-{[2-(4-chlorophenyl)imidazo[1,2-a]pyrimidin-3-yl]methyl}-2,5-diazabicyclo[2.2.2]oct-2-yl)(6-methoxypyridin-2-yl)methanone (Enantiomer 1)<br><br>from 2-(4-chlorophenyl)-3-(2,5-diazabicyclo[2.2.2]oct-2-ylmethyl)imidazo[1,2-a]pyrimidine dihydrochloride (Enantiomer 1) and 6-methoxypyridine-2-carboxylic acid | $^1$H-NMR (400 MHz, DMSO-d$_6$): δ [ppm] = 1.46-1.99 (m, 4H), 2.63-2.73 (m, 1H), 2.80-2.94 (m, 2H), 3.39 (dd, 0.75H), 3.48 (br. d, 0.25H), 3.70-3.83 (m, 3.75H), 3.92 (br. d, 0.25H), 3.98 (br. s, 0.75H), 4.24-4.35 (m, 2H), 4.38 (br. s, 0.25H), 6.84-6.94 (m, 1H), 7.08-7.20 (m, 1.75H), 7.29 (d, 0.25H), 7.49-7.60 (m, 2H), 7.74-7.94 (m, 3H), 8.55-8.62 (m, 1H), 9.00-9.08 (m, 1H).<br>LC-MS (Method 2):<br>R$_t$ = 1.41 min; m/z = 489/491 (M + H)$^+$. |
| 41 | (5-{[2-(4-chlorophenyl)imidazo[1,2-a]pyrimidin-3-yl]methyl}-2,5-diazabicyclo[2.2.2]oct-2-yl)(3-fluoro-6-methoxypyridin-2-yl)methanone (Enantiomer 1)<br><br>from 2-(4-chlorophenyl)-3-(2,5-diazabicyclo[2.2.2]oct-2-ylmethyl)imidazo[1,2-a]pyrimidine dihydrochloride (Enantiomer 1) and 3-fluoro-6-methoxypyridine-2-carboxylic acid | $^1$H-NMR (400 MHz, DMSO-d$_6$): δ [ppm] = 1.49-2.01 (m, 4H), 2.62-2.87 (m, 2.25H), 2.92 (br. s, 0.75H), 3.15 (br. d, 0.25H), 3.38-3.50 (m, 1.5H), 3.56 (br. d, 0.25H), 3.69-3.84 (m, 3.75H), 4.20-4.35 (m, 2H), 4.38 (br. s, 0.25H), 6.87-6.99 (m, 1H), 7.08-7.17 (m, 1H), 7.49-7.59 (m, 2H), 7.70-7.82 (m, 1H), 7.83-7.95 (m, 2H), 8.56-8.63 (m, 1H), 8.98-9.08 (m, 1H).<br>LC-MS (Method 2):<br>R$_t$ = 1.51 min; m/z = 507/509 (M + H)$^+$. |
| 42 | (5-{[2-(4-chlorophenyl)imidazo[1,2-a]pyrimidin-3-yl]methyl}-2,5-diazabicyclo[2.2.2]oct-2-yl)(2-fluorophenyl)methanone (Enantiomer 2)<br><br>from 2-(4-chlorophenyl)-3-(2,5-diazabicyclo[2.2.2]oct-2-ylmethyl)imidazo[1,2-a]pyrimidine dihydrochloride (Enantiomer 2) and 2-fluorobenzoic acid | $^1$H-NMR (400 MHz, DMSO-d$_6$): δ [ppm] = 1.48-1.83 (m, 3H), 1.83-1.98 (m, 1H), 2.46-2.57 (m, 0.75H, obscured by DMSO signal), 2.60-2.88 (m, 2.25H), 2.92 (br. s, 0.75H), 3.02 (br. d, 0.25H), 3.43 (br. d, 1H), 3.77 (br. d, 0.75H), 4.20-4.34 (m, 2H), 4.38 (br. s, 0.25H), 7.08-7.17 (m, 1H), 7.19-7.40 (m, 3H), 7.41-7.60 (m, 3H), 7.83-7.95 (m, 2H), 8.55-8.63 (m, 1H), 8.97-9.08 (m, 1H).<br>LC-MS (Method 2):<br>R$_t$ = 1.50 min; m/z = 476/478 (M + H)$^+$. |

| Example | Name/Structure/Starting materials | Analytical data |
|---|---|---|
| 43 | (5-{[2-(4-chlorophenyl)imidazo[1,2-a]pyrimidin-3-yl]methyl}-2,5-diazabicyclo[2.2.2]oct-2-yl)(3-methoxyphenyl)methanone (Enantiomer 2)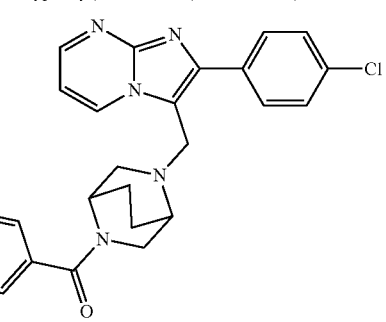from 2-(4-chlorophenyl)-3-(2,5-diazabicyclo[2.2.2]oct-2-ylmethyl)imidazo[1,2-a]pyrimidine dihydrochloride (Enantiomer 2) and 3-methoxybenzoic acid | $^1$H-NMR (400 MHz, DMSO-$d_6$): δ [ppm] = 1.44-1.99 (m, 4H), 2.61-2.72 (m, 1H), 2.74-2.84 (m, 1H), 2.90 (br. s, 1H), 3.17 (br. d, 0.25H), 3.37 (br. d, 0.75H), 3.53 (br. s, 0.75H), 3.63 (br. d, 0.25H), 3.67-3.82 (m, 3.75H), 4.18-4.35 (m, 2.25H), 6.76-6.87 (m, 1.5H), 6.92-7.05 (m, 1.5H), 7.08-7.17 (m, 1H), 7.25-7.39 (m, 1H), 7.49-7.61 (m, 2H), 7.84-7.96 (m, 2H), 8.52-8.63 (m, 1H), 8.98-9.09 (m, 1H). LC-MS (Method 2): $R_t$ = 1.46 min; m/z = 488/490 (M + H)$^+$. |
| 44 | (5-{[2-(4-chlorophenyl)imidazo[1,2-a]pyrimidin-3-yl]methyl}-2,5-diazabicyclo[2.2.2]oct-2-yl)(6-methoxypyridin-2-yl)methanone (Enantiomer 2)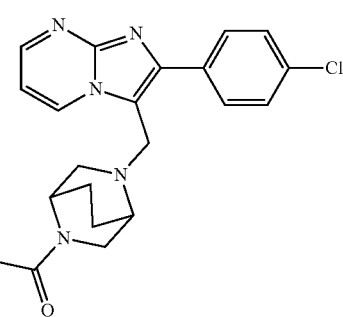from 2-(4-chlorophenyl)-3-(2,5-diazabicyclo[2.2.2]oct-2-ylmethyl)imidazo[1,2-a]pyrimidine dihydrochloride (Enantiomer 2) and 6-methoxypyridine-2-carboxylic acid | $^1$H-NMR (400 MHz, DMSO-$d_6$): δ [ppm] = 1.46-1.99 (m, 4H), 2.63-2.74 (m, 1H), 2.80-2.94 (m, 2H), 3.39 (dd, 0.75H), 3.49 (br. d, 0.25H), 3.69-3.83 (m, 3.75H), 3.92 (br. d, 0.25H), 3.98 (br. s, 0.75H), 4.24-4.35 (m, 2H), 4.38 (br. s, 0.25H), 6.84-6.94 (m, 1H), 7.08-7.20 (m, 1.75H), 7.29 (d, 0.25H), 7.48-7.60 (m, 2H), 7.73-7.95 (m, 3H), 8.54-8.63 (m, 1H), 9.00-9.09 (m, 1H). LC-MS (Method 2): $R_t$ = 1.41 min; m/z = 489/491 (M + H)$^+$. |
| 45 | (3-chloro-6-methoxypyridin-2-yl)(5-{[2-(4-chlorophenyl)imidazo[1,2-a]pyrimidin-3-yl]methyl}-2,5-diazabicyclo[2.2.2]oct-2-yl)methanone (Enantiomer 2)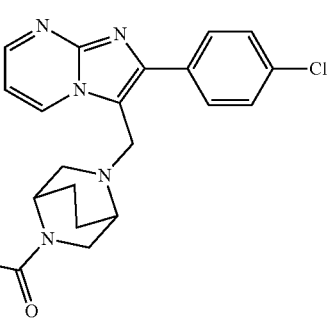from 2-(4-chlorophenyl)-3-(2,5-diazabicyclo[2.2.2]oct-2-ylmethyl)imidazo[1,2-a]pyrimidine dihydrochloride (Enantiomer 2) and 3-chloro-6-methoxypyridine-2-carboxylic acid | $^1$H-NMR (400 MHz, DMSO-$d_6$): δ [ppm] = 1.52-2.00 (m, 4H), 2.72 (br. d, 0.75H), 2.73 (br. d, 1H), 2.80 (br. s, 0.5H), 2.94-3.01 (m, 1H), 3.20 (br. s, 0.75H), 3.35-3.47 (m, 1H), 3.70-3.86 (m, 3.75H), 4.20-4.33 (m, 2H), 4.38 (br. s, 0.25H), 6.85-6.97 (m, 1H), 7.08-7.19 (m, 1H), 7.49-7.61 (m, 2H), 7.79-7.94 (m, 3H), 8.56-8.64 (m, 1H), 8.97-9.08 (m, 1H). LC-MS (Method 2): $R_t$ = 1.63 min; MS (ESIpos): m/z = 523/524/525 [M + H]$^+$. |

| Example | Name/Structure/Starting materials | Analytical data |
|---|---|---|
| 46 | (7-{[2-(4-chlorophenyl)imidazo[1,2-a]pyrimidin-3-yl]methyl}-3-oxa-7,9-diazabicyclo[3.3.1]non-9-yl)(5-cyclopropyl-1,3-oxazol-4-yl)methanone<br>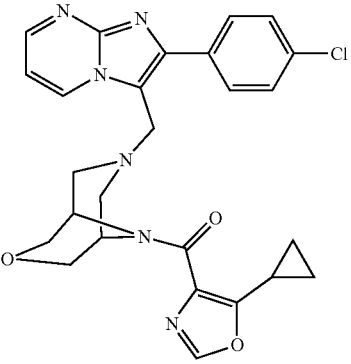<br>from 7-{[2-(4-chlorophenyl)imidazo[1,2-a]pyrimidin-3-yl]methyl}-3-oxa-7,9-diazabicyclo[3.3.1]nonane dihydrochloride and 5-cyclopropyl-1,3-oxazole-4-carboxylic acid | $^1$H-NMR (400 MHz, DMSO-$d_6$): δ [ppm] = 0.88-0.97 (m, 2H), 1.03-1.13 (m, 2H), 2.44-2.65 (m, 3H, partially obscured by DMSO signal), 2.92-3.06 (m, 2H), 3.62-3.73 (m, 2H), 3.77-3.90 (m, 2H), 3.96 (s, 2H), 4.41 (br. s, 1H), 4.75 (br. s, 1H), 7.08 (dd, 1H), 7.54 (d, 2H), 7.98 (d, 2H), 8.20 (s, 1H), 8.59 (dd, 1H), 9.29 (dd, 1H).<br>LC-MS (Method 1):<br>$R_t$ = 0.76 min; MS (ESIpos): m/z = 505/507 [M + H]$^+$. |
| 47 | (3-{[2-(4-chlorophenyl)imidazo[1,2-a]pyrimidin-3-yl]methyl}-3,8-diazabicyclo[3.2.1]oct-8-yl)(2-cyclopropyl-1,3-oxazol-4-yl)methanone<br>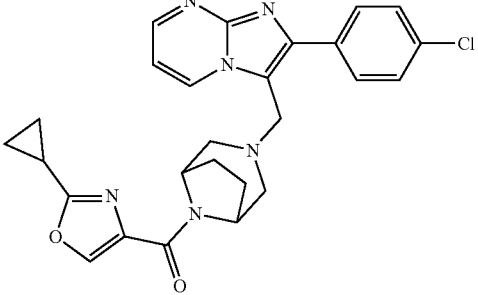<br>from 2-(4-chlorophenyl)-3-(3,8-diazabicyclo[3.2.1]oct-3-ylmethyl)imidazo[1,2-a]pyrimidine dihydrochloride and 2-cyclopropyl-1,3-oxazole-4-carboxylic acid | $^1$H-NMR (400 MHz, DMSO-$d_6$): δ [ppm] = 0.89-0.98 (m, 2H), 1.00-1.09 (m, 2H), 1.57-1.87 (m, 4H), 2.08-2.18 (m, 1H), 2.30-2.42 (m, 2H), 2.58-2.70 (m, 2H), 4.02 (s, 2H), 4.53 (br. s, 1H), 5.15 (br. s, 1H), 7.15 (dd, 1H), 7.56 (d, 2H), 7.97 (d, 2H), 8.37 (s, 1H), 8.59 (dd, 1H), 9.05 (dd, 1H).<br>LC-MS (Method 2):<br>$R_t$ = 1.75 min; MS (ESIpos): m/z = 489/491 [M + H]$^+$. |
| 48 | (3-{[2-(4-chlorophenyl)imidazo[1,2-a]pyrimidin-3-yl]methyl}-3,8-diazabicyclo[3.2.1]oct-8-yl)(5-methyl-1,3-oxazol-4-yl)methanone<br>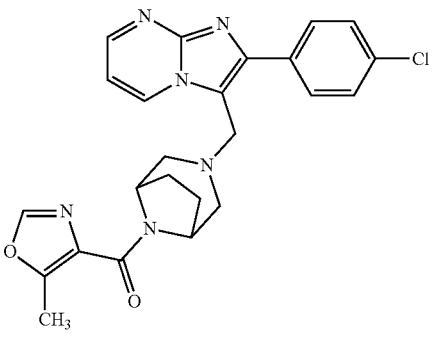<br>from 2-(4-chlorophenyl)-3-(3,8-diazabicyclo[3.2.1]oct-3-ylmethyl)imidazo[1,2-a]pyrimidine dihydrochloride and 5-methyl-1,3-oxazole-4-carboxylic acid | $^1$H-NMR (400 MHz, DMSO-$d_6$): δ [ppm] = 1.59-1.84 (m, 4H), 2.35-2.44 (m, 2H), 2.52 (s, 3H, partially obscured by DMSO signal), 2.60-2.69 (m, 2H), 4.02 (s, 2H), 4.57 (br. s, 1H), 5.12 (br. s, 1H), 7.14 (dd, 1H), 7.56 (d, 2H), 7.97 (d, 2H), 8.29 (s, 1H), 8.56 (dd, 1H), 9.06 (dd, 1H).<br>LC-MS (Method 2):<br>$R_t$ = 1.59 min; MS (ESIpos): m/z = 463/465 [M + H]$^+$. |

| Example | Name/Structure/Starting materials | Analytical data |
|---|---|---|
| 49 | (3-{[2-(4-chlorophenyl)imidazo[1,2-a]pyrimidin-3-yl]methyl}-3,8-diazabicyclo[3.2.1]oct-8-yl)(5-isopropyl-1,3-oxazol-4-yl)methanone<br><br>from 2-(4-chlorophenyl)-3-(3,8-diazabicyclo[3.2.1]oct-3-ylmethyl)imidazo[1,2-a]pyrimidine dihydrochloride and 5-isopropyl-1,3-oxazole-4-carboxylic acid | $^1$H-NMR (400 MHz, DMSO-$d_6$): δ [ppm] = 1.21 (t, 6H), 1.63-1.82 (m, 4H), 2.39 (br. t, 2H), 2.64 (br. t, 2H), 3.62 (quin, 1H), 4.02 (s, 2H), 4.57 (br. s, 1H), 4.97 (br. s, 1H), 7.15 (dd, 1H), 7.56 (d, 2H), 7.96 (d, 2H), 8.29 (s, 1H), 8.59 (dd, 1H), 9.05 (dd, 1H).<br>LC-MS (Method 2):<br>$R_t$ = 1.86 min; MS (ESIpos): m/z = 491/493 [M + H]$^+$. |
| 50 | (3-{[2-(4-chlorophenyl)imidazo[1,2-a]pyrimidin-3-yl]methyl}-3,8-diazabicyclo[3.2.1]oct-8-yl)(2,4-dimethyl-1,3-oxazol-5-yl)methanone<br><br>from 2-(4-chlorophenyl)-3-(3,8-diazabicyclo[3.2.1]oct-3-ylmethyl)imidazo[1,2-a]pyrimidine dihydrochloride and 2,4-dimethyl-1,3-oxazole-5-carboxylic acid | $^1$H-NMR (400 MHz, DMSO-$d_6$): δ [ppm] = 1.74 (br. s, 4H), 2.27 (s, 3H), 2.34-2.45 (m, 2H), 2.40 (s, 3H), 2.60-2.70 (m, 2H), 4.04 (s, 2H), 4.58 (br. s, 2H), 7.17 (dd, 1H), 7.56 (d, 2H), 7.97 (d, 2H), 8.59 (dd, 1H), 9.07 (dd, 1H).<br>LC-MS (Method 2):<br>$R_t$ = 1.53 min; MS (ESIpos): m/z = 477/479 [M + H]$^+$. |
| 51 | (3-{[2-(4-chlorophenyl)imidazo[1,2-a]pyrimidin-3-yl]methyl}-3,8-diazabicyclo[3.2.1]oct-8-yl)(5-ethyl-1,3-oxazol-4-yl)methanone<br><br>from 2-(4-chlorophenyl)-3-(3,8-diazabicyclo[3.2.1]oct-3-ylmethyl)imidazo[1,2-a]pyrimidine dihydrochloride and 5-ethyl-1,3-oxazole-4-carboxylic acid | $^1$H-NMR (400 MHz, DMSO-$d_6$): δ [ppm] = 1.17 (t, 3H), 1.61-1.83 (m, 4H), 2.39 (br. d, 2H), 2.64 (br. d, 2H), 2.95 (q, 2H), 4.02 (s, 2H), 4.57 (br. s, 1H), 5.07 (br. s, 1H), 7.15 (dd, 1H), 7.56 (d, 2H), 7.96 (d, 2H), 8.30 (s, 1H), 8.59 (dd, 1H), 9.05 (dd, 1H).<br>LC-MS (Method 2):<br>$R_t$ = 1.73 min; MS (ESIpos): m/z = 477/479 [M + H]$^+$. |

| Example | Name/Structure/Starting materials | Analytical data |
|---|---|---|
| 52 | (4-bromo-5-methyl-1,3-thiazol-2-yl)(3-{[2-(4-chlorphenyl)imidazo[1,2-a]pyrimidin-3-yl]methyl}-3,8-diazabicyclo[3.2.1]oct-8-yl)methanone<br />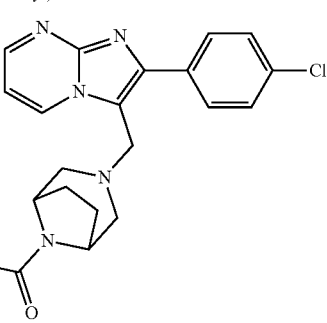<br />from 2-(4-chlorophenyl)-3-(3,8-diazabicyclo[3.2.1]oct-3-ylmethyl)imidazo[1,2-a]pyrimidine dihydrochloride and 4-bromo-5-methyl-1,3-thiazole-2-carboxylic acid | $^1$H-NMR (400 MHz, DMSO-d$_6$): δ [ppm] = 1.67-1.77 (m, 2H), 1.79-1.91 (m, 2H), 2.39-2.48 (m, 2H), 2.43 (s, 3H), 2.66 (br. d, 1H), 2.72 (br. d, 1H), 4.04 (s, 2H), 4.57 (br. s, 1H), 5.46 (br. s, 1H), 7.15 (dd, 1H), 7.56 (d, 2H), 7.97 (d, 2H), 8.59 (dd, 1H), 9.06 (dd, 1H).<br />LC-MS (Method 1):<br />R$_t$ = 1.10 min; MS (ESIpos):<br />m/z = 557/559 [M + H]$^+$. |
| 53 | (3-{[2-(4-chlorophenyl)imidazo[1,2-a]pyrimidin-3-yl]methyl}-3,8-diazabicyclo[3.2.1]oct-8-yl)(5-cyclopropyl-1,3-oxazol-4-yl)methanone<br />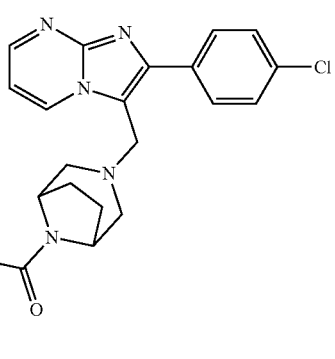<br />from 2-(4-chlorophenyl)-3-(3,8-diazabicyclo[3.2.1]oct-3-ylmethyl)imidazo[1,2-a]pyrimidine dihydrochloride and 5-cyclopropyl-1,3-oxazole-4-carboxylic acid | $^1$H-NMR (400 MHz, DMSO-d$_6$): δ [ppm] = 0.86-0.99 (m, 2H), 1.02-1.13 (m, 2H), 1.61-1.85 (m, 4H), 2.36-2.46 (m, 2H), 2.60-2.75 (m, 3H), 4.03 (s, 2H), 4.58 (br. s, 1H), 5.12 (br. s, 1H), 7.15 (dd, 1H), 7.56 (d, 2H), 7.97 (d, 2H), 8.18 (s, 1H), 8.59 (dd, 1H), 9.06 (dd, 1H).<br />LC-MS (Method 1):<br />R$_t$ = 0.91 min; MS (ESIpos):<br />m/z = 489/491 [M + H]$^+$. |
| 54 | (3-{[2-(4-chlorophenyl)imidazo[1,2-a]pyrimidin-3-yl]methyl}-3,8-diazabicyclo[3.2.1]oct-8-yl)(2-isopropyl-1,3-thiazol-4-yl)methanone<br />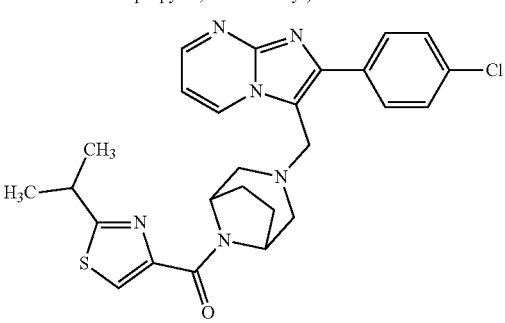<br />from 2-(4-chlorophenyl)-3-(3,8-diazabicyclo[3.2.1]oct-3-ylmethyl)imidazo[1,2-a]pyrimidine dihydrochloride and 2-isopropyl-1,3-thiazol-4-carboxylic acid | $^1$H-NMR (400 MHz, DMSO-d$_6$): δ [ppm] = 1.31 (d, 6H), 1.63-1.85 (m, 4H), 2.40-2.48 (m, 2H), 2.65 (br. d, 2H), 3.23-3.33 (m, 1H, partially obscured by H$_2$O signal), 4.04 (s, 2H), 4.59 (br. s, 1H), 4.99 (br. s, 1H), 7.14 (dd, 1H), 7.55 (d, 2H), 7.96 (d, 2H), 8.06 (s, 1H), 8.59 (dd, 1H), 9.05 (dd, 1H).<br />LC-MS (Method 1):<br />R$_t$ = 1.01 min; MS (ESIpos):<br />m/z = 507/509 [M + H]$^+$. |

-continued

| Example | Name/Structure/Starting materials | Analytical data |
|---|---|---|
| 55 | (3-{[2-(4-chlorophenyl)imidazo[1,2-a]pyrimidin-3-yl]methyl}-3,8-diazabicyclo[3.2.1]oct-8-yl)(1,3-thiazol-5-yl)methanone<br>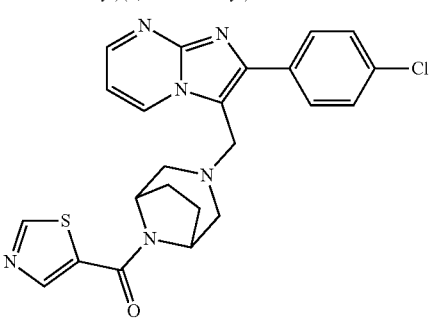<br>from 2-(4-chlorophenyl)-3-(3,8-diazabicyclo[3.2.1]oct-3-ylmethyl)imidazo[1,2-a]pyrimidine dihydrochloride and 1,3-thiazole-5-carboxylic acid | $^1$H-NMR (400 MHz, DMSO-d$_6$): δ [ppm] = 1.62-1.94 (m, 4H), 2.39-2.59 (m, 2H, partially obscured by DMSO signal), 2.68 (dd, 2H), 4.06 (s, 2H), 4.37-4.65 (m, 2H), 7.15 (dd, 1H), 7.57 (d, 2H), 7.97 (d, 2H), 8.29 (s, 1H), 8.60 (dd, 1H), 9.07 (dd, 1H), 9.23 (s, 1H).<br>LC-MS (Method 1):<br>R$_t$ = 0.77 min; MS (ESIpos):<br>m/z = 465/467 [M + H]$^+$. |
| 56 | (3-{[2-(4-chlorophenyl)imidazo[1,2-a]pyrimidin-3-yl]methyl}-3,8-diazabicyclo[3.2.1]oct-8-yl)(2,5-dimethyl-1,3-oxazol-4-yl)methanone<br>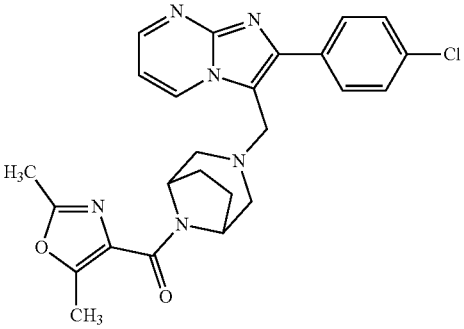<br>from 2-(4-chlorophenyl)-3-(3,8-diazabicyclo[3.2.1]oct-3-ylmethyl)imidazo[1,2-a]pyrimidine dihydrochloride and 2,5-dimethyl-1,3-oxazole-4-carboxylic acid | $^1$H-NMR (400 MHz, DMSO-d$_6$): δ [ppm] = 1.60-1.81 (m, 4H), 2.31-2.42 (m, 2H), 2.36 (s, 3H), 2.47 (s, 3H), 2.63 (br. d, 2H), 4.02 (s, 2H), 4.54 (br. s, 1H), 5.18 (br. s, 1H), 7.14 (dd, 1H), 7.56 (d, 2H), 7.97 (d, 2H), 8.59 (dd, 1H), 9.05 (dd, 1H).<br>LC-MS (Method 5):<br>R$_t$ = 1.16 min; MS (ESIpos):<br>m/z = 477/479 [M + H]$^+$. |
| 57 | (3-{[2-(4-chlorophenyl)imidazo[1,2-a]pyrimidin-3-yl]methyl}-3,8-diazabicyclo[3.2.1]oct-8-yl)[2-methoxy-4-(trifluoromethyl)-1,3-thiazol-5-yl]methanone<br>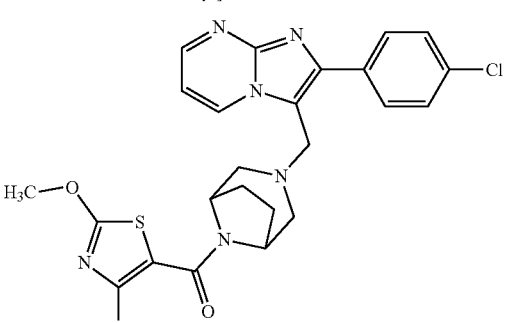<br>from 2-(4-chlorophenyl)-3-(3,8-diazabicyclo[3.2.1]oct-3-ylmethyl)imidazo[1,2-a]pyrimidine dihydrochloride and 2-methoxy-4-(trifluoromethyl)-1,3-thiazole-5-carboxylic acid | $^1$H-NMR (400 MHz, DMSO-d$_6$): δ [ppm] = 1.62-1.77 (m, 4H), 2.21-2.40 (m, 2H), 2.63 (br. d, 2H), 3.92 (br. s, 1H), 4.04 (s, 2H), 4.10 (s, 3H), 4.51 (br. s, 1H), 7.15 (dd, 1H), 7.57 (d, 2H), 7.93 (d, 2H), 8.59 (dd, 1H), 9.03 (dd, 1H).<br>LC-MS (Method 5):<br>R$_t$ = 1.30 min; MS (ESIpos):<br>m/z = 563/565 [M + H]$^+$. |

| Example | Name/Structure/Starting materials | Analytical data |
|---|---|---|
| 58 | (3-{[2-(4-chlorophenyl)imidazo[1,2-a]pyrimidin-3-yl]methyl}-3,8-diazabicyclo[3.2.1]oct-8-yl)[2-(trifluoromethyl)-1,3-thiazol-4-yl]methanone<br>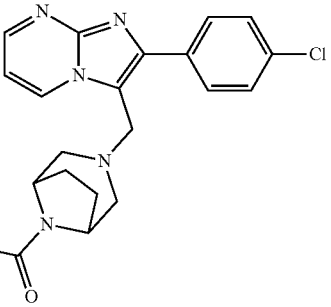<br>from 2-(4-chlorophenyl)-3-(3,8-diazabicyclo[3.2.1]oct-3-ylmethyl)imidazo[1,2-a]pyrimidine dihydrochloride and 2-(trifluoromethyl)-1,3-thiazole-4-carboxylic acid | $^1$H-NMR (400 MHz, DMSO-d$_6$): δ [ppm] = 1.65-1.89 (m, 4H), 2.45 (br. d, 2H), 2.67 (br. t, 2H), 4.05 (s, 2H), 4.61 (br. s, 1H), 4.74 (br. s, 1H), 7.15 (dd, 1H), 7.56 (d, 2H), 7.97 (d, 2H), 8.59 (dd, 1H), 8.62 (s, 1H), 9.06 (dd, 1H).<br>LC-MS (Method 5):<br>R$_t$ = 1.31 min; MS (ESIpos): m/z = 533/535 [M + H]$^+$. |
| 59 | (3-{[2-(4-chlorophenyl)imidazo[1,2-a]pyrimidin-3-yl]methyl}-3,8-diazabicyclo[3.2.1]oct-8-yl)(5-methyl-1,3-thiazol-4-yl)methanone<br>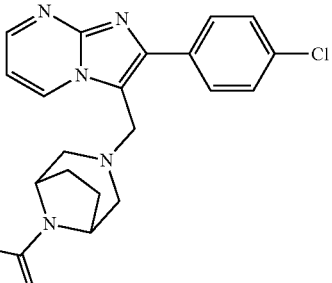<br>from 2-(4-chlorophenyl)-3-(3,8-diazabicyclo[3.2.1]oct-3-ylmethyl)imidazo[1,2-a]pyrimidine dihydrochloride and 5-methyl-1,3-thiazole-4-carboxylic acid | $^1$H-NMR (400 MHz, DMSO-d$_6$): δ [ppm] = 1.63-1.79 (m, 4H), 2.34-2.45 (m, 2H), 2.46-2.61 (m, 1H, partially obscured by DMSO signal), 2.55 (s, 3H), 2.68 (dd, 1H), 4.04 (s, 2H), 4.34 (br. s, 1H), 4.60 (br. s, 1H), 7.15 (dd, 1H), 7.57 (d, 2H), 7.96 (d, 2H), 8.59 (dd, 1H), 8.89 (s, 1H), 9.06 (dd, 1H).<br>LC-MS (Method 5):<br>R$_t$ = 1.11 min; MS (ESIpos): m/z = 479/481 [M + H]$^+$. |
| 60 | (3-{[2-(4-chlorophenyl)imidazo[1,2-a]pyrimidin-3-yl]methyl}-3,8-diazabicyclo[3.2.1]oct-8-yl)[4-(trifluoromethyl)-1,3-thiazol-2-yl]methanone<br>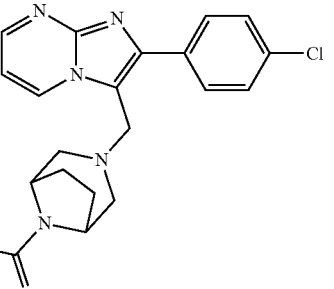<br>from 2-(4-chlorophenyl)-3-(3,8-diazabicyclo[3.2.1]oct-3-ylmethyl)imidazo[1,2-a]pyrimidine dihydrochloride and 4-(trifluoromethyl)-1,3-thiazole-2-carboxylic acid | $^1$H-NMR (400 MHz, DMSO-d$_6$): δ [ppm] = 1.68-1.80 (m, 2H), 1.83-1.95 (m, 2H), 2.45 (br. d, 1H), 2.48-2.57 (m, 1H, partially obscured by DMSO signal), 2.65 (br. d, 1H), 2.80 (br. d, 1H), 4.05 (s, 2H), 4.61 (br. s, 1H), 5.43 (br. s, 1H), 7.15 (dd, 1H), 7.55 (d, 2H), 7.97 (d, 2H), 8.60 (dd, 1H), 8.79 (s, 1H), 9.06 (dd, 1H).<br>LC-MS (Method 2):<br>R$_t$ = 2.00 min; MS (ESIpos): m/z = 533/535 [M + H]$^+$. |

| Example | Name/Structure/Starting materials | Analytical data |
|---|---|---|
| 61 | (3-{[2-(4-chlorophenyl)imidazo[1,2-a]pyrimidin-3-yl]methyl}-3,8-diazabicyclo[3.2.1]oct-8-yl)(1,3-thiazol-4-yl)methanone<br>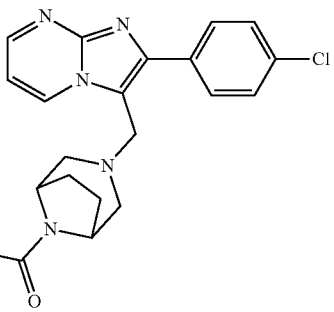<br>from 2-(4-chlorophenyl)-3-(3,8-diazabicyclo[3.2.1]oct-3-ylmethyl)imidazo[1,2-a]pyrimidine dihydrochloride and 1,3-thiazole-4-carboxylic acid | $^1$H-NMR (400 MHz, DMSO-d$_6$): δ [ppm] = 1.75 (br. d, 4H), 2.44 (br. t, 2H), 2.66 (br. t, 2H), 4.03 (s, 2H), 4.62 (br. s, 1H), 5.02 (br. s, 1H), 7.14 (dd, 1H), 7.56 (d, 2H), 7.97 (d, 2H), 8.27 (d, 1H), 8.59 (dd, 1H), 9.06 (dd, 1H), 9.15 (d, 1H).<br>LC-MS (Method 5):<br>R$_t$ = 1.07 min; MS (ESIpos):<br>m/z = 465/467 [M + H]$^+$. |
| 62 | (3-{[2-(4-isopropylphenyl)imidazo[1,2-a]pyrimidin-3-yl]methyl}-3,8-diazabicyclo[3.2.1]oct-8-yl)[6-(methylamino)pyridin-2-yl]methanone<br>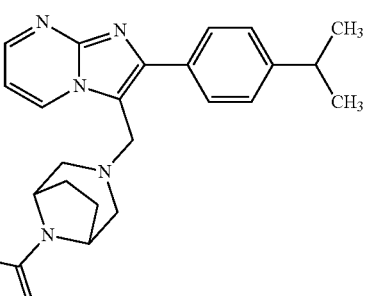<br>from 3-(3,8-diazabicyclo[3.2.1]oct-3-ylmethyl)-2-(4-isopropylphenyl)imidazo[1,2-a]pyrimidine dihydrochloride and 6-(methylamino)pyridine-2-carboxylic acid | $^1$H-NMR (400 MHz, DMSO-d$_6$): δ [ppm] = 1.25 (d, 6H), 1.64-1.81 (m, 4H), 2.41 (br. d, 1H), 2.58 (br. s, 1.75H), 2.65-2.76 (m, 4.25H), 2.88-3.01 (m, 1H), 3.98-4.09 (m, 2H), 4.60 (br. s, 1H), 4.76 (br. s, 1H), 6.51 (d, 1H), 6.65 (q, 1H), 6.80 (d, 1H), 7.12 (dd, 1H), 7.37 (d, 2H), 7.74 (d, 1H), 7.84 (d, 2H), 8.56 (dd, 1H), 9.02 (dd, 1H).<br>LC-MS (Method 2):<br>R$_t$ = 1.58 min; MS (ESIpos):<br>m/z = 496 [M + H]$^+$. |
| 63 | (3-{[2-(4-isopropylphenyl)imidazo[1,2-a]pyrimidin-3-yl]methyl}-3,8-diazabicyclo[3.2.1]oct-8-yl)(6-methoxypyridin-2-yl)methanone<br>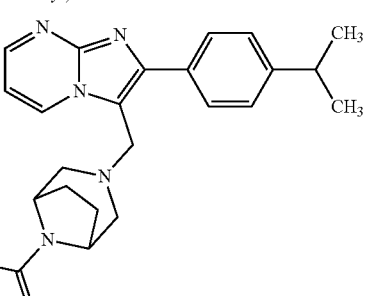<br>from 3-(3,8-diazabicyclo[3.2.1]oct-3-ylmethyl)-2-(4-isopropylphenyl)imidazo[1,2-a]pyrimidine dihydrochloride and 6-methoxypyridine-2-carboxylic acid | $^1$H-NMR (400 MHz, DMSO-d$_6$): δ [ppm] = 1.25 (d, 6H), 1.66-1.84 (m, 4H), 2.44 (br. d, 1H), 2.56-2.66 (m, 2H), 2.74 (dd, 1H), 2.95 (quin, 1H), 3.77 (s, 3H), 3.99-4.11 (m, 2H), 4.64 (br. s, 1H), 4.69 (br. s, 1H), 6.93 (d, 1H), 7.12 (dd, 1H), 7.31-7.40 (m, 3H), 7.77-7.88 (m, 3H), 8.57 (dd, 1H), 9.03 (dd, 1H).<br>LC-MS (Method 5):<br>R$_t$ = 1.24 min; MS (ESIpos):<br>m/z = 497 [M + H]$^+$. |

| Example | Name/Structure/Starting materials | Analytical data |
|---|---|---|
| 64 | (2-fluorophenyl)(3-{[2-(4-isopropylphenyl)imidazo[1,2-a]pyrimidin-3-yl]methyl}-3,8-diazabicyclo[3.2.1]oct-8-yl)methanone<br />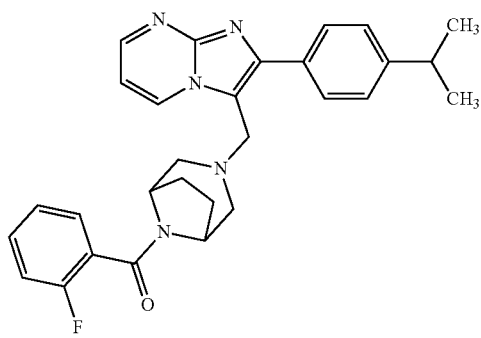<br />from 3-(3,8-diazabicyclo[3.2.1]oct-3-ylmethyl)-2-(4-isopropylphenyl)imidazo[1,2-a]pyrimidine dihydrochloride and 2-fluorobenzoic acid | H-NMR (400 MHz, DMSO-$d_6$): δ [ppm] = 1.26 (d, 6H), 1.64-1.81 (m, 4H), 2.26 (br. d, 1H), 2.42 (br. d, 1H), 2.58 (br. d, 1H), 2.68 (br. d, 1H), 2.96 (quin, 1H), 3.67 (br. s, 1H), 4.04 (s, 2H), 4.59 (br. s, 1H), 7.12 (dd, 1H), 7.23-7.32 (m, 2H), 7.38 (d, 2H), 7.41-7.54 (m, 2H), 7.83 (d, 2H), 8.56 (dd, 1H), 9.01 (dd, 1H).<br />LC-MS (Method 5):<br />$R_t$ = 1.23 min; MS (ESIpos):<br />m/z = 484 [M + H]$^+$. |
| 65 | (3-{1-[2-(4-chlorophenyl)imidazo[1,2-a]pyrimidin-3-yl]ethyl}-3,8-diazabicyclo[3.2.1]oct-8-yl)(3-fluoro-6-methoxypyridin-2-yl)methanone (racemate)<br />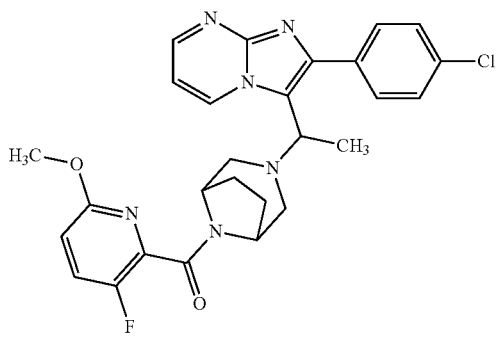<br />from 2-(4-chlorophenyl)-3-[1-(3,8-diazabicyclo[3.2.1]oct-3-yl)ethyl]imidazo[1,2-a]pyrimidine dihydrochloride (racemate) and 3-fluoro-6-methoxypyridine-2-carboxylic acid | $^1$H-NMR (400 MHz, DMSO-$d_6$): δ [ppm] = 1.41-1.60 (m, 4H), 1.61-1.75 (m, 1H), 1.76-1.90 (m, 1H), 2.01 (br. d, 0.5H), 2.06-2.24 (m, 2.5H), 2.34 (br. d, 1H), 3.12 (br. d, 0.5H), 3.23 (br. dd, 0.5H), 3.59 (s, 1.5H), 3.75 (br. d, 0.5H), 3.85 (s, 1.5H), 4.04 (br. d, 0.5H), 4.07-4.17 (m, 1H), 4.43 (br. d, 0.5H), 4.71 (br. d, 0.5H), 6.89 (dd, 0.5H), 6.98 (dd, 0.5H), 7.08-7.15 (m, 1H), 7.52-7.61 (m, 2H), 7.66-7.84 (m, 3H), 8.53-8.63 (m, 1H), 9.27 (d, 1H).<br />LC-MS (Method 2):<br />$R_t$ = 1.77 min; MS (ESIpos):<br />m/z = 521/523 [M + H]$^+$. |

-continued

| Example | Name/Structure/Starting materials | Analytical data |
|---|---|---|
| 66 | (7-{[2-(4-isopropylphenyl)imidazo[1,2-a]pyrimidin-3-yl]methyl}-3-oxa-7,9-diazabicyclo[3.3.1]non-9-yl)(6-methoxypyridin-2-yl)methanone<br>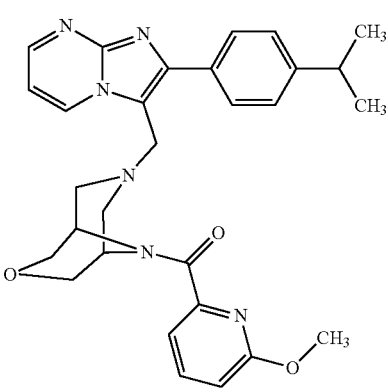<br>from 7-{[2-(4-isopropylphenyl)imidazo[1,2-a]pyrimidin-3-yl]methyl}-3-oxa-7,9-diazabicyclo[3.3.1]nonane dihydrochloride and 6-methoxypyridine-2-carboxylic acid | $^1$H-NMR (400 MHz, DMSO-d$_6$): δ [ppm] = 1.25 (d, 6H), 2.44-2.65 (m, 2H, partially obscured by DMSO signal), 2.86-3.00 (m, 2H), 3.05 (br. d, 1H), 3.66-3.82 (m, 3H), 3.80 (s, 3H), 3.89 (d, 1H), 3.94-4.06 (m, 2H), 4.20 (br. s, 1H), 4.45 (br. s, 1H), 6.92 (d, 1H), 7.06 (dd, 1H), 7.29 (d, 1H), 7.36 (d, 2H), 7.75-7.87 (m, 3H), 8.55 (dd, 1H), 9.28 (dd, 1H).<br>LC-MS (Method 1):<br>R$_t$ = 0.82 min; m/z = 513 (M + H)$^+$. |
| 67 | (3-chloro-6-methoxypyridin-2-yl)(7-{[2-(4-isopropylphenyl)imidazo[1,2-a]pyrimidin-3-yl]methyl}-3-oxa-7,9-diazabicyclo[3.3.1]non-9-yl)methanone<br>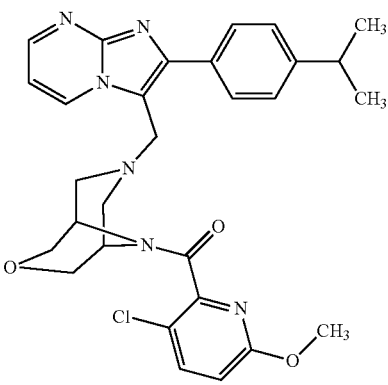<br>from 7-{[2-(4-isopropylphenyl)imidazo[1,2-a]pyrimidin-3-yl]methyl}-3-oxa-7,9-diazabicyclo[3.3.1]nonane dihydrochloride and 3-chloro-6-methoxypyridine-2-carboxylic acid | $^1$H-NMR (400 MHz, DMSO-d$_6$): δ [ppm] = 1.26 (d, 6H), 2.44-2.57 (m, 2H, obscured by DMSO signal), 2.84-3.00 (m, 2H), 3.06 (br. d, 1H), 3.34 (br. s, 1H, partially obscured by H$_2$O signal), 3.61-3.75 (m, 3H), 3.82 (s, 3H), 3.88 (d, 1H), 3.99 (s, 2H), 4.44 (br. s, 1H), 6.93 (d, 1H), 7.05 (dd, 1H), 7.36 (d, 2H), 7.80 (d, 2H), 8.55 (dd, 1H), 9.28 (dd, 1H).<br>LC-MS (Method 1):<br>R$_t$ = 0.88 min; m/z = 547/549 (M + H)$^+$. |

| Example | Name/Structure/Starting materials | Analytical data |
|---|---|---|
| 68 | (2-fluorophenyl)(7-{[2-(4-isopropylphenyl)imidazo[1,2-a]pyrimidin-3-yl]methyl}-3-oxa-7,9-diazabicyclo[3.3.1]non-9-yl)methanone<br>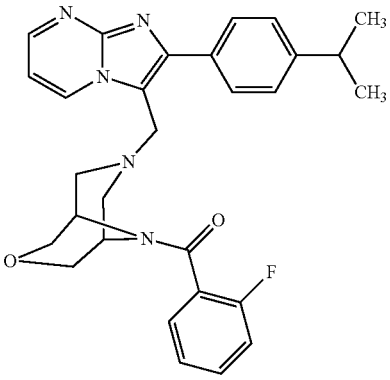<br>from 7-{[2-(4-isopropylphenyl)imidazo[1,2-a]pyrimidin-3-yl]methyl}-3-oxa-7,9-diazabicyclo[3.3.1]nonane dihydrochloride and 2-fluorobenzoic acid | $^1$H-NMR (400 MHz, DMSO-$d_6$): δ [ppm] = 1.26 (d, 6H), 2.41 (br. d, 1H), 2.46-2.58 (m, 1H, obscured by DMSO signal), 2.84-3.06 (m, 3H), 3.37 (br. s, 1H), 3.59 (br. d, 1H), 3.71 (br. t, 2H), 3.87 (d, 1H), 3.99 (s, 2H), 4.47 (br. s, 1H), 7.05 (dd, 1H), 7.24-7.33 (m, 2H), 7.37 (d, 2H), 7.42-7.54 (m, 2H), 7.79 (d, 2H), 8.55 (dd, 1H), 9.28 (dd, 1H).<br>LC-MS (Method 1):<br>R$_t$ = 0.84 min; m/z = 500 (M + H)$^+$. |
| 69 | (3-chloro-6-methoxypyridin-2-yl)(5-{[2-(4-isopropylphenyl)imidazo[1,2-a]pyrimidin-3-yl]methyl}-2,5-diazabicyclo[2.2.2]oct-2-yl)methanone (Enantiomer 1)<br>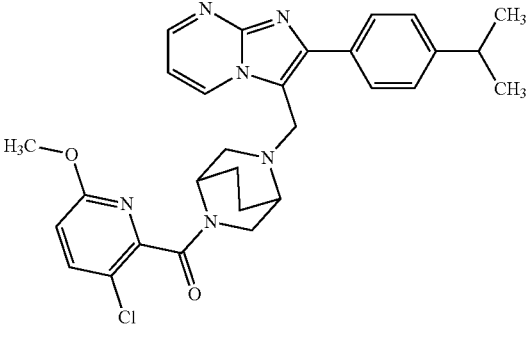<br>from 3-(2,5-diazabicyclo[2.2.2]oct-2-ylmethyl)-2-(4-isopropylphenyl)imidazo[1,2-a]pyrimidine dihydrochloride (Enantiomer 1) and 3-chloro-6-methoxypyridine-2-carboxylic acid | $^1$H-NMR (400 MHz, DMSO-$d_6$): δ [ppm] = 1.19-1.31 (m, 6H), 1.52-2.00 (m, 4H), 2.62 (br. dd, 0.75H), 2.70-2.85 (m, 1.5H), 2.89-3.03 (m, 2H), 3.21 (br. s, 0.75H), 3.43 (br. d, 1H), 3.70-3.86 (m, 3.75H), 4.22-4.35 (m, 2H), 4.38 (br. s, 0.25H), 6.85-6.96 (m, 1H), 7.05-7.15 (m, 1H), 7.30-7.40 (m, 2H), 7.70-7.86 (m, 2.7H), 7.90 (d, 0.3H), 8.56 (dd, 1H), 8.94-9.04 (m, 1H).<br>LC-MS (Method 2):<br>R$_t$ = 1.73 min; m/z = 531/533 (M + H)$^+$. |

| Example | Name/Structure/Starting materials | Analytical data |
|---|---|---|
| 70 | (5-cyclopropyl-1,3-oxazol-4-yl)(5-{[2-(4-isopropylphenyl)imidazo[1,2-a]pyrimidin-3-yl]methyl}-2,5-diazabicyclo[2.2.2]oct-2-yl)methanone (Enantiomer 1)<br>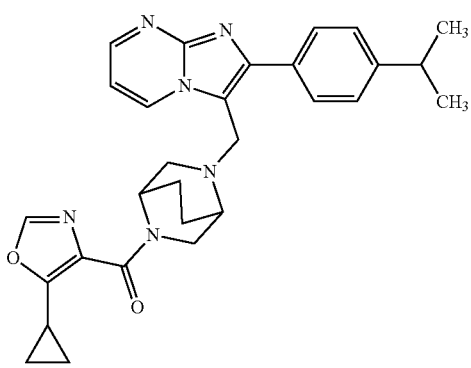<br>from 3-(2,5-diazabicyclo[2.2.2]oct-2-ylmethyl)-2-(4-isopropylphenyl)imidazo[1,2-a]pyrimidine dihydrochloride (Enantiomer 1) and 5-cyclopropyl-1,3-oxazole-4-carboxylic acid | $^1$H-NMR (400 MHz, DMSO-$d_6$): δ [ppm] = 0.81-0.95 (m, 2H), 0.96-1.09 (m, 2H), 1.25 (d, 6H), 1.49-1.63 (m, 1H), 1.66-2.00 (m, 3H), 2.44-2.57 (m, 0.7H, partially obscured by DMSO signal), 2.57-2.65 (m, 0.3H), 2.73-3.02 (m, 4H), 3.36 (dd, 0.7H), 3.63-3.76 (m, 1H), 4.04 (br. d, 0.3H), 4.22-4.33 (m, 2H), 4.36 (br. s, 0.3H), 4.59 (br. s, 0.7H), 7.06-7.14 (m, 1H), 7.31-7.40 (m, 2H), 7.75-7.83 (m, 2H), 8.12-8.19 (m, 1H), 8.53-8.60 (m, 1H), 8.98-9.06 (m, 1H).<br>LC-MS (Method 2):<br>$R_t$ = 1.52 min; m/z = 497 (M + H)$^+$. |
| 71 | (3-fluoro-6-methoxypyridin-2-yl)(5-{[2-(4-isopropylphenyl)imidazo[1,2-a]pyrimidin-3-yl]methyl}-2,5-diazabicyclo[2.2.2]oct-2-yl)methanone (Enantiomer 1)<br>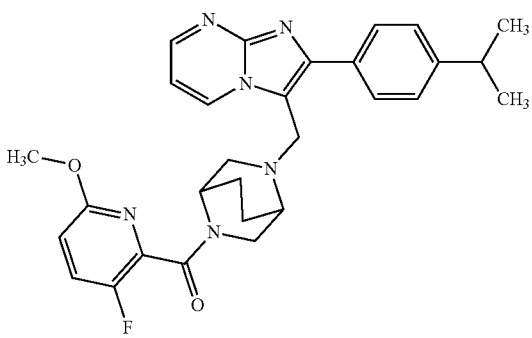<br>from 3-(2,5-diazabicyclo[2.2.2]oct-2-ylmethyl)-2-(4-isopropylphenyl)imidazo[1,2-a]pyrimidine dihydrochloride (Enantiomer 1) and 3-fluoro-6-methoxypyridine-2-carboxylic acid | $^1$H-NMR (400 MHz, DMSO-$d_6$): δ [ppm] = 1.20-1.30 (m, 6H), 1.50-2.01 (m, 4H), 2.69 (br. dd, 0.75H), 2.74 (br. s, 0.25H), 2.77-2.88 (m, 1.25H), 2.90-3.01 (m, 1.75H), 3.13 (br. d, 0.25H), 3.39-3.52 (m, 1.5H), 3.61 (d, 0.25H), 3.69-3.84 (m, 3.75H), 4.21-4.35 (m, 2H), 4.36-4.42 (m, 0.25H), 6.88-6.98 (m, 1H), 7.05-7.15 (m, 1H), 7.30-7.40 (m, 2H), 7.70-7.83 (m, 3H), 8.52-8.60 (m, 1H), 8.96-9.06 (m, 1H).<br>LC-MS (Method 2):<br>$R_t$ = 1.62 min; m/z = 515 (M + H)$^+$. |

| Example | Name/Structure/Starting materials | Analytical data |
|---|---|---|
| 72 | (3-fluoro-6-methoxypyridin-2-yl)(5-{[2-(4-isopropylphenyl)imidazo[1,2-a]pyrimidin-3-yl]methyl}-2,5-diazabicyclo[2.2.2]oct-2-yl)methanone (Enantiomer 2)<br>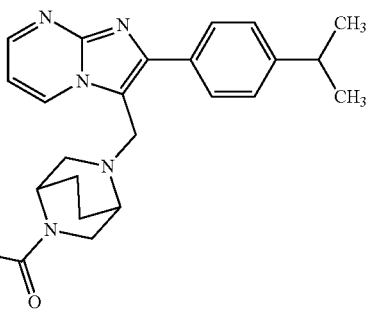<br>from 3-(2,5-diazabicyclo[2.2.2]oct-2-ylmethyl)-2-(4-isopropylphenyl)imidazo[1,2-a]pyrimidine dihydrochloride (Enantiomer 2) and 3-fluoro-6-methoxypyridine-2-carboxylic acid | $^1$H-NMR (400 MHz, DMSO-d$_6$): δ [ppm] = 1.20-1.31 (m, 6H), 1.51-2.01 (m, 4H), 2.69 (br. dd, 0.75H), 2.74 (br. s, 0.25H), 2.77-2.87 (m, 1.25H), 2.89-3.02 (m, 1.75H), 3.14 (br. d, 0.25H), 3.39-3.52 (m, 1.5H), 3.61 (d, 0.25H), 3.69-3.83 (m, 3.75H), 4.21-4.35 (m, 2H), 4.36-4.42 (m, 0.25H), 6.88-6.98 (m, 1H), 7.05-7.15 (m, 1H), 7.30-7.41 (m, 2H), 7.70-7.84 (m, 3H), 8.53-8.60 (m, 1H), 8.96-9.05 (m, 1H).<br>LC-MS (Method 2):<br>R$_t$ = 1.63 min; m/z = 515 (M + H)$^+$. |
| 73 | (5-{[2-(4-isopropylphenyl)imidazo[1,2-a]pyrimidin-3-yl]methyl}-2,5-diazabicyclo[2.2.2]oct-2-yl)(6-methoxypyridin-2-yl)methanone (Enantiomer 1)<br>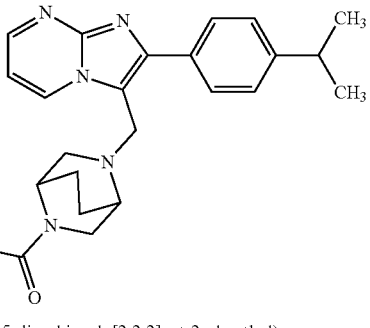<br>from 3-(2,5-diazabicyclo[2.2.2]oct-2-ylmethyl)-2-(4-isopropylphenyl)imidazo[1,2-a]pyrimidine dihydrochloride (Enantiomer 1) and 6-methoxypyridine-2-carboxylic acid | $^1$H-NMR (400 MHz, DMSO-d$_6$): δ [ppm] = 1.25 (d, 6H), 1.49-2.01 (m, 4H), 2.69-2.76 (m, 1H), 2.83-3.02 (m, 3H), 3.39 (dd, 0.75H), 3.47 (br. d, 0.25H), 3.70-3.86 (m, 3.75H), 3.93-4.04 (m, 1H), 4.23-4.35 (m, 2H), 4.39 (br. s, 0.25H), 6.84-6.95 (m, 1H), 7.05-7.14 (m, 1H), 7.17 (d, 0.75H), 7.26-7.40 (m, 2.25H), 7.73-7.85 (m, 3H), 8.52-8.60 (m, 1H), 8.97-9.06 (m, 1H).<br>LC-MS (Method 2):<br>R$_t$ = 1.56 min; m/z = 497 (M + H)$^+$. |
| 74 | (5-{[2-(4-isopropylphenyl)imidazo[1,2-a]pyrimidin-3-yl]methyl}-2,5-diazabicyclo[2.2.2]oct-2-yl)(6-methoxypyridin-2-yl)methanone (Enantiomer 2)<br>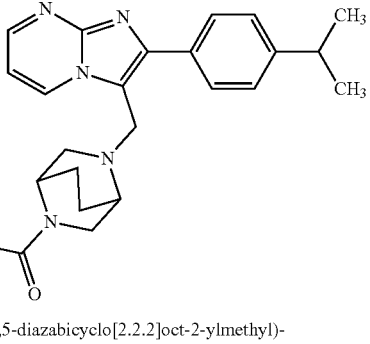<br>from 3-(2,5-diazabicyclo[2.2.2]oct-2-ylmethyl)-2-(4-isopropylphenyl)imidazo[1,2-a]pyrimidine dihydrochloride (Enantiomer 2) and 6-methoxypyridine-2-carboxylic acid | $^1$H-NMR (400 MHz, DMSO-d$_6$): δ [ppm] = 1.25 (d, 6H), 1.49-2.01 (m, 4H), 2.69-2.76 (m, 1H), 2.82-3.01 (m, 3H), 3.39 (dd, 0.75H), 3.47 (br. d, 0.25H), 3.70-3.85 (m, 3.75H), 3.93-4.02 (m, 1H), 4.23-4.35 (m, 2H), 4.39 (br. s, 0.25H), 6.84-6.94 (m, 1H), 7.05-7.14 (m, 1H), 7.17 (d, 0.75H), 7.25-7.40 (m, 2.25H), 7.73-7.85 (m, 3H), 8.52-8.60 (m, 1H), 8.97-9.05 (m, 1H).<br>LC-MS (Method 2):<br>R$_t$ = 1.55 min; m/z = 497 (M + H)$^+$. |

| Example | Name/Structure/Starting materials | Analytical data |
|---|---|---|
| 75 | [6-(difluoromethoxy)pyridin-2-yl](5-{[2-(4-isopropylphenyl)imidazo[1,2-a]pyrimidin-3-yl]methyl}-2,5-diazabicyclo[2.2.2]oct-2-yl)methanone (Enantiomer 2)<br><br>from 3-(2,5-diazabicyclo[2.2.2]oct-2-ylmethyl)-2-(4-isopropylphenyl)imidazo[1,2-a]pyrimidine dihydrochloride (Enantiomer 2) and 6-(difluoromethoxy)pyridine-2-carboxylic acid | $^1$H-NMR (400 MHz, DMSO-d$_6$): δ [ppm] = 1.20-1.29 (m, 6H), 1.50-2.01 (m, 4H), 2.71 (dd, 0.75H), 2.75 (br. s, 0.25H), 2.83-3.01 (m, 3H), 3.39 (dd, 0.75H), 3.47 (br. d, 0.25H), 3.73 (d, 0.75H), 3.93 (br. s, 1H), 4.23-4.34 (m, 2H), 4.39 (br. s, 0.25H), 7.05-7.13 (m, 1H), 7.14-7.22 (m, 1H), 7.31-7.41 (m, 2.25H), 7.45 (d, 0.75H), 7.48-7.71 (m, 1H), 7.75-7.82 (m, 2H), 7.97-8.09 (m, 1H), 8.53-8.60 (m, 1H), 8.96-9.05 (m, 1H).<br>LC-MS (Method 2):<br>R$_t$ = 1.68 min; m/z = 533 (M + H)$^+$. |
| 76 | [6-(difluoromethoxy)pyridin-2-yl](5-{[2-(4-isopropylphenyl)imidazo[1,2-a]pyrimidin-3-yl]methyl}-2,5-diazabicyclo[2.2.2]oct-2-yl)methanone (Enantiomer 1)<br><br>from 3-(2,5-diazabicyclo[2.2.2]oct-2-ylmethyl)-2-(4-isopropylphenyl)imidazo[1,2-a]pyrimidine dihydrochloride (Enantiomer 1) and 6-(difluoromethoxy)pyridine-2-carboxylic acid | $^1$H-NMR (400 MHz, DMSO-d$_6$): δ [ppm] = 1.20-1.30 (m, 6H), 1.50-2.01 (m, 4H), 2.71 (dd, 0.75H), 2.75 (br. s, 0.25H), 2.82-3.02 (m, 3H), 3.39 (dd, 0.75H), 3.47 (br. d, 0.25H), 3.73 (d, 0.75H), 3.93 (br. s, 1H), 4.23-4.35 (m, 2H), 4.38 (br. s, 0.25H), 7.05-7.13 (m, 1H), 7.14-7.23 (m, 1H), 7.31-7.41 (m, 2.25H), 7.45 (d, 0.75H), 7.49-7.71 (m, 1H), 7.75-7.83 (m, 2H), 7.97-8.09 (m, 1H), 8.52-8.60 (m, 1H), 8.96-9.07 (m, 1H).<br>LC-MS (Method 2):<br>R$_t$ = 1.69 min; m/z = 533 (M + H)$^+$. |
| 77 | (5-{[2-(4-isopropylphenyl)imidazo[1,2-a]pyrimidin-3-yl]methyl}-2,5-diazabicyclo[2.2.2]oct-2-yl)(6-methoxy-3-methylpyridin-2-yl)methanone (Enantiomer 2)<br><br>from 3-(2,5-diazabicyclo[2.2.2]oct-2-ylmethyl)-2-(4-isopropylphenyl)imidazo[1,2-a]pyrimidine dihydrochloride (Enantiomer 2) and 6-methoxy-3-methylpyridine-2-carboxylic acid | $^1$H-NMR (400 MHz, DMSO-d$_6$): δ [ppm] = 1.20-1.31 (m, 6H), 1.51-2.00 (m, 4H), 2.03-2.12 (m, 3H), 2.63 (dd, 0.75H), 2.70-2.77 (m, 1H), 2.81 (d, 0.5H), 2.89-3.03 (m, 2H), 3.24 (br. s, 0.75H), 3.42 (br. d, 1H), 3.65-3.84 (m, 3.75H), 4.20-4.34 (m, 2H), 4.37-4.43 (m, 0.25H), 6.71-6.80 (m, 1H), 7.06-7.14 (m, 1H), 7.29-7.41 (m, 2H), 7.54-7.65 (m, 1H), 7.72-7.83 (m, 2H), 8.52-8.60 (m, 1H), 8.95-9.05 (m, 1H).<br>LC-MS (Method 6):<br>R$_t$ = 1.68 min; m/z = 511 (M + H)$^+$. |

| Example | Name/Structure/Starting materials | Analytical data |
|---|---|---|
| 78 | (5-{[2-(4-isopropylphenyl)imidazo[1,2-a]pyrimidin-3-yl]methyl}-2,5-diazabicyclo[2.2.2]oct-2-yl)(6-methoxy-3-methylpyridin-2-yl)methanone (Enantiomer 1)<br>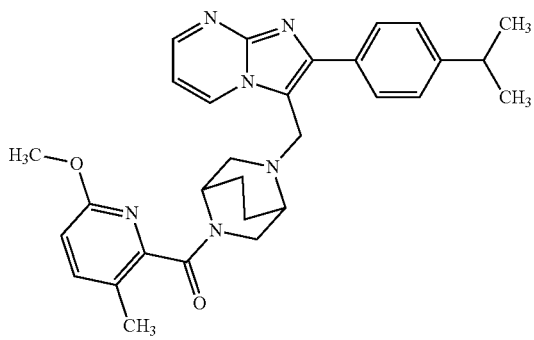<br>from 3-(2,5-diazabicyclo[2.2.2]oct-2-ylmethyl)-2-(4-isopropylphenyl)imidazo[1,2-a]pyrimidine dihydrochloride (Enantiomer 1) and 6-methoxy-3-methylpyridine-2-carboxylic acid | $^1$H-NMR (400 MHz, DMSO-d$_6$): δ [ppm] = 1.19-1.31 (m, 6H), 1.51-2.00 (m, 4H), 2.02-2.14 (m, 3H), 2.63 (dd, 0.75H), 2.69-2.78 (m, 1H), 2.81 (d, 0.5H), 2.89-3.03 (m, 2H), 3.24 (br. s, 0.75H), 3.42 (br. d, 1H), 3.65-3.84 (m, 3.75H), 4.20-4.35 (m, 2H), 4.37-4.43 (m, 0.25H), 6.70-6.80 (m, 1H), 7.06-7.15 (m, 1H), 7.30-7.40 (m, 2H), 7.54-7.64 (m, 1H), 7.72-7.83 (m, 2H), 8.53-8.60 (m, 1H), 8.94-9.05 (m, 1H).<br>LC-MS (Method 6):<br>R$_t$ = 1.68 min; m/z = 511 (M + H)$^+$. |
| 79 | (5-{[2-(4-bromophenyl)imidazo[1,2-a]pyrimidin-3-yl]methyl}-2,5-diazabicyclo[2.2.2]oct-2-yl)(2-fluorophenyl)methanone (racemate)<br>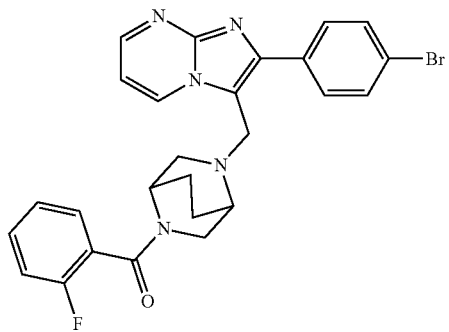<br>from 2-(4-bromophenyl)-3-(2,5-diazabicyclo[2.2.2]oct-2-ylmethyl)imidazo[1,2-a]pyrimidine dihydrochloride (racemate) and 2-fluorobenzoic acid | $^1$H-NMR (400 MHz, DMSO-d$_6$): δ [ppm] = 1.45-2.01 (m, 4H), 2.44-2.57 (m, 0.5H), 2.59-2.86 (m, 2.5H), 2.89-3.07 (m, 1H), 3.36-3.49 (m, 1H), 3.77 (br. d, 0.7H), 4.17-4.43 (m, 2.3H), 7.04-7.19 (m, 1H), 7.18-7.39 (m, 3H), 7.40-7.58 (m, 1H), 7.62-7.75 (m, 2H), 7.76-7.91 (m, 2H), 8.54-8.63 (m, 1H), 8.96-9.07 (m, 1H).<br>LC-MS (Method 2):<br>R$_t$ = 1.54 min; m/z = 520/522 (M + H)$^+$. |

| Example | Name/Structure/Starting materials | Analytical data |
|---|---|---|
| 80 | (5-{[2-(4-bromophenyl)imidazo[1,2-a]pyrimidin-3-yl]methyl}-2,5-diazabicyclo[2.2.2]oct-2-yl)(cyclopentyl)methanone (racemate)<br>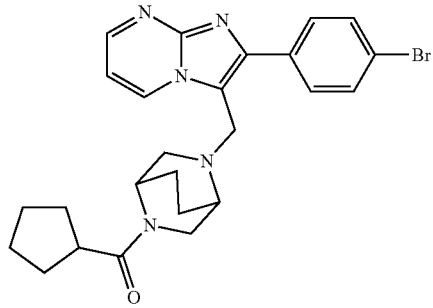<br>from 2-(4-bromophenyl)-3-(2,5-diazabicyclo[2.2.2]oct-2-ylmethyl)imidazo [1,2-a]pyrimidine dihydrochloride (racemate) and cyclopentanecarboxylic acid | $^1$H-NMR (400 MHz, DMSO-d$_6$): δ [ppm] = -0.149 (0.54), -0.008 (4.35), 0.008 (3.57), 0.146 (0.49), 1.468 (2.71), 1.487 (3.20), 1.501 (3.94), 1.516 (4.35), 1.528 (4.98), 1.538 (4.91), 1.552 (4.91), 1.578 (3.45), 1.589 (3.88), 1.605 (4.88), 1.624 (5.35), 1.643 (3.91), 1.685 (3.00), 1.707 (4.06), 1.726 (3.25), 1.750 (1.24), 1.876 (1.41), 2.328 (0.63), 2.646 (0.95), 2.671 (2.30), 2.714 (7.31), 2.746 (4.33), 2.775 (1.34), 2.793 (1.64), 2.822 (3.00), 3.172 (2.01), 3.199 (2.37), 3.359 (1.56), 3.382 (1.69), 3.527 (1.95), 3.558 (1.66), 3.731 (1.41), 3.757 (1.20), 3.926 (2.76), 4.199 (1.20), 4.236 (6.26), 4.243 (9.84), 4.251 (6.91), 4.287 (1.22), 7.110 (4.45), 7.120 (4.69), 7.127 (4.62), 7.138 (4.61), 7.680 (11.67), 7.701 (16.00), 7.815 (8.75), 7.818 (11.65), 7.836 (7.72), 7.839 (7.96), 8.585 (4.37), 8.591 (4.13), 8.595 (4.20), 9.014 (3.08), 9.018 (5.06), 9.023 (2.68), 9.031 (3.23), 9.036 (4.89), 9.040 (2.42).<br>LC-MS (Method 2): R$_t$ = 1.45 min; m/z = 494/496 (M + H)$^+$. |
| 81 | (5-{[2-(4-bromophenyl)imidazo[1,2-a]pyrimidin-3-yl]methyl}-2,5-diazabicyclo[2.2.2]oct-2-yl)(3-fluoro-6-methoxypyridin-2-yl)methanone (racemate)<br>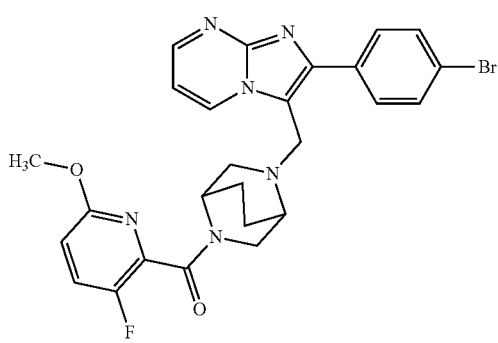<br>from 2-(4-bromophenyl)-3-(2,5-diazabicyclo[2.2.2]oct-2-ylmethyl)imidazo[1,2-a]pyrimidine dihydrochloride (racemate) and 3-fluoro-6-methoxypridine-2-carboxylic acid | $^1$H-NMR (400 MHz, DMSO-d$_6$): δ [ppm] = 1.52-1.99 (m, 4H), 2.67 (dd, 0.75H), 2.72 (br. s, 0.25H), 2.77-2.86 (m, 1.25H), 2.93 (br. s, 0.75H), 3.15 (br. d, 0.25H), 3.43 (dd, 0.75H), 3.48 (br. s, 0.75H), 3.57 (br. d, 0.25H), 3.70-3.83 (m, 3.75H), 4.22-4.34 (m, 2H), 4.36-4.41 (m, 0.25H), 6.89-6.99 (m, 1H), 7.08-7.17 (m, 1H), 7.64-7.88 (m, 5H), 8.57-8.62 (m, 1H), 9.00-9.08 (m, 1H).<br>LC-MS (Method 2):<br>R$_t$ = 1.55 min; m/z = 551/553 (M + H)$^+$. |

| Example | Name/Structure/Starting materials | Analytical data |
|---|---|---|
| 82 | (3-{[2-(4-bromophenyl)imidazo[1,2-a]pyrimidin-3-yl]methyl}-3,8-diazabicyclo[3.2.1]oct-8-yl)(3-fluoro-6-methoxypyridin-2-yl)methanone<br><br>from 2-(4-bromophenyl)-3-(3,8-diazabicyclo[3.2.1]oct-3-ylmethyl)imidazo[1,2-a]pyrimidine dihydrochloride and 3-fluoro-6-methoxypridine-2-carboxylic acid | $^1$H-NMR (400 MHz, DMSO-d$_6$): δ [ppm] = 1.60-1.83 (m, 4H), 2.39-2.58 (m, 3H, partially obscured by DMSO signal), 2.75 (dd, 1H), 3.76 (s, 3H), 3.91 (br. s, 1H), 4.00-4.13 (m, 2H), 4.60 (br. s, 1H), 6.95 (dd, 1H), 7.14 (dd, 1H), 7.70 (d, 2H), 7.77 (t, 1H), 7.89 (d, 2H), 8.59 (dd, 1H), 9.06 (dd, 1H).<br>LC-MS (Method 1):<br>R$_t$ = 0.93 min; m/z = 551/553 (M + H)$^+$. |
| 83 | (3-{[2-(4-bromophenyl)imidazo[1,2-a]pyrimidin-3-yl]methyl}-3,8-diazabicyclo[3.2.1]oct-8-yl)(2-fluorophenyl)methanone<br><br>from 2-(4-bromophenyl)-3-(3,8-diazabicyclo[3.2.1]oct-3-ylmethyl)imidazo[1,2-a]pyrimidine dihydrochloride and 2-fluorobenzoic acid | $^1$H-NMR (400 MHz, DMSO-d$_6$): δ [ppm] = 1.64-1.81 (m, 4H), 2.24 (br. d, 1H), 2.42 (br. d, 1H), 2.47-2.60 (m, 1H, partially obscured by DMSO signal), 2.68 (br. d, 1H), 3.66 (br. s, 1H), 4.04 (s, 2H), 4.59 (br. s, 1H), 7.14 (dd, 1H), 7.24-7.32 (m, 2H), 7.40-7.55 (m, 2H), 7.70 (d, 2H), 7.88 (d, 2H), 8.59 (dd, 1H), 9.04 (dd, 1H).<br>LC-MS (Method 1):<br>R$_t$ = 0.93 min; m/z = 520/522 (M + H)$^+$. |
| 84 | (3-{[2-(4-bromophenyl)imidazo[1,2-a]pyrimidin-3-yl]methyl}-3,8-diazabicyclo[3.2.1]oct-8-yl)(cyclopentyl)methanone<br><br>from 2-(4-bromophenyl)-3-(3,8-diazabicyclo[3.2.1]oct-3-ylmethyl)imidazo[1,2-a]pyrimidine dihydrochloride and cyclopentanecarboxylic acid | $^1$H-NMR (400 MHz, DMSO-d$_6$): δ [ppm] = 1.44-1.66 (m, 7H), 1.66-1.80 (m, 5H), 2.26 (br. dd, 2H), 2.46-2.65 (m, 2H, partially obscured by DMSO signal), 2.80-2.91 (m, 1H), 3.95-4.05 (m, 2H), 4.28 (br. s, 1H), 4.37-4.44 (m, 1H), 7.14 (dd, 1H), 7.70 (d, 2H), 7.90 (d, 2H), 8.59 (dd, 1H), 9.05 (dd, 1H).<br>LC-MS (Method 1):<br>R$_t$ = 0.97 min; m/z = 494/496 (M + H)$^+$. |

Example 85

3-{[2-(4-Chlorophenyl)imidazo[1,2-a]pyrimidin-3-yl]methyl}-N-(2,4-difluorophenyl)-3,8-diazabicyclo[3.2.1]octane-8-carboxamide

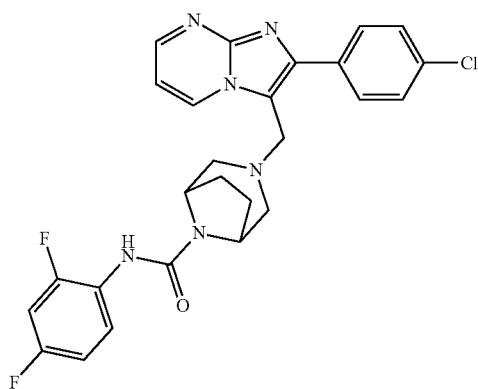 [SMILES: O=C(Nc1ccc(F)cc1F)N1C2CCC1CN(Cc1c(-c3ccc(Cl)cc3)nc3ncccn13)C2]

15.5 mg (0.10 mmol) of 2,4-difluorophenyl isocyanate were initially charged in a well of a 96-well multititre plate and cooled to 0° C. Separately, 46.3 mg of 2-(4-chlorophenyl)-3-(3,8-diazabicyclo[3.2.1]oct-3-ylmethyl)imidazo[1,2-a]pyrimidine dihydrochloride were dissolved in 0.8 ml of 1,2-dichloroethane, 0.052 ml (0.3 mmol) of N,N-diisopropylethylamine was added, and the mixture was cooled to 8° C. The two solutions were combined in the multititer plate, 4 Å molecular sieve was added and first subjected to agitation at 0° C. for 1 h. Subsequently, the mixture was allowed to warm up to RT and agitated at RT overnight. Thereafter, the solvent was removed completely by means of a centrifugal dryer. The residue was dissolved in 0.6 ml of DMF and filtered, and the filtrate was separated into its components by preparative LC-MS by one of the following methods:

MS instrument: Waters, HPLC instrument: Waters; column: Phenomenex Luna 5μ C18(2) 100A, AXIA Tech., 50 mm×21.2 mm; mobile phase A: water, mobile phase B: acetonitrile, with mobile phase gradient; flow rate: 38.5 ml/min+1.5 ml/min 10% aq. formic acid; UV detection: DAD, 210-400 nm or MS instrument: Waters, HPLC instrument: Waters; column: Phenomenex Luna 5μ C18(2) 100A, AXIA Tech., 50 mm×21.2 mm; mobile phase A: water, mobile phase B: methanol, with mobile phase gradient; flow rate: 38.5 ml/min+1.5 ml/min 10% ammonia in water; UV detection: DAD, 210-400 nm.

In this way, 17.9 mg (35% of theory, 100% purity) of the title compound were obtained.

LC-MS (Method 7, ESIpos): $R_t$=1.14 min; m/z=509 (M+H)$^+$.

In a parallel synthetic manner analogous to Example 85, the following compounds were prepared starting from 2-(4-chlorophenyl)-3-(3,8-diazabicyclo[3.2.1]oct-3-ylmethyl)imidazo[1,2-a]pyrimidine dihydrochloride and the appropriate isocyanate, carbamoyl chloride or chloroformate:

| Example | Name/structure (yield, purity) | LC-MS (Method 7) |
|---|---|---|
| 86 | 3-{[2-(4-chlorophenyl)imidazo[1,2-a]pyrimidin-3-yl]methyl}-N-isopropyl-3,8-diazabicyclo[3.2.1]octane-8-carboxamide<br><br>11.1 mg (90% purity, 23% of theory) | $R_t$ = 1.03 min; m/z = 439 [M + H]$^+$ |

| Example | Name/structure (yield, purity) | LC-MS (Method 7) |
|---|---|---|
| 87 | 3-{[2-(4-chlorophenyl)imidazo[1,2-a]pyrimidin-3-yl]methyl}-N-cyclopropyl-3,8-diazabicyclo[3.2.1]octane-8-carboxamide<br><br>900 µg (100% purity, 2% of theory) | $R_t$ = 0.99 min; m/z = 437 [M + H]$^+$ |
| 88 | 3-{[2-(4-chlorophenyl)imidazo[1,2-a]pyrimidin-3-yl]methyl}-N-(2,5-dichloro-4-methoxyphenyl)-3,8-diazabicyclo[3.2.1]octane-8-carboxamide<br><br>8.3 mg (90% purity, 13% of theory) | $R_t$ = 1.22 min; m/z = 571 [M + H]$^+$ |
| 89 | N-(3-chlorophenyl)-3-{[2-(4-chlorophenyl)imidazo[1,2-a]pyrimidin-3-yl]methyl}-3,8-diazabicyclo[3.2.1]octane-8-carboxamide<br><br>9.7 mg (100% purity, 19% of theory) | $R_t$ = 1.19 min; m/z = 507 [M + H]$^+$ |

| Example | Name/structure (yield, purity) | LC-MS (Method 7) |
|---|---|---|
| 90 | 3-{[2-(4-chlorophenyl)imidazo[1,2-a]pyrimidin-3-yl]methyl}-N-(2,6-difluorobenzyl)-3,8-diazabicyclo[3.2.1]octane-8-carboxamide 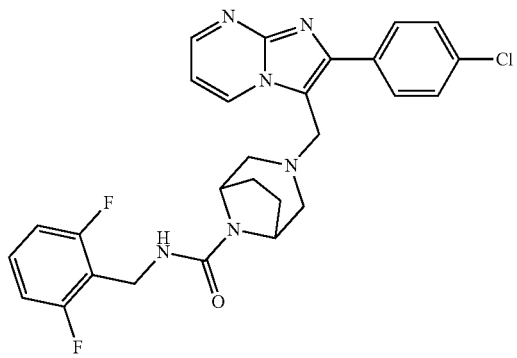 17.2 mg (100% purity, 33% of theory) | $R_t$ = 1.14 min; m/z = 523 [M + H]$^+$ |
| 91 | 3-{[2-(4-chlorophenyl)imidazo[1,2-a]pyrimidin-3-yl]methyl}-N-(2,6-dichlorophenyl)-3,8-diazabicyclo[3.2.1]octane-8-carboxamide 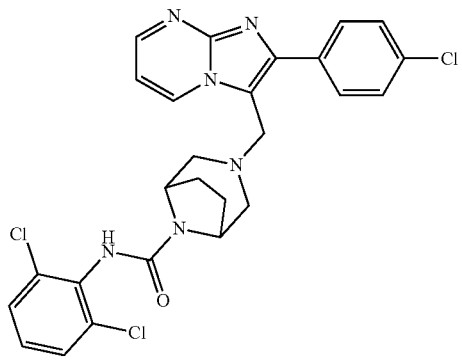 16.4 mg (98% purity, 30% of theory) | $R_t$ = 1.15 min; m/z = 541 [M + H]$^+$ |
| 92 | 3-{[2-(4-chlorophenyl)imidazo[1,2-a]pyrimidin-3-yl]methyl}-N-(2,6-dimethylphenyl)-3,8-diazabicyclo[3.2.1]octane-8-carboxamide 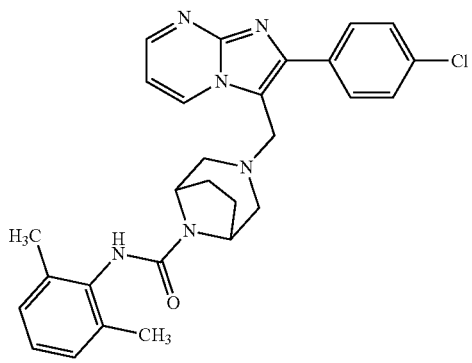 18.5 mg (99% purity, 37% of theory) | $R_t$ = 1.14 min; m/z = 501 [M + H]$^+$ |

| Example | Name/structure (yield, purity) | LC-MS (Method 7) |
|---|---|---|
| 93 | 3-{[2-(4-chlorophenyl)imidazo[1,2-a]pyrimidin-3-yl]methyl}-N-(2-fluorophenyl)-3,8-diazabicyclo[3.2.1]octane-8-carboxamide 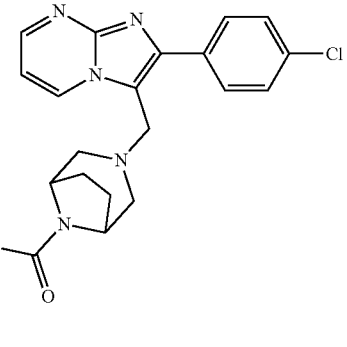 24.8 mg (98% purity, 49% of theory) | $R_t$ = 1.13 min; m/z = 491 $[M + H]^+$ |
| 94 | 3-{[2-(4-chlorophenyl)imidazo[1,2-a]pyrimidin-3-yl]methyl}-N-(2,3-dichlorophenyl)-3,8-diazabicyclo[3.2.1]octane-8-carboxamide 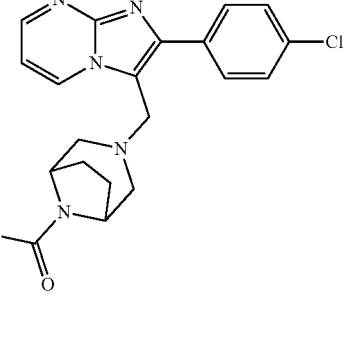 20.8 mg (99% purity, 38% of theory) | $R_t$ = 1.24 min; m/z = 541 $[M + H]^+$ |
| 95 | 3-{[2-(4-chlorophenyl)imidazo[1,2-a]pyrimidin-3-yl]methyl}-N-(2-ethylphenyl)-3,8-diazabicyclo[3.2.1]octane-8-carboxamide 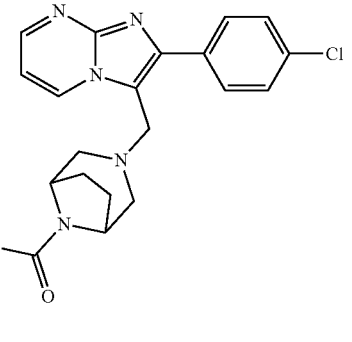 6.0 mg (100% purity, 12% of theory) | $R_t$ = 1.17 min; m/z = 501 $[M + H]^+$ |

| Example | Name/structure (yield, purity) | LC-MS (Method 7) |
|---|---|---|
| 96 | N-(2-chlorophenyl)-3-{[2-(4-chlorophenyl)imidazo[1,2-a]pyrimidin-3-yl]methyl}-3,8-diazabicyclo[3.2.1]octane-8-carboxamide<br/>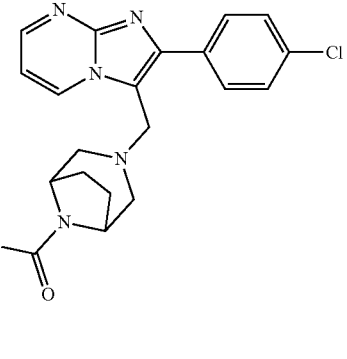<br/>600 µg (100% purity, 1% of theory) | $R_t$ = 1.17 min; m/z = 507 [M + H]$^+$ |
| 97 | 3-{[2-(4-chlorophenyl)imidazo[1,2-a]pyrimidin-3-yl]methyl}-N-[2-chloro-5-(trifluoromethyl)phenyl]-3,8-diazabicyclo[3.2.1]octane-8-carboxamide<br/>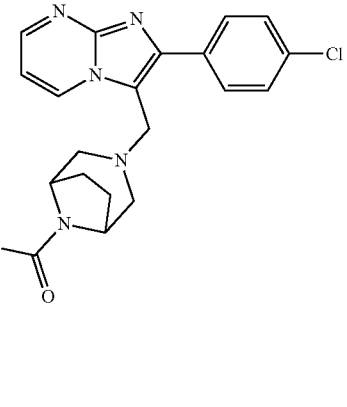<br/>26.9 mg (99% purity, 47% of theory) | $R_t$ = 1.29 min; m/z = 575 [M + H]$^+$ |
| 98 | 3-{[2-(4-chlorophenyl)imidazo[1,2-a]pyrimidin-3-yl]methyl}-N-(2-ethyl-6-methylphenyl)-3,8-diazabicyclo[3.2.1]octane-8-carboxamide<br/>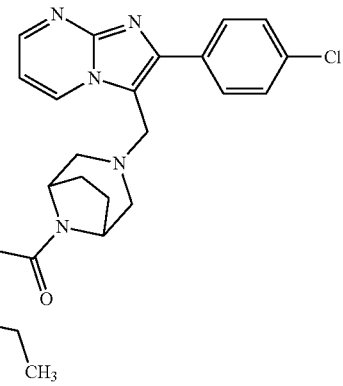<br/>7.8 mg (97% purity, 15% of theory) | $R_t$ = 1.18 min; m/z = 515 [M + H]$^+$ |

| Example | Name/structure (yield, purity) | LC-MS (Method 7) |
|---|---|---|
| 99 | 3-{[2-(4-chlorophenyl)imidazo[1,2-a]pyrimidin-3-yl]methyl}-N-(2,5-dimethylphenyl)-3,8-diazabicyclo[3.2.1]octane-8-carboxamide<br><br>16.1 mg (94% purity, 30% of theory) | $R_t$ = 1.17 min; m/z = 501 [M + H]$^+$ |
| 100 | 3-{[2-(4-Chlorophenyl)imidazo[1,2-a]pyrimidin-3-yl]methyl}-N-cyclohexyl-3,8-diazabicyclo[3.2.1]octane-8-carboxamide<br><br>27.3 mg (100% purity, 57% of theory) | $R_t$ = 1.14 min; m/z = 479 [M + H]$^+$ |
| 101 | 3-{[2-(4-Chlorophenyl)imidazo[1,2-a]pyrimidin-3-yl]methyl}-N-isobutyl-3,8-diazabicyclo[3.2.1]octane-8-carboxamide<br><br>5.1 mg (100% purity, 11% of theory) | $R_t$ = 1.09 min; m/z = 453 [M + H]$^+$ |

| Example | Name/structure (yield, purity) | LC-MS (Method 7) |
|---|---|---|
| 102 | 3-{[2-(4-chlorophenyl)imidazo[1,2-a]pyrimidin-3-yl]methyl}-N-(3,4-dimethoxyphenyl)-3,8-diazabicyclo[3.2.1]octane-8-carboxamide 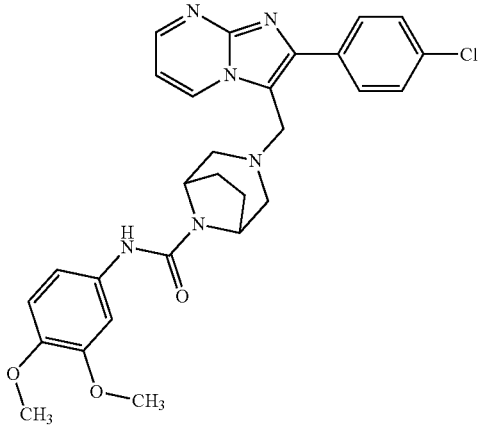 14.6 mg (90% purity, 25% of theory) | $R_t$ = 1.07 min; m/z = 533 [M + H]$^+$ |
| 103 | 3-{[2-(4-chlorophenyl)imidazo[1,2-a]pyrimidin-3-yl]methyl}-N-{4-[(trifluoromethyl)sulfanyl]phenyl}-3,8-diazabicyclo[3.2.1]octane-8-carboxamide 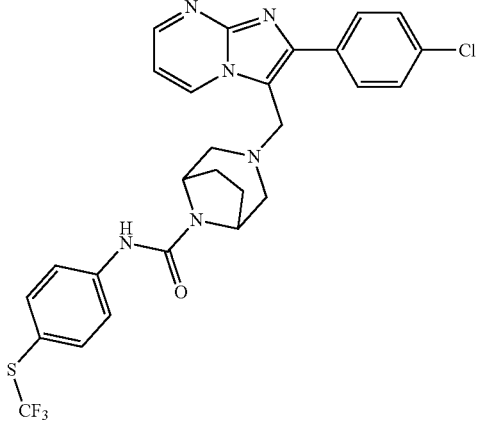 2.0 mg (100% purity, 3% of theory) | $R_t$ = 1.27 min; m/z = 573 [M + H]$^+$ |

| Example | Name/structure (yield, purity) | LC-MS (Method 7) |
|---|---|---|
| 104 | 3-{[2-(4-chlorophenyl)imidazo[1,2-a]pyrimidin-3-yl]methyl}-N-(3-fluorophenyl)-3,8-diazabicyclo[3.2.1]octane-8-carboxamide<br><br>26.2 mg (97% purity, 52% of theory) | $R_t$ = 1.16 min; m/z = 491 [M + H]$^+$ |
| 105 | 3-{[2-(4-chlorophenyl)imidazo[1,2-a]pyrimidin-3-yl]methyl}-N-(2,6-difluorophenyl)-3,8-diazabicyclo[3.2.1]octane-8-carboxamide<br><br>12.8 mg (100% purity, 25% of theory) | $R_t$ = 1.10 min; m/z = 509 [M + H]$^+$ |
| 106 | 3-{[2-(4-chlorophenyl)imidazo[1,2-a]pyrimidin-3-yl]methyl}-N-[4-chloro-2-(trifluoromethyl)phenyl]-3,8-diazabicyclo[3.2.1]octane-8-carboxamide<br><br>20.6 mg (92% purity, 33% of theory) | $R_t$ = 1.25 min; m/z = 575 [M + H]$^+$ |

| Example | Name/structure (yield, purity) | LC-MS (Method 7) |
|---|---|---|
| 107 | 3-{[2-(4-chlorophenyl)imidazo[1,2-a]pyrimidin-3-yl]methyl}-N-(2-methylbenzyl)-3,8-diazabicyclo[3.2.1]octane-8-carboxamide 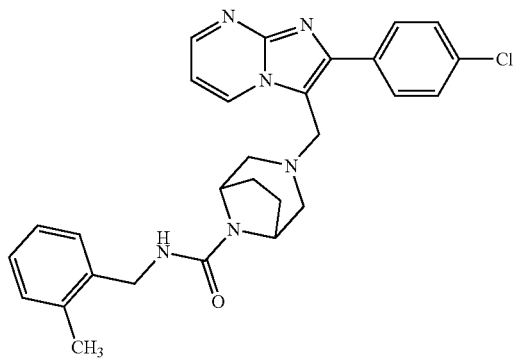 20.1 mg (100% purity, 40% of theory) | $R_t$ = 1.16 min; m/z = 501 [M + H]$^+$ |
| 108 | 3-{[2-(4-chlorophenyl)imidazo[1,2-a]pyrimidin-3-yl]methyl}-N-methyl-N-phenyl-3,8-diazabicyclo[3.2.1]octane-8-carboxamide 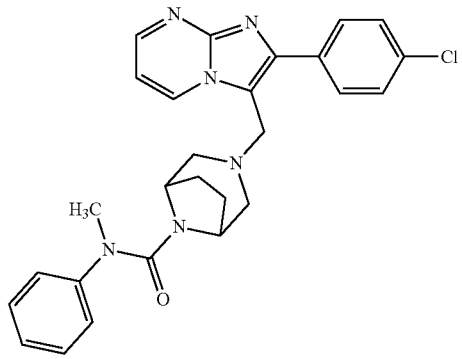 16.6 mg (100% purity, 34% of theory) | $R_t$ = 1.22 min; m/z = 487 [M + H]$^+$ |
| 109 | 3-{[2-(4-chlorophenyl)imidazo[1,2-a]pyrimidin-3-yl]methyl}-N,N-diethyl-3,8-diazabicyclo[3.2.1]octane-8-carboxamide 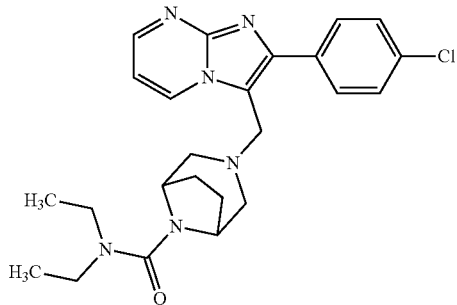 21.3 mg (100% purity, 47% of theory) | $R_t$ = 1.16 min; m/z = 453 [M + H]$^+$ |

| Example | Name/structure (yield, purity) | LC-MS (Method 7) |
| --- | --- | --- |
| 110 | 3-{[2-(4-chlorophenyl)imidazo[1,2-a]pyrimidin-3-yl]methyl}-3,8-diazabicyclo[3.2.1]oct-8-yl)(morpholin-4-yl)methanone<br><br>2.7 mg (100% purity, 6% of theory) | $R_t$ = 1.03 min; m/z = 467 [M + H]$^+$ |
| 111 | 3-{[2-(4-chlorophenyl)imidazo[1,2-a]pyrimidin-3-yl]methyl}-N,N-diisopropyl-3,8-diazabicyclo[3.2.1]octane-8-carboxamide<br><br>2.7 mg (100% purity, 6% of theory) | $R_t$ = 1.23 min; m/z = 481 [M + H]$^+$ |
| 112 | 3-{[2-(4-chlorophenyl)imidazo[1,2-a]pyrimidin-3-yl]methyl}-N-cyclohexyl-N-ethyl-3,8-diazabicyclo[3.2.1]octane-8-carboxamide<br><br>16.8 mg (100% purity, 33% of theory) | $R_t$ = 1.30 min; m/z = 507 [M + H]$^+$ |

| Example | Name/structure (yield, purity) | LC-MS (Method 7) |
|---|---|---|
| 113 | 3-{[2-(4-chlorophenyl)imidazo[1,2-a]pyrimidin-3-yl]methyl}-3,8-diazabicyclo[3.2.1]oct-8-yl)(pyrrolidin-1-yl)methanone<br>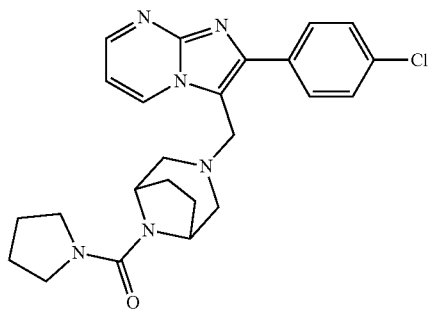<br>22.8 mg (98% purity, 50% of theory) | $R_t$ = 1.10 min; m/z = 451 [M + H]$^+$ |
| 114 | 3-{[2-(4-chlorophenyl)imidazo[1,2-a]pyrimidin-3-yl]methyl}-N-ethyl-N-phenyl-3,8-diazabicyclo[3.2.1]octane-8-carboxamide<br>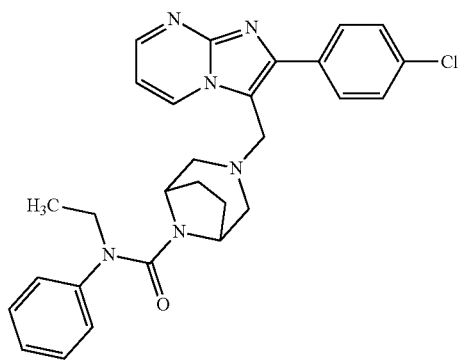<br>14.9 mg (100% purity, 30% of theory) | $R_t$ = 1.25 min; m/z = 501 [M + H]$^+$ |
| 115 | 3-{[2-(4-chlorophenyl)imidazo[1,2-a]pyrimidin-3-yl]methyl}-N-isopropyl-N-methyl-3,8-diazabicyclo[3.2.1]octane-8-carboxamide<br>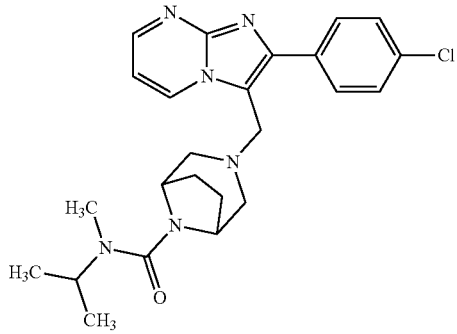<br>4.3 mg (100% purity, 9% of theory) | $R_t$ = 1.14 min; m/z = 453 [M + H]$^+$ |

| Example | Name/structure (yield, purity) | LC-MS (Method 7) |
|---|---|---|
| 116 | 3-{[2-(4-chlorophenyl)imidazo[1,2-a]pyrimidin-3-yl]methyl}-3,8-diazabicyclo[3.2.1]oct-8-yl)(piperidin-1-yl)methanone<br><br>3.0 mg (100% purity, 6% of theory) | $R_t$ = 1.16 min; m/z = 465 [M + H]$^+$ |
| 117 | 3-{[2-(4-chlorophenyl)imidazo[1,2-a]pyrimidin-3-yl]methyl}-N-ethyl-N-(4-methylphenyl)-3,8-diazabicyclo[3.2.1]octane-8-carboxamide<br><br>5.2 mg (98% purity, 10% of theory) | $R_t$ = 1.30 min; m/z = 515 [M + H]$^+$ |
| 118 | N-(4-chlorophenyl)-3-{[2-(4-chlorophenyl)imidazo[1,2-a]pyrimidin-3-yl]methyl}-N-isopropyl-3,8-diazabicyclo[3.2.1]octane-8-carboxamide<br><br>3.4 mg (100% purity, 6% of theory) | $R_t$ = 1.33 min; m/z = 549 [M + H]$^+$ |

-continued

| Example | Name/structure (yield, purity) | LC-MS (Method 7) |
|---|---|---|
| 119 | 3-{[2-(4-chlorophenyl)imidazo[1,2-a]pyrimidin-3-yl]methyl}-N,N-dimethyl-3,8-diazabicyclo[3.2.1]octane-8-carboxamide<br><br>6.6 mg (100% purity, 16% of theory) | $R_t$ = 1.05 min; m/z = 425 [M + H]$^+$ |
| 120 | 3-{[2-(4-chlorophenyl)imidazo[1,2-a]pyrimidin-3-yl]methyl}-N-(4-ethoxyphenyl)-N-methyl-3,8-diazabicyclo[3.2.1]octane-8-carboxamide<br><br>35.4 mg (100% purity, 67% of theory) | $R_t$ = 1.26 min; m/z = 531 [M + H]$^+$ |
| 121 | 3-{[2-(4-chlorophenyl)imidazo[1,2-a]pyrimidin-3-yl]methyl}-N-(3-methoxybenzyl)-N-methyl-3,8-diazabicyclo[3.2.1]octane-8-carboxamide<br><br>35.0 mg (96% purity, 63% of theory) | $R_t$ = 1.23 min; m/z = 531 [M + H]$^+$ |

| Example | Name/structure (yield, purity) | LC-MS (Method 7) |
|---|---|---|
| 122 | (3-{[2-(4-Chlorophenyl)imidazo[1,2-a]pyrimidin-3-yl]methyl}-3,8-diazabicyclo[3.2.1]oct-8-yl)(thiomorpholin-4-yl)methanone<br><br>5.4 mg (100% purity, 11% of theory) | $R_t$ = 1.13 min; m/z = 483 [M + H]$^+$ |
| 123 | methyl 3-{[2-(4-chlorophenyl)imidazo[1,2-a]pyrimidin-3-yl]methyl}-3,8-diazabicyclo[3.2.1]octane-8-carboxylate<br><br>20.7 mg (100% purity, 50% of theory) | $R_t$ = 1.10 min; m/z = 412 [M + H]$^+$ |
| 124 | ethyl 3-{[2-(4-chlorophenyl)imidazo[1,2-a]pyrimidin-3-yl]methyl}-3,8-diazabicyclo[3.2.1]octane-8-carboxylate<br><br>17.8 mg (98% purity, 41% of theory) | $R_t$ = 1.15 min; m/z = 426 [M + H]$^+$ |

| Example | Name/structure (yield, purity) | LC-MS (Method 7) |
|---|---|---|
| 125 | cyclopentyl 3-{[2-(4-chlorophenyl)imidazo[1,2-a]pyrimidin-3-yl]methyl}-3,8-diazabicyclo[3.2.1]octane-8-carboxylate 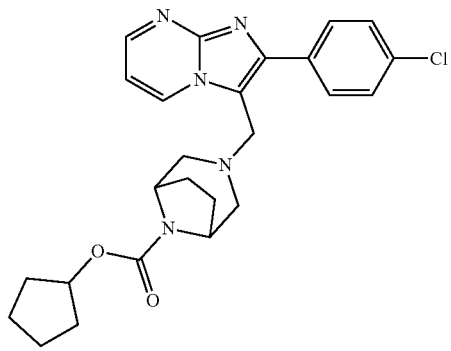 19.7 mg (100% purity, 42% of theory) | $R_t$ = 1.26 min; m/z = 466 [M + H]$^+$ |
| 126 | propyl 3-{[2-(4-chlorophenyl)imidazo[1,2-a]pyrimidin-3-yl]methyl}-3,8-diazabicyclo[3.2.1]octane-8-carboxylate 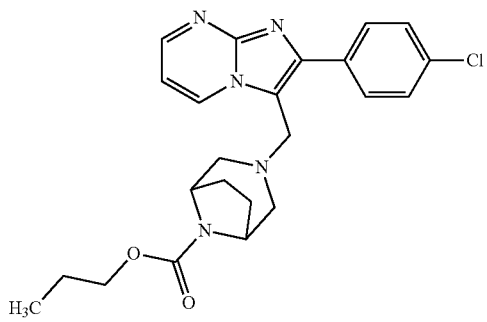 22.5 mg (98% purity, 50% of theory) | $R_t$ = 1.21 min; m/z = 440 [M + H]$^+$ |
| 127 | cyclohexylmethyl 3-{[2-(4-chlorophenyl)imidazo[1,2-a]pyrimidin-3-yl]methyl}-3,8-diazabicyclo[3.2.1]octane-8-carboxylate 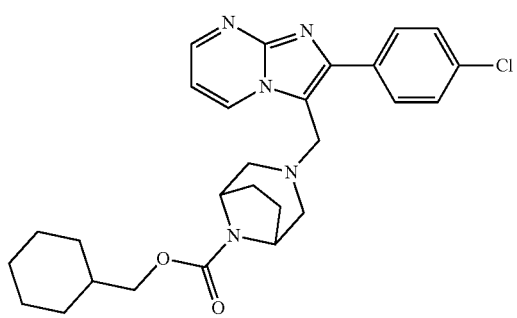 11.7 mg (92% purity, 22% of theory) | $R_t$ = 1.35 min; m/z = 494 [M + H]$^+$ |

| Example | Name/structure (yield, purity) | LC-MS (Method 7) |
|---|---|---|
| 128 | cyclohexyl 3-{[2-(4-chlorophenyl)imidazo[1,2-a]pyrimidin-3-yl]methyl}-3,8-diazabicyclo[3.2.1]octane-8-carboxylate<br>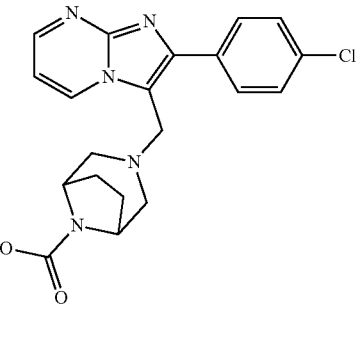<br>4.0 mg (91% purity, 8% of theory) | $R_t$ = 1.30 min; m/z = 480 [M + H]$^+$ |
| 129 | 2,2-dimethylpropyl 3-{[2-(4-chlorophenyl)imidazo[1,2-a]pyrimidin-3-yl]methyl}-3,8-diazabicyclo[3.2.1]octane-8-carboxylate<br>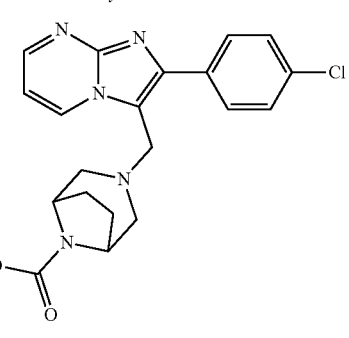<br>10.9 mg (96% purity, 22% of theory) | $R_t$ = 1.29 min; m/z = 468 [M + H]$^+$ |

Example 130 tert-Butyl 3-{[2-(4-isopropylphenyl)imidazo[1,2-a]pyrimidin-3-yl]methyl}-3,8-diazabicyclo[3.2.1]octane-8-carboxylate

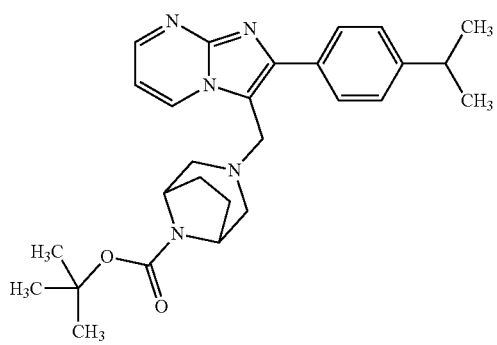 [SMILES: CC(C)c1ccc(-c2nc3ncccn3c2CN2CC3CCC(C2)N3C(=O)OC(C)(C)C)cc1]

Under argon and at room temperature, 2-(4-isopropylphenyl)imidazo[1,2-a]pyrimidine-3-carbaldehyde (700 mg, 2.64 mmol) was dissolved in 14 ml of THF, and tert-butyl 3,8-diazabicyclo[3.2.1]octane-8-carboxylate (672 mg, 3.17 mmol) was added. Sodium triacetoxyborohydride (839 mg, 3.96 mmol) was then added a little at a time, and the reaction solution was stirred at room temperature overnight. Then water was gradually and carefully added dropwise (caution: evolution of gas), and subsequently ethyl acetate was added. The resulting organic phase was removed and the aqueous phase was extracted twice with ethyl acetate. The combined organic phases were washed with saturated sodium chloride solution, dried over magnesium sulfate, filtered and concentrated to dryness under reduced pressure on a rotary evaporator. The residue obtained was purified by column chromatography (Biotage Isolera, Biotage SNAP-KP-NH column; mobile phase: cyclohexane/ethyl acetate gradient). This gave 896 mg (1.94 mmol, 74% of theory) of the target compound.

LC-MS (Method 2): $R_t$=2.14 min; m/z=462 (M+H)$^+$.

$^1$H-NMR (400 MHz, DMSO-d$_6$): δ [ppm]=1.25 (d, 6H), 1.39 (s, 9H), 1.65 (br. s, 4H), 2.26 (br. d, 2H), 2.47-2.60 (m, 2H, partially obscured by DMSO signal), 2.95 (quin, 1H), 3.98 (s, 2H), 4.02 (br. s, 2H), 7.12 (dd, 1H), 7.37 (d, 2H), 7.83 (d, 2H), 8.56 (dd, 1H), 8.99 (dd, 1H).

Example 131

(5-Cyclopropyl-1,3-oxazol-4-yl)(3-{[2-(4-isopropylphenyl)imidazo[1,2-a]pyrimidin-3-yl]methyl}-3,8-diazabicyclo[3.2.1]oct-8-yl)methanone

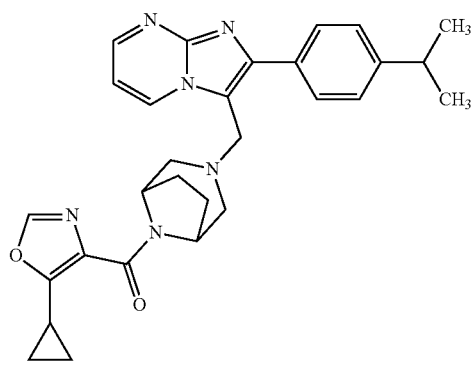 [SMILES: CC(C)c1ccc(-c2nc3ncccn3c2CN2CC3CCC(C2)N3C(=O)c2ncoc2C2CC2)cc1]

Example 132 tert-Butyl 3-{[2-(4-cyclopropylphenyl)imidazo[1,2-a]pyrimidin-3-yl]methyl}-3,8-diazabicyclo[3.2.1]octane-8-carboxylate

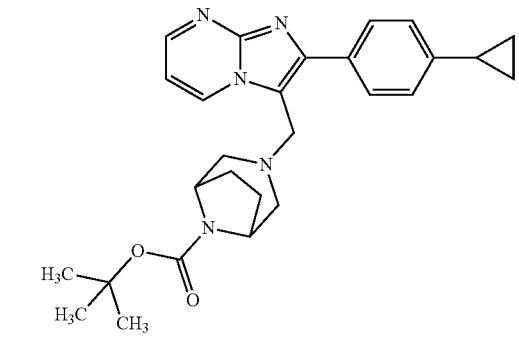 [SMILES: CC(C)(C)OC(=O)N1C2CCC1CN(Cc1c(-c3ccc(C4CC4)cc3)nc3ncccn13)C2]

5-Cyclopropyl-1,3-oxazole-4-carboxylic acid (39 mg, 0.26 mmol) was dissolved in 1.5 ml of DMF, 2-(7-aza-1H-benzotriazol-1-yl)-1,1,3,3-tetramethyluronium hexafluorophosphate (HATU) (121 mg, 0.32 mmol) was added and the mixture was stirred at room temperature for 30 min. 3-(3,8-Diazabicyclo[3.2.1]oct-3-ylmethyl)-2-(4-isopropylphenyl)imidazo[1,2-a]pyrimidine dihydrochloride (100 mg) and N,N-diisopropylethylamine (190 µl, 1.06 mmol) were then added and the mixture was stirred at room temperature overnight. Thereafter, the reaction mixture was separated directly into its components via preparative HPLC (Method 9). 65 mg (0.13 mmol, 61% of theory) of the title compound were obtained.

LC-MS (Method 2): $R_t$=1.81 min; MS (ESIpos): m/z=497 [M+H]$^+$.

$^1$H-NMR (400 MHz, DMSO-d$_6$): δ [ppm]=0.85-0.99 (m, 2H), 1.01-1.13 (m, 2H), 1.25 (d, 6H), 1.63-1.85 (m, 4H), 2.35-2.45 (m, 2H), 2.60-2.74 (m, 3H), 2.88-3.01 (m, 1H), 4.03 (s, 2H), 4.53-4.64 (m, 1H), 5.12 (br. s, 1H), 7.12 (dd, 1H), 7.37 (d, 2H), 7.85 (d, 2H), 8.17 (s, 1H), 8.57 (dd, 1H), 9.03 (dd, 1H).

Under argon and at room temperature, 1090 mg (2.19 mmol) of tert-butyl 3-{[2-(4-bromophenyl)imidazo[1,2-a]pyrimidin-3-yl]methyl}-3,8-diazabicyclo[3.2.1]octane-8-carboxylate were initially charged in 15 ml of toluene and 3 ml of water in a 30 ml microwave vessel, and cyclopropylboronic acid (376 mg, 4.37 mmol), potassium phosphate (1625 mg, 7.65 mmol), palladium(II) acetate (49 mg, 0.22 mmol) and tricyclohexylphosphine (123 mg, 0.44 mmol) were then added. The microwave vessel was then closed and the mixture was heated to 120° C. and stirred at this temperature overnight. After cooling to room temperature, the reaction mixture was filtered through kieselguhr and the residue was washed a little at a time with ethyl acetate. More ethyl acetate and water were added to the filtrate obtained, and the phases were separated. The organic phase was washed with saturated sodium chloride solution, dried over magnesium sulfate and concentrated to dryness. The residue was then stirred with diethyl ether. After filtration, the solid obtained was dried under high vacuum overnight. This gave 667 mg (1.36 mmol, 62% of theory) of the target compound.

LC-MS (Method 2): $R_t$=2.00 min; m/z=460 (M+H)$^+$.

$^1$H-NMR (400 MHz, DMSO-d$_6$): δ [ppm]=0.69-0.77 (m, 2H), 0.95-1.03 (m, 2H), 1.39 (s, 9H), 1.65 (br. s, 4H), 1.93-2.03 (m, 1H), 2.24 (br. d, 2H), 2.45-2.61 (m, 2H, partially obscured by DMSO signal), 3.97 (s, 2H), 4.02 (br. s, 2H), 7.11 (dd, 1H), 7.20 (d, 2H), 7.78 (d, 2H), 8.55 (dd, 1H), 8.99 (dd, 1H).

Analogously to Examples 13-29, the following compounds were prepared from the starting materials specified in each case:

| Example | Name/Structure/Starting materials | Analytical data |
|---|---|---|
| 133 | (3-{[2-(4-cyclopropylphenyl)imidazo[1,2-a]pyrimidin-3-yl]methyl}-3,8-diazabicyclo[3.2.1]octan-8-yl)(2-fluorophenyl)methanone<br><br>from 2-(4-cyclopropylphenyl)-3-(3,8-diazabicyclo[3.2.1]octan-3-ylmethyl)imidazo[1,2-a]pyrimidine dihydrochloride and 2-fluorobenzoic acid | $^1$H-NMR (400 MHz, DMSO-d$_6$): δ [ppm] = 0.70-0.77 (m, 2H), 0.95-1.02 (m, 2H), 1.65-1.79 (m, 4H), 1.93-2.02 (m, 1H), 2.24 (br. d, 1H), 2.41 (br. d, 1H), 2.56 (dd, 1H), 2.68 (dd, 1H), 3.66 (br. s, 1H), 4.03 (s, 2H), 4.59 (br. s, 1H), 7.12 (dd, 1H), 7.20 (d, 2H), 7.25-7.32 (br. s, 1H), 7.41-7.53 (m, 2H), 7.78 (d, 2H), 8.55 (dd, 1H), 9.00 (dd, 1H).<br>LC-MS (Method 1):<br>R$_t$ = 0.87 min; m/z = 482 (M + H)$^+$. |
| 134 | cyclopentyl(3-{[2-(4-cyclopropylphenyl)imidazo[1,2-a]pyrimidin-3-yl]methyl}-3,8-diazabicyclo[3.2.1]octan-8-yl)methanone<br><br>from 2-(4-cyclopropylphenyl)-3-(3,8-diazabicyclo[3.2.1]octan-3-ylmethyl)imidazo[1,2-a]pyrimidine dihydrochloride and cyclopentanecarboxylic acid | $^1$H-NMR (400 MHz, DMSO-d$_6$): δ [ppm] = 0.68-0.79 (m, 2H), 0.94-1.03 (m, 2H), 1.44-1.68 (m, 7H), 1.68-1.78 (m, 5H), 1.97 (tt, 1H), 2.18-2.30 (m, 2H), 2.53-2.65 (m, 2H), 2.80-2.90 (m, 1H), 3.94-4.03 (m, 2H), 4.28 (br. s, 1H), 4.41 (br. d, 1H), 7.11 (dd, 1H), 7.20 (d, 2H), 7.79 (d, 2H), 8.56 (dd, 1H), 9.01 (dd, 1H).<br>LC-MS (Method 1):<br>R$_t$ = 0.90 min; m/z = 456 (M + H)$^+$. |
| 135 | (3-{[2-(4-cyclopropylphenyl)imidazo[1,2-a]pyrimidin-3-yl]methyl}-3,8-diazabicyclo[3.2.1]octan-8-yl)(3-fluoro-6-methoxypyridin-2-yl)methanone<br><br>from 2-(4-cyclopropylphenyl)-3-(3,8-diazabicyclo[3.2.1]octan-3-ylmethyl)imidazo[1,2-a]pyrimidine dihydrochloride and 3-fluoro-6-methoxypyridine-2-carboxylic acid | $^1$H-NMR (400 MHz, DMSO-d$_6$): δ [ppm] = 0.69-0.78 (m, 2H), 0.95-1.04 (m, 2H), 1.63-1.84 (m, 4H), 1.93-2.02 (m, 1H), 2.43 (br. t, 2H), 2.52-2.57 (m, 1H), 2.76 (dd, 1H), 3.75 (s, 3H), 3.91 (br. s, 1H), 3.99-4.09 (m, 2H), 4.61 (br. s, 1H), 6.95 (dd, 1H), 7.12 (dd, 1H), 7.20 (d, 2H), 7.73-7.81 (m, 3H), 8.56 (dd, 1H), 9.01 (dd, 1H).<br>LC-MS (Method 1):<br>R$_t$ = 0.86 min; m/z = 513 (M + H)$^+$. |

| Example | Name/Structure/Starting materials | Analytical data |
|---|---|---|
| 136 | (3-chloro-6-methoxypyridin-2-yl)(3-{[2-(4-cyclopropylphenyl)imidazo[1,2-a]pyrimidin-3-yl]methyl}-3,8-diazabicyclo[3.2.1]octan-8-yl)methanone<br><br>from 2-(4-cyclopropylphenyl)-3-(3,8-diazabicyclo[3.2.1]octan-3-ylmethyl)imidazo[1,2-a]pyrimidine dihydrochloride and 3-chloro-6-methoxypyridine-2-carboxylic acid | $^1$H-NMR (400 MHz, DMSO-d$_6$): δ [ppm] = 0.68-0.78 (m, 2H), 0.94-1.03 (m, 2H), 1.62-1.83 (m, 4H), 1.93-2.02 (m, 1H), 2.33-2.44 (m, 2H), 2.45-2.56 (m, 1H, partially obscured by DMSO signal), 2.75 (dd, 1H), 3.62 (br. s, 1H), 3.78 (s, 3H), 3.99-4.10 (m, 2H), 4.60 (br. s, 1H), 6.92 (d, 1H), 7.12 (dd, 1H), 7.19 (d, 2H), 7.77 (d, 2H), 7.87 (d, 1H), 8.56 (dd, 1H), 9.00 (dd, 1H).<br>LC-MS (Method 1):<br>R$_t$ = 0.90 min; m/z = 529/531 (M + H)$^+$. |
| 137 | (3-{[2-(4-cyclopropylphenyl)imidazo[1,2-a]pyrimidin-3-yl]methyl}-3,8-diazabicyclo[3.2.1]octan-8-yl)(6-methoxypyridin-2-yl)methanone<br><br>from 2-(4-cyclopropylphenyl)-3-(3,8-diazabicyclo[3.2.1]octan-3-ylmethyl)imidazo[1,2-a]pyrimidine dihydrochloride and 6-methoxypyridine-2-carboxylic acid | $^1$H-NMR (400 MHz, DMSO-d$_6$): δ [ppm] = 0.65-0.79 (m, 2H), 0.94-1.04 (m, 2H), 1.65-1.82 (m, 4H), 1.93-2.01 (m, 1H), 2.43 (br. d, 1H), 2.55-2.64 (m, 2H), 2.73 (dd, 1H), 3.77 (s, 3H), 3.98-4.09 (m, 2H), 4.63 (br. s, 1H), 4.69 (br. s, 1H), 6.92 (dd, 1H), 7.12 (dd, 1H), 7.20 (d, 2H), 7.35 (dd, 1H), 7.75-7.85 (m, 3H), 8.56 (dd, 1H), 9.02 (dd, 1H).<br>LC-MS (Method 1):<br>R$_t$ = 0.87 min; m/z = 495 (M + H)$^+$. |
| 138 | (3-{[2-(4-cyclopropylphenyl)imidazo[1,2-a]pyrimidin-3-yl]methyl}-3,8-diazabicyclo[3.2.1]octan-8-yl)[6-(difluoromethoxy)pyridin-2-yl]methanone<br><br>from 2-(4-cyclopropylphenyl)-3-(3,8-diazabicyclo[3.2.1]octan-3-ylmethyl)imidazo[1,2-a]pyrimidine dihydrochloride and 6-(difluoromethoxy)pyridine-2-carboxylic acid | $^1$H-NMR (400 MHz, DMSO-d$_6$): δ [ppm] = 0.68-0.76 (m, 2H), 0.94-1.02 (m, 2H), 1.67-1.83 (m, 4H), 1.92-2.01 (m, 1H), 2.42 (br. d, 1H), 2.53-2.59 (m, 1H), 2.60-2.66 (m, 1H), 2.72 (dd, 1H), 4.04 (s, 2H), 4.57 (br. s, 1H), 4.64 (br. s, 1H), 7.11 (dd, 1H), 7.16-7.24 (m, 3H), 7.44 (s, 0.25H), 7.56-7.64 (m, 1.5H), 7.73 (s, 0.25H), 7.79 (d, 2H), 8.05 (t, 1H), 8.57 (dd, 1H), 9.03 (dd, 1H).<br>LC-MS (Method 1):<br>R$_t$ = 0.91 min; m/z = 531 (M + H)$^+$. |

| Example | Name/Structure/Starting materials | Analytical data |
|---|---|---|
| 139 | (5-cyclopropyl-1,3-oxazol-4-yl)(3-{[2-(4-cyclopropylphenyl)imidazo[1,2-a]pyrimidin-3-yl]methyl}-3,8-diazabicyclo[3.2.1]octan-8-yl)methanone<br>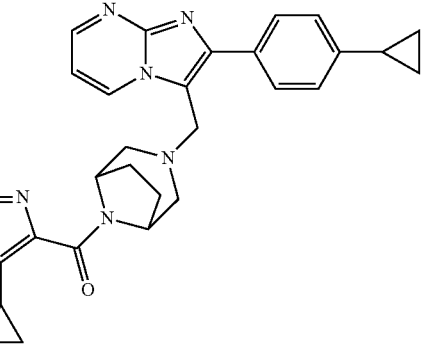<br>from 2-(4-cyclopropylphenyl)-3-(3,8-diazabicyclo[3.2.1]octan-3-ylmethyl)imidazo[1,2-a]pyrimidine dihydrochloride and 5-cyclopropyl-1,3-oxazole-4-carboxylic acid | $^1$H-NMR (400 MHz, DMSO-$d_6$): δ [ppm] = 0.69-0.77 (m, 2H), 0.87-1.01 (m, 4H), 1.02-1.12 (m, 2H), 1.61-1.85 (m, 4H), 1.92-2.01 (m, 1H), 2.39 (br. t, 2H), 2.60-2.74 (m, 3H), 4.01 (s, 2H), 4.59 (br. d, 1H), 5.11 (br. s, 1H), 7.12 (dd, 1H), 7.20 (d, 2H), 7.80 (d, 2H), 8.17 (s, 1H), 8.56 (dd, 1H), 9.02 (dd, 1H). LC-MS (Method 1): $R_t$ = 0.87 min; m/z = 495 (M + H)$^+$. |

B. ASSESSMENT OF PHARMACOLOGICAL EFFICACY

The pharmacological activity of the compounds of the invention can be demonstrated by in vitro and in vivo studies as known to the person skilled in the art. The application examples which follow describe the biological action of the compounds of the invention, without restricting the invention to these examples.

B-1. In Vitro Electrophysiological Analysis of the Human TASK-1 and TASK-3 Channels Via Two-Electrode Voltage Clamp Technique in *Xenopus laevis* Oocytes

*Xenopus laevis* oocytes were selected as described elsewhere by way of illustration [Decher et al., *FEBS Lett.* 492, 84-89 (2001)]. Subsequently, the oocytes were injected with 0.5-5 ng of a cRNA solution coding for TASK-1 or TASK-3. For the electrophysiological analysis of the channel proteins expressed in the oocytes, the two-electrode voltage clamp technique [Stühmer, *Methods Enzymol.* 207, 319-339 (1992)] was used. The measurements were conducted as described [Decher et al., *FEBS Lett.* 492, 84-89 (2001)] at room temperature (21-22° C.) using a Turbo TEC 10CD amplifier (NPI), recorded at 2 kHz and filtered with 0.4 kHz. Substance administration was performed using a gravitation-driven perfusion system. Here, the oocyte is located in a measuring chamber and exposed to the solution stream of 10 ml/min. The level in the measuring chamber is monitored and regulated by sucking off the solution using a peristaltic pump.

Table 1 below shows the half-maximum inhibition, determined in this test, of human TASK-1 and TASK-3 channels (IC$_{50}$) by representative working examples of the invention:

TABLE 1

| Example No. | TASK-1 IC$_{50}$ [nM] | TASK-3 IC$_{50}$ [nM] |
|---|---|---|
| 19 | 239.4 ± 2.7 | 774.2 ± 67.1 |
| 21 | 19.2 ± 4.3 | 32.9 ± 6.0 |
| 26 | 31.2 ± 5.8 | 140.0 ± 34.6 |
| 27 | 17.9 ± 2.2 | 367.1 ± 67.6 |

TABLE 1-continued

| Example No. | TASK-1 IC$_{50}$ [nM] | TASK-3 IC$_{50}$ [nM] |
|---|---|---|
| 28 | 20.5 ± 2.7 | 6.6 ± 0.8 |
| 29 | 21.0 ± 4.1 | 42.7 ± 8.4 |
| 41 | 44.4 ± 4.4 | 71.8 ± 15.5 |
| 51 | 21.7 ± 4.6 | 35.9 ± 8.2 |

From the data in Table 1 it is evident that both TASK-1 and TASK-3 are blocked. The results in Table 1 thus confirm the mechanism of action of the compounds according to the invention as dual TASK-1/3 inhibitors.

B-2. Inhibition of Recombinant TASK-1 and TASK-3 In Vitro

The investigations on the inhibition of the recombinant TASK-1 and TASK-3 channels were conducted using stably transfected CHO cells. The compounds according to the invention were tested in this case by application of 40 mM potassium chloride in the presence of a voltage-sensitive dye according to the method described in detail in the following references [Whiteaker et al., Validation of FLIPR membrane potential dye for high-throughput screening of potassium channel modulators, *J. Biomol. Screen.* 6 (5), 305-312 (2001); Molecular Devices FLIPR Application Note: Measuring membrane potential using the FLIPR® membrane potential assay kit on Fluorometric Imaging Plate Reader (FLIPR®) systems, http://www.moleculardevices.com/reagents-supplies/assay-kits/ion-channels/flipr-membrane-potential-assay-kits]. The activity of the test substances was determined as their ability to inhibit a depolarization induced in the recombinant cells by 40 mM potassium chloride. The concentration which can block half of this depolarization is referred to as IC$_{50}$.

Table 2 below lists the IC$_{50}$ values from this assay determined for individual working examples of the invention (some as mean values from multiple independent individual determinations):

TABLE 2

| Example No. | TASK-1 IC$_{50}$ [nM] | TASK-3 IC$_{50}$ [nM] |
|---|---|---|
| 1 | 1700 | 400 |
| 4 | 470 | 97 |
| 5 | 17000 | 1300 |
| 6 | 1400 | 41 |
| 7 | 8600 | 570 |
| 10 | 2200 | 130 |
| 11 | 2500 | 16 |
| 12 | 220 | 13 |
| 13 | 1500 | 33 |
| 14 | 7600 | 170 |
| 15 | 1100 | 19 |
| 16 | 670 | 12 |
| 17 | 1200 | 33 |
| 18 | 910 | 8.6 |
| 19 | 22000 | 59 |
| 20 | 160 | 38 |
| 21 | 140 | 4.2 |
| 22 | 340 | 5.2 |
| 23 | 1600 | 100 |
| 24 | 410 | 102 |
| 25 | 1100 | 71 |
| 26 | 1400 | 16 |
| 27 | 1200 | 10 |
| 28 | 290 | 3.2 |
| 29 | 280 | 1.8 |
| 30 | 3500 | 85 |
| 31 | 7100 | 140 |
| 32 | 370 | 29 |
| 33 | 190 | 130 |
| 34 | 76 | 29 |
| 35 | 6700 | 1500 |
| 36 | 310 | 80 |
| 37 | 1500 | 140 |
| 38 | 9600 | 320 |
| 39 | 1400 | 160 |
| 40 | 5700 | 210 |
| 41 | 1500 | 100 |
| 42 | 1000 | 340 |
| 43 | 1000 | 320 |
| 44 | 1000 | 190 |
| 45 | 1800 | 120 |
| 46 | 7600 | 140 |
| 47 | 2800 | 110 |
| 48 | 400 | 23 |
| 49 | 260 | 12 |
| 50 | 3300 | 430 |
| 51 | 250 | 8.7 |
| 52 | 1300 | 52 |
| 53 | 620 | 19 |
| 54 | 860 | 13 |
| 55 | 2900 | 170 |
| 56 | 5600 | 54 |
| 57 | 6400 | 57 |
| 58 | 1600 | 17 |
| 59 | 3000 | 39 |
| 60 | 670 | 430 |
| 61 | 3000 | 640 |
| 62 | 6900 | 70 |
| 63 | 1700 | 15 |
| 64 | 1100 | 8.4 |
| 65 | 3500 | 670 |
| 66 | 3700 | 20 |
| 67 | 1200 | 17 |
| 68 | 9400 | 87 |
| 69 | 2800 | 22 |
| 70 | 1900 | 20 |
| 71 | 14000 | 110 |
| 72 | 2100 | 29 |
| 73 | 9100 | 81 |
| 74 | 3400 | 61 |
| 75 | 3800 | 51 |
| 76 | 13000 | 56 |
| 77 | 720 | 4.9 |
| 78 | 3800 | 24 |
| 81 | 820 | 21 |
| 82 | 670 | 37 |
| 83 | 250 | 14 |
| 84 | 93 | 4.6 |
| 85 | 30000 | 1000 |
| 86 | 7700 | 430 |
| 89 | 30000 | 850 |
| 91 | 20000 | 410 |
| 92 | 15000 | 270 |
| 93 | 12000 | 260 |
| 94 | 30000 | 160 |
| 95 | 3000 | 41 |
| 97 | 31000 | 450 |
| 98 | 9000 | 160 |
| 99 | 30000 | 750 |
| 100 | 19000 | 630 |
| 101 | 19000 | 510 |
| 103 | 30000 | 690 |
| 104 | 19000 | 460 |
| 106 | 30000 | 89 |
| 107 | 30000 | 750 |
| 108 | 7000 | 90 |
| 109 | 24 | 1.5 |
| 110 | 13000 | 230 |
| 111 | 6300 | 290 |
| 112 | 15000 | 130 |
| 113 | 1100 | 62 |
| 114 | 6700 | 140 |
| 115 | 7400 | 330 |
| 116 | 2700 | 65 |
| 118 | 19000 | 220 |
| 119 | 5300 | 210 |
| 120 | 15000 | 230 |
| 121 | 12000 | 120 |
| 122 | 5000 | 120 |
| 123 | 14000 | 230 |
| 124 | 790 | 17 |
| 125 | 230 | 27 |
| 126 | 280 | 14 |
| 128 | 2000 | 110 |
| 130 | 1700 | 210 |
| 131 | 3500 | 410 |
| 132 | 1700 | 410 |
| 133 | 1600 | 180 |
| 134 | 770 | 97 |
| 135 | 420 | 34 |
| 136 | 320 | 41 |
| 137 | 1100 | 180 |
| 138 | 3200 | 290 |
| 139 | 4500 | 470 |

From the data in Table 2 it is evident that both TASK-1 and in particular TASK-3 are blocked. The results in Table 2 thus confirm the mechanism of action of the compounds according to the invention as dual TASK-1/3 inhibitors.

B-3. Animal Model of Obstructive Sleep Apnoea in the Pig

Using negative pressure, it is possible to induce collapse and thus obstruction of the upper respiratory tract in anaesthetized, spontaneously breathing pigs [Wirth et al., *Sleep* 36, 699-708 (2013)].

German Landrace pigs are used for the model. The pigs are anaesthetized and tracheotomized. One cannula each is inserted into the rostral and the caudal part of the trachea. Using a T connector, the rostral cannula is connected on the one hand to a device generating negative pressures and on the other hand to the caudal cannula. Using a T connector, the caudal cannula is connected to the rostral cannula and to a tube which allows spontaneous breathing circumventing the upper respiratory tract. By appropriate closing and opening of the tubes it is thus possible for the pig to change from normal nasal breathing to breathing via the caudal cannula during the time when the upper respiratory tract is isolated and connected to the device for generating negative pressures. The muscle activity of the Musculus genioglossus is recorded by electromyogram (EMG).

At certain points in time, the collapsibility of the upper respiratory tract is tested by having the pig breathe via the caudal cannula and applying negative pressures of −50, −100 and −150 cm water head (cm H$_2$O) to the upper respiratory tract. This causes the upper respiratory tract to collapse, which manifests itself in an interruption of the airflow and a pressure drop in the tube system. This test is conducted prior to the administration of the test substance and at certain intervals after the administration of the test substance. An appropriately effective test substance can prevent this collapse of the respiratory tract in the inspiratory phase.

After changeover from nasal breathing to breathing via the caudal cannula, it is not possible to measure any EMG activity of the Musculus genioglossus in the anaesthetized pig. As a further test, the negative pressure at which EMG activity restarts is then determined. This threshold value is, if a test substance is effective, shifted to more positive values. The test is likewise conducted prior to the administration of the test substance and at certain intervals after the administration of the test substance. Administration of the test substance can be intranasal, intravenous, subcutaneous, intraperitoneal or intragastral.

C. WORKING EXAMPLES OF PHARMACEUTICAL COMPOSITIONS

The compounds of the invention can be converted to pharmaceutical preparations as follows:
Tablet:
Composition:
100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.
Production:
The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.
Suspension for Oral Administration:
Composition:
1000 mg of the compound of the invention, 1000 mg of ethanol (96%), 400 mg of Rhodigel® (xanthan gum from FMC, Pennsylvania, USA) and 99 g of water.

10 ml of oral suspension correspond to a single dose of 100 mg of the compound of the invention.
Production:
The Rhodigel is suspended in ethanol; the compound of the invention is added to the suspension. The water is added while stirring. The mixture is stirred for about 6 h until the swelling of the Rhodigel is complete.
Solution for Oral Administration:
Composition:
500 mg of the compound of the invention, 2.5 g of polysorbate and 97 g of polyethylene glycol 400. 20 g of oral solution correspond to a single dose of 100 mg of the compound of the invention.
Production:
The compound of the invention is suspended in the mixture of polyethylene glycol and polysorbate with stirring. The stirring operation is continued until dissolution of the compound of the invention is complete.
i.v. Solution:
The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.
Solution for Nasal Administration:
The compound of the invention is dissolved in a concentration below the saturation solubility in a physiologically acceptable solvent (e.g. purified water, phosphate buffer, citrate buffer). The solution may contain further additives for isotonization, for preservation, for adjusting the pH, for improvement in the solubility and/or for stabilization.

The invention claimed is:

1. A method for treatment of obstructive sleep apnoeas, comprising administering to a human or animal in need thereof an effective amount of a compound of formula (I)

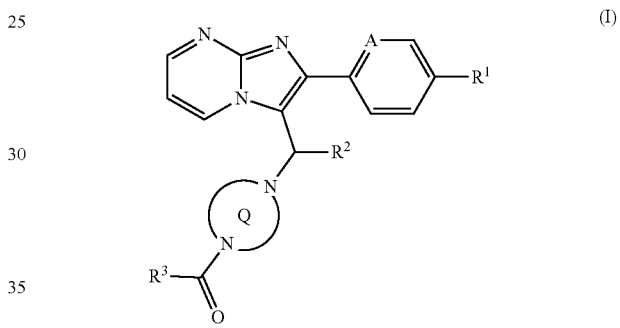

wherein
ring Q is a diazaheterobicyclic system of the formula:

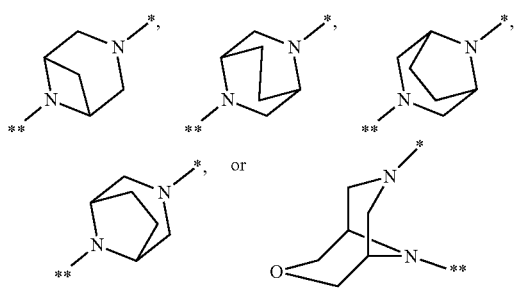

wherein * denotes the bond to the adjacent CHR$^2$ group and ** the bond to the carbonyl group;
A is CH or N;
R$^1$ is halogen, cyano, (C$_1$-C$_4$)-alkyl, cyclopropyl or cyclobutyl,
wherein (C$_1$-C$_4$)-alkyl is optionally up to trisubstituted by fluorine, and cyclopropyl and cyclobutyl are optionally up to disubstituted by fluorine;
R$^2$ is hydrogen or methyl;
and
R$^3$ is (C$_4$-C$_6$)-cycloalkyl wherein a ring CH$_2$ group is optionally replaced by —O—;

or

R³ is a phenyl group of the formula (a), a pyridyl group of the formula (b) or (c) or an azole group of the formula (d), (e) or (f)

(a)
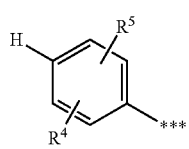

(b)
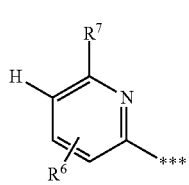

(c)
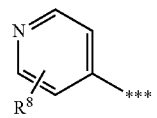

(d)
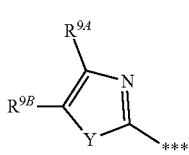

(e)
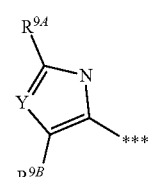

(f)
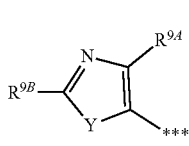

wherein *** marks the bond to the adjacent carbonyl group; and $R^4$ is hydrogen, fluorine, chlorine, bromine or methyl;

$R^5$ is hydrogen, fluorine, chlorine, bromine, cyano, $(C_1-C_3)$-alkyl or $(C_1-C_3)$-alkoxy,
wherein $(C_1-C_3)$-alkyl and $(C_1-C_3)$-alkoxy are optionally up to trisubstituted by fluorine;

$R^6$ is hydrogen, fluorine, chlorine, bromine or methyl;

$R^7$ is hydrogen, $(C_1-C_3)$-alkoxy, cyclobutyloxy, oxetan-3-yloxy, tetrahydrofuran-3-yloxy, tetrahydro-2H-pyran-4-yloxy, mono-$(C_1-C_3)$-alkylamino, di-$(C_1-C_3)$-alkylamino or $(C_1-C_3)$-alkylsulfanyl,
wherein $(C_1-C_3)$-alkoxy may be up to trisubstituted by fluorine;

$R^8$ is hydrogen, fluorine, chlorine, bromine, $(C_1-C_3)$-alkyl or $(C_1-C_3)$-alkoxy, $R^{9A}$ and $R^{9B}$ are identical or different and are independently hydrogen, fluorine, chlorine, bromine, $(C_1-C_3)$-alkyl, cyclopropyl or $(C_1-C_3)$-alkoxy,
wherein $(C_1-C_3)$-alkyl and $(C_1-C_3)$-alkoxy are optionally up to trisubstituted by fluorine;

and
Y is O or S;

or

R³ is an —$OR^{10}$ or —$NR^{11}R^{12}$ group wherein
$R^{10}$ is $(C_1-C_6)$-alkyl, $(C_4-C_6)$-cycloalkyl or $[(C_3-C_6)$-cycloalkyl]methyl;
$R^{11}$ is hydrogen or $(C_1-C_3)$-alkyl;
and
$R^{12}$ is $(C_1-C_6)$-alkyl, $(C_3-C_6)$-cycloalkyl, phenyl or benzyl,
wherein $(C_1-C_6)$-alkyl is optionally up to trisubstituted by fluorine;
and
wherein phenyl and the phenyl group in benzyl are optionally up to trisubstituted by identical or different radicals selected from the group consisting of fluorine, chlorine, methyl, ethyl, trifluoromethyl, methoxy, ethoxy, trifluoromethoxy and (trifluoromethyl) sulfanyl;
or
$R^{11}$ and $R^{12}$ are attached to one another and, together with the nitrogen atom to which they are bonded, form a pyrrolidine, piperidine, morpholine or thiomorpholine ring, or a salt, a solvate, or a solvate of the salt thereof.

2. A method for treatment of obstructive sleep apnoeas, comprising administering to a human or animal in need thereof an effective amount of a pharmaceutical composition comprising a compound of formula (I),

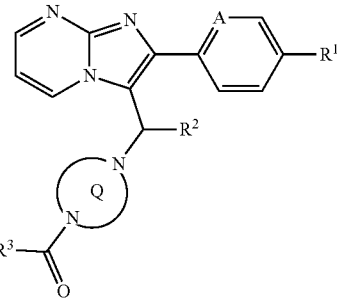
(I)

wherein
the ring Q is a diazaheterobicyclic system of the formula:

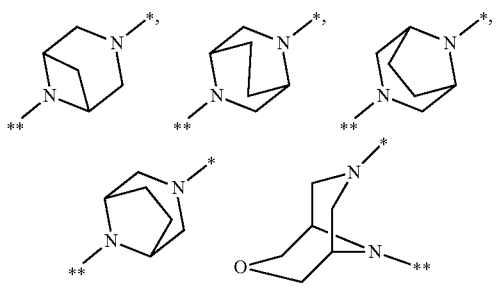

wherein * denotes the bond to the adjacent $CHR^2$ group and ** the bond to the carbonyl group;

A is CH or N;

$R^1$ is halogen, cyano, $(C_1-C_4)$-alkyl, cyclopropyl or cyclobutyl,
wherein $(C_1-C_4)$-alkyl is optionally up to trisubstituted by fluorine, and cyclopropyl and cyclobutyl are optionally up to disubstituted by fluorine;

$R^2$ is hydrogen or methyl;
and
$R^3$ is $(C_4-C_6)$-cycloalkyl wherein a ring $CH_2$ group is optionally replaced by —O—;
or
$R^3$ is a phenyl group of the formula (a), a pyridyl group of the formula (b) or (c) or an azole group of the formula (d), (e) or (f):

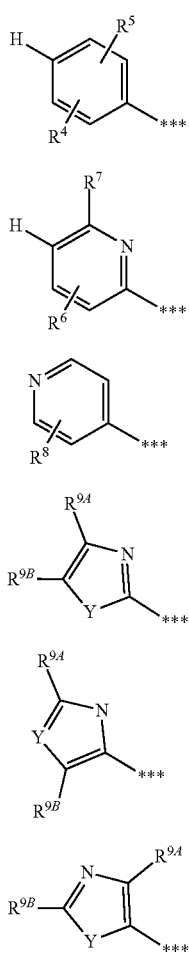

wherein *** marks the bond to the adjacent carbonyl group; and
$R^4$ is hydrogen, fluorine, chlorine, bromine or methyl;
$R^5$ is hydrogen, fluorine, chlorine, bromine, cyano, $(C_1-C_3)$-alkyl or $(C_1-C_3)$-alkoxy,
wherein $(C_1-C_3)$-alkyl and $(C_1-C_3)$-alkoxy are optionally up to trisubstituted by fluorine;
$R^6$ is hydrogen, fluorine, chlorine, bromine or methyl;
$R^7$ is hydrogen, $(C_1-C_3)$-alkoxy, cyclobutyloxy, oxetan-3-yloxy, tetrahydrofuran-3-yloxy, tetrahydro-2H-pyran-4-yloxy, mono-$(C_1-C_3)$-alkylamino, di-$(C_1-C_3)$-alkylamino or $(C_1-C_3)$-alkylsulfanyl,
wherein $(C_1-C_3)$-alkoxy may be up to trisubstituted by fluorine;
$R^8$ is hydrogen, fluorine, chlorine, bromine, $(C_1-C_3)$-alkyl or $(C_1-C_3)$-alkoxy,
$R^{9A}$ and $R^{9B}$ are identical or different and are independently hydrogen, fluorine, chlorine, bromine, $(C_1-C_3)$-alkyl, cyclopropyl or $(C_1-C_3)$-alkoxy,
wherein $(C_1-C_3)$-alkyl and $(C_1-C_3)$-alkoxy are optionally up to trisubstituted by fluorine;
and
Y is O or S;
or
$R^3$ is an —$OR^{10}$ or —$NR^{11}R^{12}$ group wherein
$R^{10}$ is $(C_1-C_6)$-alkyl, $(C_4-C_6)$-cycloalkyl or [$(C_3-C_6)$-cycloalkyl]methyl;
$R^{11}$ is hydrogen or $(C_1-C_3)$-alkyl;
and
$R^{12}$ is $(C_1-C_6)$-alkyl, $(C_3-C_6)$-cycloalkyl, phenyl or benzyl,
wherein $(C_1-C_6)$-alkyl is optionally up to trisubstituted by fluorine;
and
wherein phenyl and the phenyl group in benzyl are optionally up to trisubstituted by identical or different radicals selected from the group consisting of fluorine, chlorine, methyl, ethyl, trifluoromethyl, methoxy, ethoxy, trifluoromethoxy and (trifluoromethyl) sulfanyl;
or
$R^{11}$ and $R^{12}$ are attached to one another and, together with the nitrogen atom to which they are bonded, form a pyrrolidine, piperidine, morpholine or thiomorpholine ring,
or a salt, a solvate, or a solvate of the salt thereof,
in combination with one or more inert, nontoxic, pharmaceutically suitable excipients.

3. The method according to claim 1, wherein the ring Q is a diazaheterobicyclic system of the formula

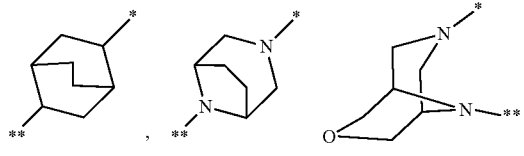

in which * denotes the bond to the adjacent $CHR^2$ group and ** the bond to the carbonyl group;
A is CH;
$R^1$ is chlorine, bromine, isopropyl or cyclopropyl;
$R^2$ is hydrogen;
and
$R^3$ is cyclopentyl or cyclohexyl;
or
$R^3$ is a phenyl group of the formula (a), a pyridyl group of the formula (b) or an azole group of the formula (d), (e) or (f)

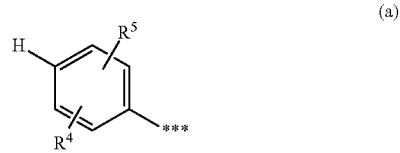

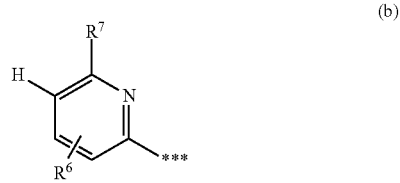

-continued (d)
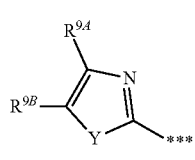

(e)
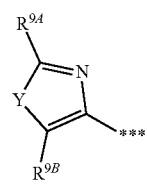

(f)
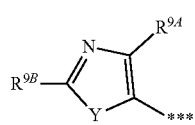

wherein *** marks the bond to the adjacent carbonyl group; and $R^4$ is hydrogen, fluorine or chlorine;

$R^5$ is fluorine, chlorine, methyl, isopropyl, methoxy or ethoxy;

$R^6$ is hydrogen, fluorine, chlorine, bromine or methyl;

$R^7$ is methoxy, difluoromethoxy, trifluoromethoxy, isopropoxy, cyclobutyloxy or methylsulfanyl;

$R^{9A}$ and $R^{9B}$ are identical or different and are independently hydrogen, methyl, trifluoromethyl, ethyl, isopropyl or cyclopropyl;

and

Y is O or S, or a salt, a solvate, or a solvate of the salt thereof.

4. The method of claim 1, wherein the compound is tert-Butyl 7-{[2-(4-chlorophenyl)imidazo[1,2-a]pyrimidin-3-yl]methyl}-3-oxa-7,9-diazabicyclo[3.3.1]nonane-9-carboxylate of the formula

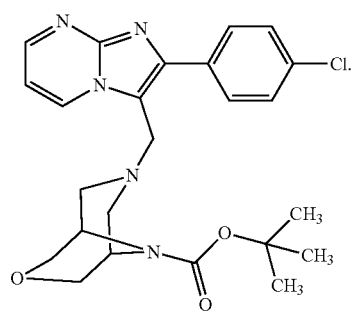 [SMILES: CC(C)(C)OC(=O)N1C2COCC1CN(Cc1c(-c3ccc(Cl)cc3)nc3ncccn13)C2]

5. The method of claim 1, wherein the compound is (5-{[2-(4-chlorophenyl)imidazo[1,2-a]pyrimidin-3-yl]methyl}-2,5-diazabicyclo[2.2.2]oct-2-yl)(3-fluoro-6-methoxypyridin-2-yl)methanone of the formula

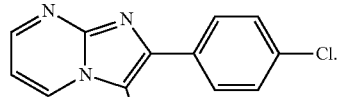
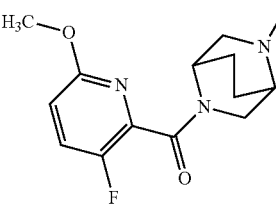

6. The method of claim 1, wherein the compound is (3-Fluoro-6-methoxypyridin-2-yl)(3-{[2-(4-isopropylphenyl)imidazo[1,2-a]pyrimidin-3-yl]methyl}-3,8-diazabicyclo[3.2.1]oct-8-yl)methanone of the formula

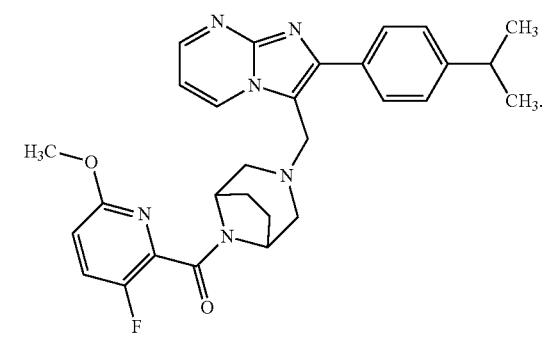 [SMILES: COc1ccc(F)c(C(=O)N2C3CCC2CN(Cc2c(-c4ccc(C(C)C)cc4)nc4ncccn24)C3)n1]

7. The method of claim 1, wherein the compound is ((3-Chloro-6-methoxypyridin-2-yl)(3-{[2-(4-isopropylphenyl)imidazo[1,2-a]pyrimidin-3-yl]methyl}-3,8-diazabicyclo[3.2.1]oct-8-yl)methanone of the formula

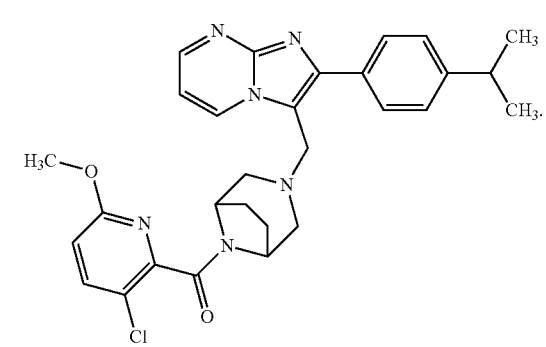 [SMILES: COc1ccc(Cl)c(C(=O)N2C3CCC2CN(Cc2c(-c4ccc(C(C)C)cc4)nc4ncccn24)C3)n1]

8. The method of claim 1, wherein the compound is (3-{[2-(4-chlorophenyl)imidazo[1,2-a]pyrimidin-3-yl]methyl}-3,8-diazabicyclo[3.2.1]oct-8-yl) [6-(methylamino)pyridin-2-yl] methanone of the formula

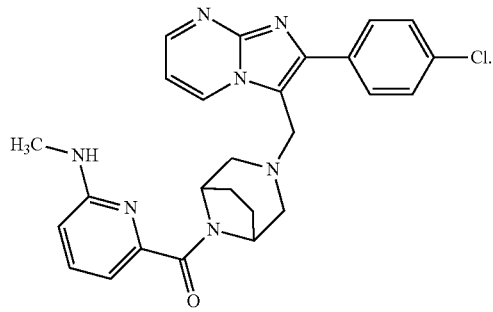 [SMILES: CNc1cccc(C(=O)N2C3CCC2CN(Cc2c(-c4ccc(Cl)cc4)nc4ncccn24)C3)n1]

9. The method of claim 1, wherein the compound is (3-{[2-(4-chlorophenyl)imidazo[1,2-a]pyrimidin-3-yl]methyl}-3,8-diazabicyclo[3.2.1]oct-8-yl)(3-methoxyphenyl)methanone of the formula

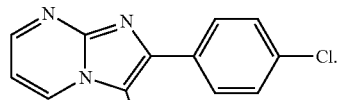
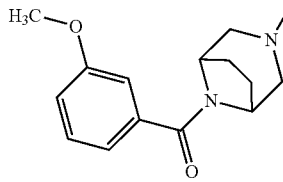

10. The method of claim 1, wherein the compound is (5-{[2-(4-chlorophenyl)imidazo[1,2-a]pyrimidin-3-yl]methyl}-2,5-diazabicyclo[2.2.2]oct-2-yl)(cyclopentyl)methanone of the formula

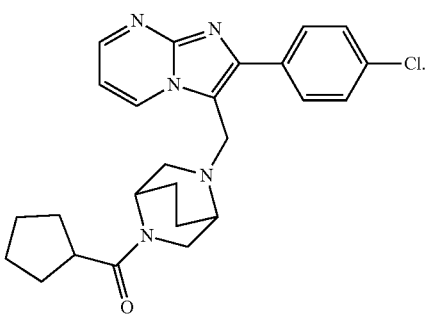 [SMILES: O=C(C1CCCC1)N1CC2CCC1CN2Cc1c(-c2ccc(Cl)cc2)nc2ncccn12]

* * * * *